US008580965B2

(12) United States Patent
Oberboersch et al.

(10) Patent No.: US 8,580,965 B2
(45) Date of Patent: Nov. 12, 2013

(54) SUBSTITUTED SULFONAMIDE COMPOUNDS

(75) Inventors: Stefan Oberboersch, Aachen (DE); Melanie Reich, Aachen (DE); Stefan Schunk, Aachen (DE); Sabine Hees, Aachen (DE); Ruth Jostock, Stolberg (DE); Michael Engels, Turnhout (BE); Achim Kless, Aachen (DE); Thomas Christoph, Aachen (DE); Klaus Schiene, Duesseldorf (DE); Tieno Germann, Aachen (DE); Edward Bijsterveld, GE Nijmegen (NL)

(73) Assignee: Gruenenthal GmbH, Aachen (DE)

( * ) Notice: Subject to any disclaimer, the term of this patent is extended or adjusted under 35 U.S.C. 154(b) by 1538 days.

(21) Appl. No.: 11/873,065

(22) Filed: Oct. 16, 2007

(65) Prior Publication Data

US 2008/0249128 A1    Oct. 9, 2008

Related U.S. Application Data

(60) Provisional application No. 60/851,740, filed on Oct. 16, 2006.

(30) Foreign Application Priority Data

Oct. 16, 2006   (DE) .......................... 10 2006 049 412

(51) Int. Cl.
*C07D 211/52* (2006.01)
*C07D 401/02* (2006.01)
*C07D 409/04* (2006.01)

(52) U.S. Cl.
USPC ........... 546/217; 546/194; 546/202; 546/212; 546/213; 514/318; 514/324; 514/326; 514/327

(58) Field of Classification Search
USPC .......... 514/318, 324, 326, 327; 546/194, 202, 546/212, 213, 217
See application file for complete search history.

(56) References Cited

U.S. PATENT DOCUMENTS

| | | | |
|---|---|---|---|
| 3,551,568 A | | 12/1970 | Kaiser et al. |
| 6,136,827 A | * | 10/2000 | Caldwell et al. ............... 514/329 |
| 7,601,844 B2 | * | 10/2009 | Carter et al. .................. 546/228 |
| 2006/0178360 A1 | | 8/2006 | Barth et al. |
| 2009/0253669 A1 | * | 10/2009 | Oberboersch et al. ... 514/210.01 |

FOREIGN PATENT DOCUMENTS

| | | |
|---|---|---|
| DE | 103 22 191 A1 | 12/2004 |
| JP | 2003-505384 | 2/2003 |
| JP | 2005-532354 | 10/2005 |
| JP | 2006-521333 A | 9/2006 |
| JP | 2008-516901 | 5/2008 |
| WO | WO 98/17655 A1 | 4/1998 |
| WO | WO01/05783 | 1/2001 |
| WO | WO 02/076964 A1 | 10/2002 |
| WO | WO03/103671 | 12/2003 |
| WO | WO 2006/010968 A1 | 2/2006 |
| WO | WO2006/040004 | 4/2006 |
| WO | WO 2007/101007 A2 | 9/2007 |

OTHER PUBLICATIONS

Jacob et al. "Use of proteinase . . . " CA 139:678650 (2003).*
Oberboersch et al. "Preparation of . . . " CA148:495803 (2008).*
Cheng et al. "CCR1 antagonists" Mol. Divers v.12, p. 17-23 (2008).*
Miller et al. "The chemist's companion guide . . . " p. 35 (2011).*
USPTO connection v.2 (1) p. 1-3 (2005).*
R. Hayashi et al., "Bradykinin stimulates IL-6 and IL-8 production by human lung fibroblasts through ERK- and p38 MAPK-dependent mechanisms", European Respiratory Journals Ltd. 2000; vol. 16, pp. 452-458.
Joäo B. Pesquero et al., "Hypoalgesia and altered inflammatory responses in mice lacking kinin B1 receptors", PNAS, Jul. 5, 2000, vol. 97, No. 14, pp. 8140-8145.
Joäo B. Calixto et al., "Kinin $B_1$ receptors: key G-protein-coupled receptors and their role in inflammatory and painful processes", British Journal of Pharmacology (2004) vol. 413, pp. 803-818.
Giselle F. Passos et al., "Kinin $B_1$ Receptor Up-Regulation after Lipopolysaccharide Adminstration: Role of Proinflammatory Cytokines and Neutrophil Influx[1]", The Journal of Immunology, 2004, vol. 172, pp. 1839-1847.
L.M. Fredrik Leeb-Lundberg et al., "International Union of Pharmacology. XLV. Classification of the Kinin Receptor Family: from Molecular Mechanisms to Pathophysiological Consequences", vol. 57, No. 1, pp. 27-77, (2005).
Antoni Stadnicki et al., "Immunolocalization and expression of kinin B1R and B 2R receptors in human inflammatory bowel disease", Am J Physiol Gastrointest Liver Physiol 2005, vol. 289, pp. 261-266.
Bichoy H. Gabra et al., "The kinin system mediates hyperalgesia through the inducible bradykinin B1 receptor subtype: evidence in various experimental animal models of type 1 and type 2 diabetic neuropathy", Biol Chem., Feb. 2006, vol. 387, pp. 127-143.
J. Fred Hess et al., "Generation and characterization of a humanized bradykinin B1 receptor mouse", Biol Chem. Feb. 2006, vol. 387, pp. 195-201.
Joäo B. Pesquero et al., "Genetically altered animal models in the kallikrein-kinin system", Biol Chem., Feb. 2006, vol. 387, pp. 119-126.
Sara H. Bengtson et al., "Kinin receptor expression during *Staphylococcus aureus* infection", Blood, Sep. 15, 2006, vol. 108, No. 6., pp. 2055-2063.
Elemer Fogassy et al., "Optical resolution methods", The Royal Society of Chemistry 2006, Org. Biomol. Chem. 2006, vol. 4, pp. 3011-3030.
A. Prat, MD. et al., "Bradykinin $B_1$ receptor experession and function on T lymphocytes in active multiple sclerosis", 1999 by the American Academy of Neurology, pp. 2087-2092.
German Search Report dated Aug. 6, 2007, including an English translation (Nine (9) pages).
International Search Report dated Feb. 28, 2008, including an English translation of the pertinent portions (Five (5) pages).
Form PCT/ISA/220 and Form PCT/ISA/237 dated Feb. 28, 2008 (Eight (8) pages).

* cited by examiner

*Primary Examiner* — Celia Chang
(74) *Attorney, Agent, or Firm* — Crowell & Moring LLP

(57) ABSTRACT

Substituted sulfonamide compounds with bradykinin receptor (B1R) modulating activity; processes for the preparation thereof, pharmaceutical compositions comprising such compounds, and methods of using such compounds to treat or inhibit pain and/or other disorders and/or disease states.

15 Claims, No Drawings

SUBSTITUTED SULFONAMIDE COMPOUNDS

CROSS REFERENCE TO RELATED APPLICATIONS

This application claims priority from co-pending U.S. provisional patent application No. 60/851,740, filed Oct. 16, 2006. Priority is also claimed based upon Federal Republic of Germany patent application no. DE 10 2006 049 412.1, filed Oct. 16, 2006, the entire disclosure of which is incorporated herein by reference.

BACKGROUND OF THE INVENTION

The present invention relates to substituted sulfonamide derivatives, processes for the preparation thereof, medicaments comprising these compounds and the use of substituted sulfonamide derivatives for the preparation of medicaments.

In contrast to constitutive expression of the bradykinin 2 receptor (B2R), the bradykinin 1 receptor (B1R) is not or is only weakly expressed in most tissues. Nevertheless, expression of the B1R can be induced on various cells. For example, in the course of inflammation reactions, a rapid and pronounced induction of the B1R takes place on neuronal cells, but also on various peripheral cells, such as fibroblasts, endothelial cells, granulocytes, macrophages and lymphocytes. Thus, in the course of inflammation reactions, a switch from a B2R to a B1R dominance occurs on the cells involved. The cytokines interleukin-1 (IL-1) and tumour necrosis factor alpha (TNFα) are involved considerably in this upwards regulation of B1R (Passos et al. J. Immunol. 2004, 172, 1839-1847). After activation with specific ligands, B1R-expressing cells can subsequently themselves secrete inflammation-promoting cytokines, such as IL-6 and IL-8 (Hayashi et al., Eur. Respir. J. 2000, 16, 452-458). This leads to inwards migration of further inflammation cells, e.g. neutrophilic granulocytes (Pesquero et al., PNAS 2000, 97, 8140-8145). The bradykinin B1R system can contribute towards the chronification of diseases via these mechanisms. This is demonstrated by a large number of animal studies (overviews in Leeb-Lundberg et al., Pharmacol Rev. 2005, 57, 27-77 and Pesquero et al., Biol. Chem. 2006, 387, 119-126). In humans also, an increased expression of the B1R also manifests itself, e.g. on enterocytes and macrophages in the affected tissue of patients with inflammatory bowel diseases (Stadnicki et al., Am. J. Physiol. Gastrointest. Liver Physiol. 2005, 289, G361-366) or on T lymphocytes of patients with multiple sclerosis (Prat, 1999) or an activation of the bradykinin B2R-B1R system manifests itself in the course of infections with *Staphylococcus aureus* (Bengtson et al., Blood 2006, 108, 2055-2063). Infections with *Staphylococcus aureus* are responsible for clinical syndromes such as superficial infections of the skin up to septic shock.

Based on the pathophysiological relationships described, there is a great therapeutic potential for the use of B1R antagonists against acute and in particular chronically inflammatory diseases. These include diseases of the respiratory tract (bronchial asthma, allergies, COPD/chronic obstructive pulmonary disease, cystic fibrosis etc.), inflammatory bowel diseases (ulcerative colitis, CD/Crohn's disease etc.), neurological diseases (multiple sclerosis, neurodegeneration etc.), inflammations of the skin (atopic dermatitis, psoriasis, bacterial infections etc.) and mucosa (Behcet's disease, pelvitis, prostatitis etc.), rheumatic diseases (rheumatoid arthritis, osteoarthritis etc.), septic shock and reperfusion syndrome (following cardiac infarction, apoplexy).

The bradykinin (receptor) system is moreover also involved in the regulation of angiogenesis (potential as an angiogenesis inhibitor in cases of cancer and macula degeneration on the eye), and B1R-knockout mice are protected from induction of obesity by a particularly high-fat diet (Pesquero et al., Biol. Chem. 2006, 387, 119-126). B1R antagonists are therefore also suitable for treatment of obesity.

B1R antagonists are particularly suitable for treatment of pain, in particular inflammatory pain and neuropathic pain (Calixto et al., Br. J. Pharmacol 2004, 1-16), and here in particular diabetic neuropathy (Gabra et al., Biol. Chem. 2006, 387, 127-143).

In the development of B1R modulators there is the problem, however, that the human and the rat B1R receptor differ so widely that many compounds which are good B1R modulators on the human receptor have only a poor or no affinity for the rat receptor. This makes animal pharmacology studies considerably more difficult, since many studies are usually conducted on the rat. However, if there is no activity on the rat receptor, neither action nor side-effect can be investigated on the rat. This has already meant that transgenic animals with human B1 receptors have been produced for animal pharmacology studies (Hess et al., Biol. Chem. 2006; 387(2):195-201). Working with transgenic animals is more expensive, needless to say, than working with the unmodified animals. However, since in the development of medicaments precisely long-term toxicity studies on the rat belong to the standard investigations, but this does not make sense in the case of a lack of activity on the receptor, the development of such compounds lacks an important established instrument for checking safety. There is therefore a need for B1R modulators, in particular those which bind both to the rat receptor and to the human receptor.

SUMMARY OF THE INVENTION

It was an object of the invention, therefore, to provide novel compounds which are suitable in particular as pharmacological active compounds in medicaments, preferably in medicaments for treatment of disorders or diseases which are at least partly mediated by B1R receptors.

These and other objects have been achieved in accordance with the present invention by providing substituted sulfonamide compounds corresponding to formula I

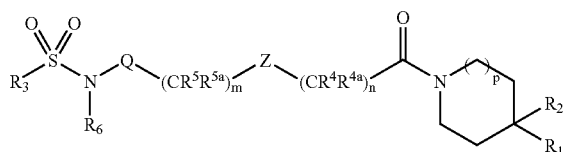

wherein
m represents 0, 1, 2 or 3
n represents 1 or 2
p represents 0, 1 or 2,
$R^1$ represents aryl or heteroaryl, unsubstituted or mono- or poly-substituted, optionally linked via a $C_{1-6}$-alkyl chain, which can be saturated or unsaturated, branched or unbranched,
$R^2$ represents OH, $OC_{1-6}$-alkyl or F,
$R^3$ represents aryl or heteroaryl, in each case unsubstituted or mono- or poly-substituted;

$R^4$ and $R^{4a}$ independently of one another represent H, $C_{1-6}$-alkyl, in each case saturated or unsaturated, branched or unbranched, unsubstituted or mono- or poly-substituted; F; Cl; aryl, in each case unsubstituted or mono- or poly-substituted; or aryl linked via a $C_{1-3}$-alkyl chain and in each case unsubstituted or mono- or poly-substituted;

Z represents O, $CH_2$ or $NR^N$, wherein $R^N$ denotes H; $C_{1-6}$-alkyl; phenyl, $C_{3-8}$-cycloalkyl, methyl-$C_{3-8}$-cycloalkyl or benzyl, in each case unsubstituted or mono- or poly-substituted;

$R^5$ and $R^{5a}$ independently of one another represent H; or $C_{1-6}$-alkyl, in each case saturated or unsaturated, branched or unbranched, unsubstituted or mono- or poly-substituted; OH, $OC_{1-6}$-alkyl, F, Cl, phenoxy or benzyloxy;

$R^6$ represents H; $C_{1-6}$-alkyl, in each case saturated or unsaturated, branched or unbranched, unsubstituted or mono- or poly-substituted; $C_{3-8}$-cycloalkyl, saturated or unsaturated, unsubstituted or mono- or poly-substituted; aryl or heteroaryl, unsubstituted or mono- or poly-substituted; aryl or $C_{3-8}$-cycloalkyl linked via a $C_{1-3}$-alkyl chain; or together with Q, including the adjacent nitrogen, forms a four-, five-, six- or seven-membered ring, which can be saturated or unsaturated and can contain a further heteroatom O, S or N, on to which a further five- or six-membered ring, saturated or unsaturated, can be fused; wherein in the case of the common ring closure Q represents

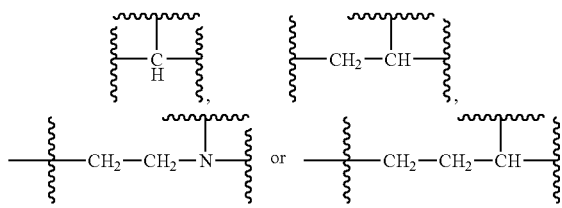

and the ring can be substituted in any position by phenyl, OH, $OR^N$, F, Cl, $CF_3$ or $C_{1-6}$-alkyl; or Q denotes a single bond, —$CH_2$—, —$CH_2$—$CH_2$—, or

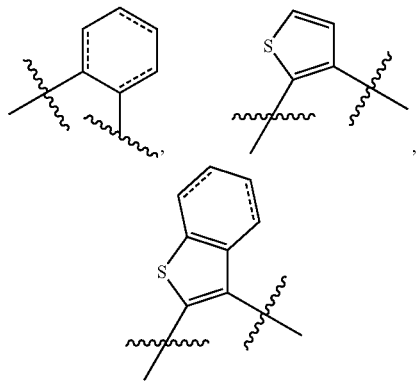

wherein ==== represents a single bond or a double bond;
in the form of the racemate; of the enantiomers, diastereomers, mixtures of the enantiomers or diastereomers or of an individual enantiomer or diastereomer; of the bases and/or salts of physiologically acceptable acids. The compounds have an affinity for the B1R receptor.

In the context of this invention, the expression "substituted" means the replacement of an H atom by a substituent specified in more detail elsewhere.

In the context of this invention, the expressions "$C_{1-3}$-alkyl" and "$C_{1-6}$-alkyl" include acyclic saturated or unsaturated hydrocarbon radicals, which can be branched- or straight-chain and unsubstituted or mono- or poly-substituted, having from 1 to 3 C atoms or, respectively, from 1 to 6 C atoms, i.e. $C_{1-3}$-alkanyls, $C_{2-3}$-alkenyls and $C_{2-3}$-alkynyls or, respectively, $C_{1-6}$-alkanyls, $C_{2-6}$-alkenyls and $C_{2-6}$-alkynyls. In this context, alkenyls contain at least one C—C double bond and alkynyls contain at least one C—C triple bond. Alkyl is advantageously chosen from the group which includes methyl, ethyl, n-propyl, 2-propyl, n-butyl, iso-butyl, sec-butyl, tert-butyl, n-pentyl, iso-pentyl, neo-pentyl, hexyl, heptyl, octyl, ethylenyl (vinyl), ethynyl, propenyl (—$CH_2CH$=$CH_2$, —$CH$=$CH$—$CH_3$, —$C$(=$CH_2$)—$CH_3$), propynyl (—$CH$—$C$≡$CH$, —$C$≡$C$—$CH_3$), butenyl, butynyl, pentenyl, pentynyl, hexenyl and hexynyl. Methyl, ethyl and n-propyl are particularly advantageous.

In the context of this invention, the expression "aryl" denotes aromatic hydrocarbons, inter alia phenyls and naphthyls. The aryl radicals can also be fused with further saturated, (partly) unsaturated or aromatic ring systems. Each aryl radical can be unsubstituted or mono- or poly-substituted, where the substituents on the aryl can be identical or different and in any desired and possible position of the aryl. Aryl is advantageously chosen from the group which contains phenyl, 1-naphthyl, 2-naphthyl, each of which can be unsubstituted or mono- or poly-substituted. The phenyl radical is particularly advantageous.

The expression "heteroaryl" represents a 5-, 6- or 7-membered cyclic aromatic radical which contains at least 1, optionally also 2, 3, 4 or 5 heteroatoms, where the heteroatoms are identical or different and the heterocyclic ring can be unsubstituted or mono- or poly-substituted; in the case of substitution on the heterocyclic ring, the substituents can be identical or different and can be in any desired and possible position of the heteroaryl. The heterocyclic ring can also be part of a bi- or poly-cyclic system. Preferred heteroatoms are nitrogen, oxygen and sulfur. It is preferable for the heteroaryl radical to be chosen from the group which contains pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, phthalazinyl, pyrazolyl, imidazolyl, thiazolyl, oxadiazolyl, isoxazolyl, pyridyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, where the bonding to the compounds of the general structure I can be effected via any desired and possible ring member of the heteroaryl radical. Thienyl, pyrrolyl and pyridyl are particularly preferred.

For the purposes of the present invention, the expression "aryl or heteroaryl bonded via $C_{1-3}$-alkyl" and "aryl or heteroaryl bonded via $C_{1-6}$-alkyl" mean that $C_{1-3}$-alkyl and $C_{1-6}$-alkyl and aryl and heteroaryl have the meanings defined above and the aryl or heteroaryl radical is bonded to the compound of the general structure I via a $C_{1-3}$-alkyl group or a $C_{1-6}$-alkyl group. Phenyl, benzyl and phenethyl are particularly advantageous in the context of this invention.

In connection with "alkyl" and "cycloalkyl", in the context of this invention the term "substituted" is understood as meaning replacement of a hydrogen radical by F, Cl, Br, I, —CN, $NH_2$, NH—$C_{1-6}$-alkyl, NH—$C_{1-6}$-alkyl-OH, $C_{1-6}$-alkyl, $N(C_{1-6}$-alkyl$)_2$, $N(C_{1-6}$-alkyl-OH$)_2$, $NO_2$, SH, S—$C_{1-6}$-alkyl, S-benzyl, O—$C_{1-6}$-alkyl, OH, O—$C_{1-6}$-alkyl-OH, =O, O-benzyl, C(=O)$C_{1-6}$-alkyl, $CO_2H$, $CO_2$—$C_{1-6}$-alkyl, phenyl or benzyl, where polysubstituted radicals are to be understood as meaning those radicals which are substituted several times, e.g. two or three times, either on different or on the same atoms, for example three times on the same C atom as in the case of $CF_3$ or $CH_2CF_3$, or at different places as in the case of $CH(OH)-CH=CH-CHCl_2$. Polysubstitution can be with the same or with different substituents.

In respect of "aryl" and "heteroaryl", in the context of this invention "mono- or poly-substituted" is understood as meaning replacement one or more times, e.g. two, three or four times, of one or more hydrogen atoms of the ring system by F, Cl, Br, I, CN, $NH_2$, $NH-C_{1-6}$-alkyl, $NH-C_{1-6}$-alkyl-OH, $N(C_{1-6}$-alkyl$)_2$, $N(C_{1-6}$-alkyl-OH$)_2$, $NO_2$, SH, $S-C_{1-6}$-alkyl, OH, $O-C_{1-6}$-alkyl, $O-C_{1-6}$alkyl-OH, $C(=O)C_{1-6}$-alkyl, $NHSO_2C_{1-6}$-alkyl, $NHCOC_{1-6}$-alkyl, $CO_2H$, $CH_2SO_2$-phenyl, $CO_2-C_{1-6}$-alkyl, $OCF_3$, $CF_3$,

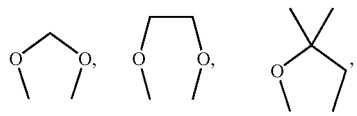

$C_{1-6}$-alkyl, pyrrolidinyl, piperidinyl, morpholinyl, benzyloxy, phenoxy, phenyl, pyridyl, alkylaryl, thienyl or furyl; on one or optionally various atoms, where a substituent can optionally be substituted in its turn. Polysubstitution in this context is with the same or with different substituents. Preferred substituents for "aryl" or "heteroaryl" here are —F, —$C_1$, $CF_3$, $CH_3$ or $OCH_3$.

In the context of this invention, the term of salt formed with a physiologically acceptable acid is understood as meaning salts of the particular active compound with inorganic or organic acids which are physiologically acceptable—in particular when used in humans and/or mammals. The hydrochloride is particularly preferred. Examples of physiologically acceptable acids are: hydrochloric acid, hydrobromic acid, sulfuric acid, methanesulfonic acid, formic acid, acetic acid, oxalic acid, succinic acid, tartaric acid, mandelic acid, fumaric acid, maleic acid, lactic acid, citric acid, glutamic acid, 1,1-dioxo-1,2-dihydro1$\lambda^6$-benzo[d]isothiazol-3-one (saccharic acid), monomethylsebacic acid, 5-oxo-proline, hexane-1-sulfonic acid, nicotinic acid, 2-, 3- or 4-aminobenzoic acid, 2,4,6-trimethyl-benzoic acid, α-liponic acid, acetylglycine, hippuric acid, phosphoric acid and/or aspartic acid. Citric acid and hydrochloric acid are particularly preferred.

In the context of this invention, preference is given to substituted sulfonamide derivatives of the general formula I wherein m represents 0, 1, 2 or 3
n represents 1 or 2
p represents 0, 1 or 2,
$R^1$ represents aryl or heteroaryl, unsubstituted or mono- or poly-substituted, optionally linked via a $C_{1-6}$-alkyl chain, which can be saturated or unsaturated, branched or unbranched,
$R^2$ represents OH, $OC_{1-6}$-alkyl or F,
$R^3$ represents aryl or heteroaryl, in each case unsubstituted or mono- or poly-substituted;
$R^4$ and $R^{4a}$ independently of one another represent H, $C_{1-6}$-alkyl, in each case saturated or unsaturated, branched or unbranched, unsubstituted or mono- or poly-substituted; F; Cl; aryl, in each case unsubstituted or mono- or poly-substituted; or aryl linked via a $C_{1-3}$-alkyl chain and in each case unsubstituted or mono- or poly-substituted;

Z represents O, $CH_2$ or $NR^N$, wherein $R^N$ denotes H; $C_{1-6}$-alkyl; phenyl, $C_{3-8}$-cycloalkyl, methyl-$C_{3-8}$-cycloalkyl or benzyl, in each case unsubstituted or mono- or poly-substituted;
$R^5$ and $R^{5a}$ independently of one another represent H; or $C_{1-6}$-alkyl, in each case saturated or unsaturated, branched or unbranched, unsubstituted or mono- or poly-substituted; OH, $OC_{1-6}$-alkyl, F, Cl, phenoxy or benzyloxy;
$R^6$ represents H; $C_{1-6}$-alkyl, in each case saturated or unsaturated, branched or unbranched, unsubstituted or mono- or poly-substituted; $C_{3-8}$-cycloalkyl, saturated or unsaturated, unsubstituted or mono- or poly-substituted; aryl or heteroaryl, unsubstituted or mono- or poly-substituted; aryl or $C_{3-8}$-cycloalkyl linked via a $C_{1-3}$-alkyl chain; or together with Q, including the adjacent nitrogen, forms a four-, five-, six- or seven-membered ring, which can be saturated or unsaturated and can contain a further heteroatom O, S or N, on to which a further five- or six-membered ring, saturated or unsaturated, can be fused; wherein in the case of the common ring closure Q represents

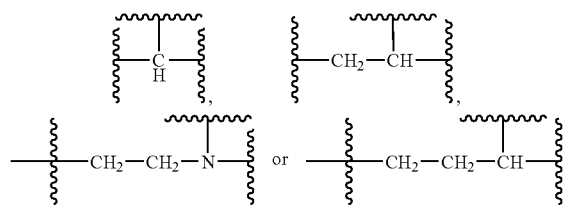

and the ring can be substituted in any position by phenyl, OH, $OR^N$, F, Cl, $CF_3$ or $C_{1-6}$-alkyl; or Q denotes a single bond, —$CH_2$—, —$CH_2$—$CH_2$—, or

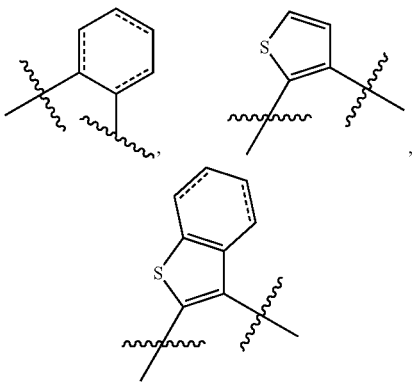

wherein ==== represents a single bond or a double bond;
wherein
"alkyl substituted" and "cycloalkyl substituted" denotes replacement of one or more hydrogen radicals by F, Cl, Br, I, —CN, $NH_2$, $NH-C_{1-6}$-alkyl, $NH-C_{1-6}$-alkyl-OH, $C_{1-6}$-alkyl, $N(C_{1-6}$-alkyl$)_2$, $N(C_{1-6}$-alkyl-OH$)_2$, $NO_2$, SH, $S-C_{1-6}$-alkyl, S-benzyl, $O-C_{1-6}$-alkyl, OH, $O-C_{1-6}$-alkyl-OH, =O, O-benzyl, $C(=O)C_{1-6}$-alkyl, $CO_2H$, $CO_2-C_{1-6}$-alkyl, phenyl or benzyl,
"aryl substituted" and "heteroaryl substituted" denotes replacement one or more times, e.g. two, three or four times, of one or more hydrogen atoms of the ring system by F, Cl, Br, I, CN, $NH_2$, $NH-C_{1-6}$-alkyl, $NH-C_{1-6}$-alkyl-OH, $N(C_{1-6}$-alkyl$)_2$, $N(C_{1-6}$-alkyl-OH$)_2$, $NO_2$, SH, $S-C_{1-6}$-alkyl, OH, O—$C_{1-6}$-alkyl, O—$C_{1-6}$alkyl-OH, C(=O)$C_{1-6}$-alkyl, $CO_2H$, $CH_2SO_2$-phenyl, $CO_2$—$C_{1-6}$-alkyl, $OCF_3$, $CF_3$,

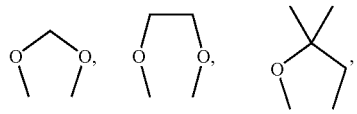

$C_{1-6}$-alkyl, phenyl, pyridyl, thienyl or furyl, in the form of the racemate; of the enantiomers, diastereomers, mixtures of the enantiomers or diastereomers or of an individual enantiomer or diastereomer; of the bases and/or salts of physiologically acceptable acids.

In the context of this invention, particular preference is given to substituted sulfonamide derivatives wherein $R^1$ denotes phenyl, pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, phthalazinyl, pyrazolyl, imidazolyl, thiazolyl, oxadiazolyl, isoxazolyl, pyridyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, in each case unsubstituted or mono- or poly-substituted and optionally linked via a $C_{1-3}$-alkyl chain.

Very particular preference is given to substituted sulfonamide derivatives wherein $R^1$ denotes thienyl, phenyl, benzyl, phenethyl, or pyridyl linked via a —$CH_2$— or —$CH_2$—$CH_2$— chain, in each case unsubstituted or mono- or poly-substituted, in particular pyridyl, or thienyl, phenyl or benzyl, unsubstituted or substituted. Particularly preferred substituents here are —F, —Cl, Br, I or $CF_3$.

For the phenyl group, particular preference is given to phenyl groups monosubstituted in the 2-, 3- or 4-position, in particular in the 3- or 4-position.

Particular preference is given to compounds in which $R^1$ is selected from 2-pyridinyl, 3-pyridinyl or 4-pyridinyl, preferably 3-pyridinyl or 4-pyridinyl, in particular 3-pyridinyl. Furthermore, $R^1$ preferably represents a group of the

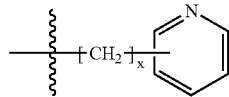

type, wherein x can be 1, 2 or 3, preferably 1 or 2, and the alkyl chain can be bonded at the 2-, 3- or 4-position of the pyridyl group, preferably at the 3- or 4-position, in particular at the 3-position. It is likewise preferred for $R^1$ to represent a group of the

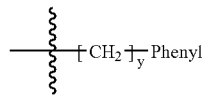

type, wherein y can be 1, 2 or 3, preferably 1 or 2, and the phenyl group can be unsubstituted or substituted by one or more identical or different substituents. The substituents are preferably selected from the group consisting of —F, —Cl, —Br, —I, —$CF_3$, in particular —F, —Cl, —Br and —$CF_3$, particular preference being given to phenyl groups monosubstituted in the 2-, 3- or 4-position, in particular in the 3- or 4-position. $R^1$ can further preferably represent 2-thienyl, optionally mono- or poly-substituted, preferably unsubstituted.

Preference is further given to substituted sulfonamide derivatives of the general formula I wherein $R^2$ represents OH.

Preference is also given to substituted sulfonamide derivatives of the general formula I wherein $R^3$ represents phenyl, naphthyl, thienyl or benzothienyl or benzothiophene, in each case unsubstituted or mono- or poly-substituted. Particular preference is given to phenyl, unsubstituted or mono- or poly-substituted, wherein the substituents are preferably selected from the group consisting of -Me, —$CF_3$, —F, —Cl, —Br, —I, —OMe, and wherein the following substitution patterns on the phenyl group are particularly preferred: 2, 4 and 6; 2 and 4 and also 2 and 6.

Particular preference is further given to compounds of the general formula I wherein $R^3$ is 1-naphthyl, unsubstituted or mono- or poly-substituted, in particular 1-naphthyl substituted in the 2-position by methyl. $R^3$ can also preferably represent benzothienyl, in particular benzothien-3-yl, unsubstituted or mono- or poly-substituted.

Particular preference is given to substituted sulfonamide derivatives of the general formula I wherein $R^3$ represents 2-methyl-5-fluorophenyl, 2,4-dichlorophenyl, 3,5-dichlorophenyl, 3,4-dimethoxyphenyl, 2,6-dichlorophenyl, benzo[1,3]dioxole, 4-tert-butylphenyl, 4-trifluoromethylphenyl, 2,4,6-trimethylphenyl, 2,4,6-trichlorophenyl, 2,4-dichloro-6-methylphenyl, 4-methoxyphenyl, 3-trifluoromethylphenyl, 4-methylphenyl, 2,3,6-trimethyl-4-methoxyphenyl, pentafluorophenyl, 2-methoxyphenyl, 2,6-dimethyl-4-methoxyphenyl, 4-fluorophenyl, 4-chlorophenyl, 3,4-dichlorophenyl, 2,4-dimethoxyphenyl or 2,3-dichlorophenyl.

Very particular preference is given to substituted sulfonamide derivatives of the general formula I wherein $R^3$ denotes 2,6-dimethyl-4-methoxyphenyl.

In the compounds of formula I according to the invention it is preferable if, when n denotes 1, $R^{4a}$ represents H.

Preference is given also to substituted sulfonamide derivatives of the general formula I wherein $R^4$ and $R^{4a}$ represent H.

Preference is further given to substituted sulfonamide derivatives of the general formula I wherein Z represents O.

Moreover, preference is given to substituted sulfonamide derivatives of the general formula I wherein $R^5$ and $R^{5a}$ represent H.

Preference is further given to substituted sulfonamide derivatives of the general formula I, wherein Q denotes a single bond, —$CH_2$—, —$CH_2$—$CH_2$—, or

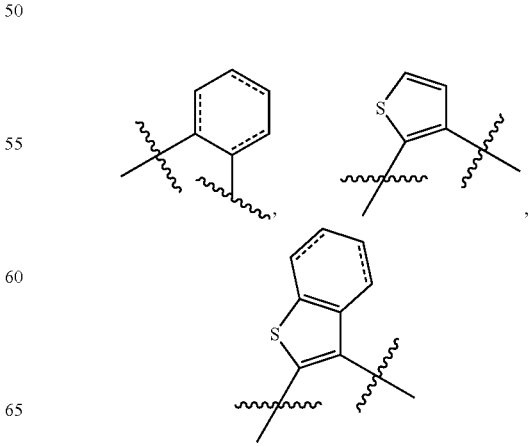

wherein ---- represents a single bond or a double bond. In a preferred embodiment of the present invention Q denotes a single bond.

Preference is further given to substituted sulfonamide derivatives of the general formula I wherein $R^6$ represents H, methyl, ethyl, n-propyl, isobutyl, cyclopropyl, cyclopropyl linked via a $C_{1-3}$-alkyl chain, or benzyl and Q represents a single bond.

In a further preferred embodiment of the present invention in the sulfonamide derivatives according to general formula I $R^6$ together with Q, including the adjacent nitrogen, forms a six- or seven-membered ring, preferably a six-membered ring, which can be saturated or unsaturated and can contain a further heteroatom O, S or N, on to which a further five- or six-membered ring, saturated or unsaturated, can be fused; wherein in the case of the common ring closure Q represents

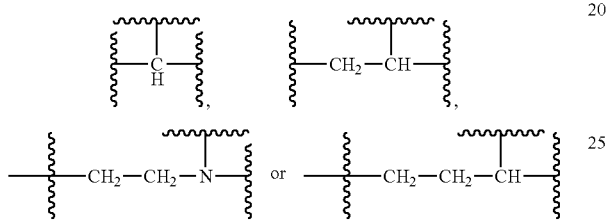

and the ring can be substituted in any position by phenyl, OH, $OR^N$, F, Cl, $CF_3$ or $C_{1-6}$-alkyl; Preferably, the six or seven-membered ring does not contain any additional heteroatom.

Preference is further given to substituted sulfonamide derivatives of the general formula I wherein represents

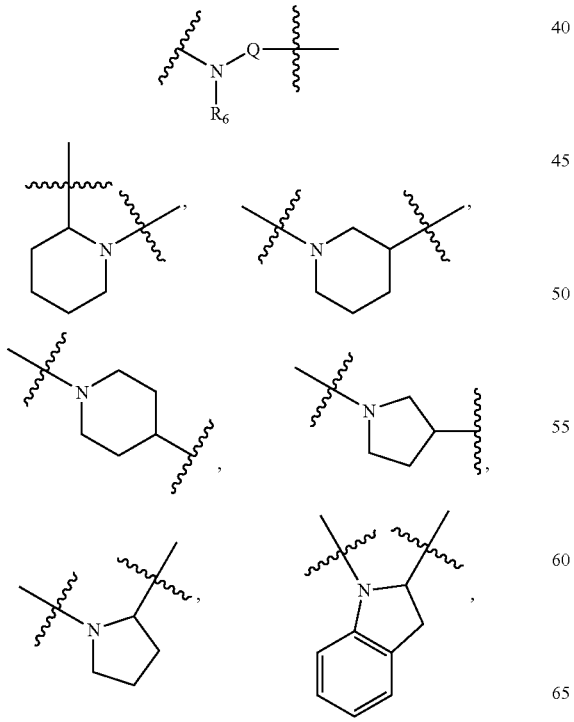

especially

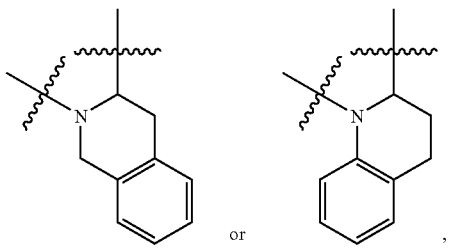

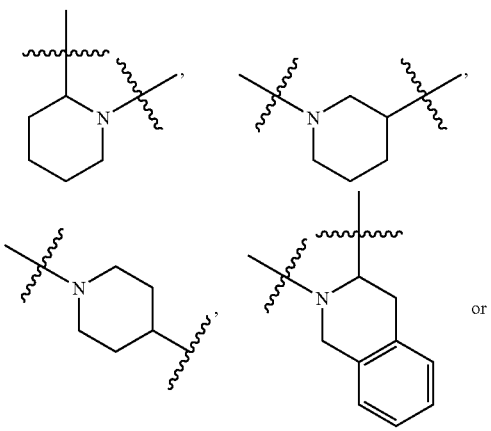

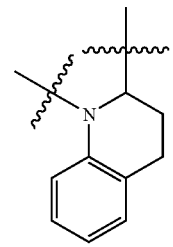

Preference is given also to substituted sulfonamide derivatives of the general formula I wherein Q denotes

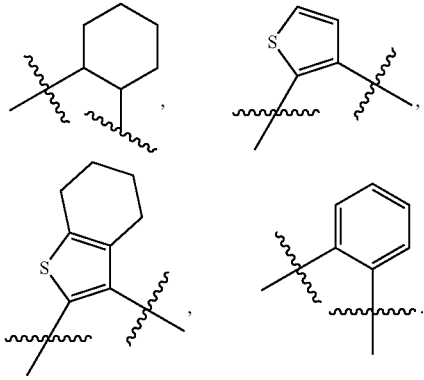

Preference is further given to compounds of the general formula I according to the invention wherein:

a) m represents 1; n represents 1 or 2, in particular 1; $R^4$, $R^{4a}$, $R^5$ and $R^{5a}$ represent H; and Z represents O; or b) m represents 0; Z represents O or $CH_2$, in particular O; n represents 1 or 2, in particular 1; and $R^4$ and $R^{4a}$ represent H.

These two variants according to the invention are particularly preferred in the compounds according to the invention wherein the group

[structure: N(R_6)–Q– open chain]

represents the N-containing rings described above.

Preference is further given to compounds of the general formula I according to the invention wherein: c) m represents 2; Z represents O; n represents 1 or 2, in particular 1; $R^4$, $R^{4a}$, $R^5$ and $R^{5a}$ represent H; or d) m represents 1 or 2, in particular 1; Z represents $CH_2$; n represents 1; and $R^4$, $R^{4a}$, $R^5$ and $R^{5a}$ represent H.

These two variants according to the invention are particularly preferred in the compounds according to the invention wherein the group

[structure: N(R_6)–Q–]

does not form an N-containing ring but an open-chained structure.

Preference is further given to substituted sulfonamide derivatives of the general formula I according to the invention wherein $R^1$ is selected from the group consisting of 2-pyridinyl, 3-pyridinyl or 4-pyridinyl, preferably 3-pyridinyl or 4-pyridinyl, in particular 3-pyridinyl;

[structure: –(CH_2)_x–pyridyl]

wherein x can be 1, 2 or 3, preferably 1 or 2, and the alkyl chain can be bonded at the 2-, 3- or 4-position of the pyridyl group, preferably at the 3- or 4-position, in particular at the 3-position;

[structure: –(CH_2)_y–Phenyl]

wherein y can be 1, 2 or 3, preferably 1 or 2, and the phenyl group can be unsubstituted or substituted by one or more identical or different substituents, the substituents preferably being selected from the group consisting of —F, —Cl, —Br, —I, $CF_3$, in particular —F, —Cl, Br and $CF_3$, particular preference being given to phenyl groups monosubstituted in the 2-, 3- or 4-position, in particular in the 3- or 4-position; and 2-thienyl, optionally mono- or poly-substituted, preferably unsubstituted;

$R^2$ represents OH or $OC_{1-6}$-alkoxy, preferably OH;

$R^3$ is selected from the group consisting of phenyl, unsubstituted or mono- or poly-substituted, the substituents preferably being selected from the group consisting of -Me, —$CF_3$, —F, —Cl, —Br, —I, —OMe, particular preference being given to the following substitution patterns on the phenyl group: 2, 4 and 6; 2 and 4 and also 2 and 6;

naphthyl, in particular 1-naphthyl, unsubstituted or mono- or poly-substituted, in particular naphthyl substituted in the 2-position by methyl; and benzothienyl, in particular benzothien-3-yl, unsubstituted or mono- or poly-substituted;

and in the group

[structure: N(R_6)–(CR^{5a}R^5)_m–Z–(CR^{4a}R^4)_n–]

of formula I:

a) n represents 1,
$R^4$ and $R^{4a}$ represent H,
Z represents O or $CH_2$, in particular O,
m represents 1 or 0, in particular 1,
$R^5$ and $R^{5a}$ represent H,
and

[structure: N(R_6)–Q–]

represents

[structures: piperidine N-linked; pyrrolidine N-linked; tetrahydroquinoline; 3-piperidinyl; 3-pyrrolidinyl; 4-piperidinyl; indoline]

-continued

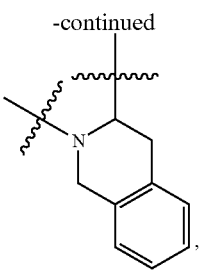

in particular

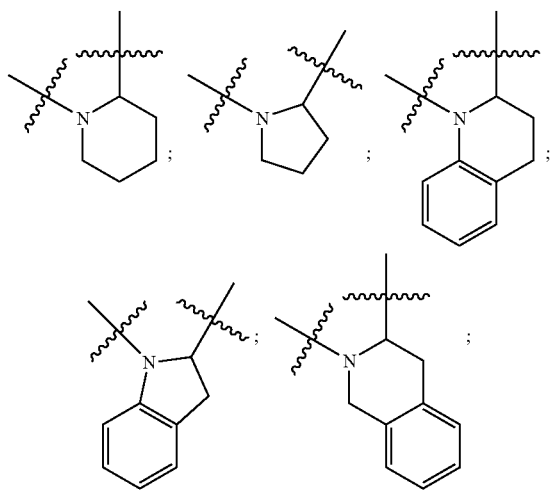

or
b) represents 1,
R$^4$ and R$^{4a}$ represent H,
Z represents O,
m represents 1,
R$^5$ and R$^{5a}$ represent H,
Q represents —CH$_2$—, and
R$^6$ represents H, C$_{1-4}$-alkyl, in particular methyl and ethyl, C$_{3-5}$-cycloalkyl, in particular cyclopropyl, C$_{3-5}$-cycloalkyl linked via a (—CH$_2$—)— or (—CH$_2$—CH$_2$—)— bridge, in particular —CH$_2$-cyclopropyl, phenyl or benzyl.

Very particular preference is given to substituted sulfonamide compounds according to the invention selected from the group consisting of:

1    N-{2-[2-(4-benzyl-4-hydroxy-piperidin-1-yl)-2-oxo-ethoxy]-ethyl}-N-ethyl-4-methoxy-2,3,6-trimethyl-phenylsulfonamide
2    2,4,6-trichloro-N-{2-[2-(4'-hydroxy-3',4',5',6'-tetrahydro-2'H-[3,4']bipyridinyl-1'-yl)-2-oxo-ethoxy]-ethyl}-N-methyl-phenylsulfonamide
3    N-(2-(2-(4-hydroxy-4-(pyridin-3-yl)piperidin-1-yl)-2-oxoethoxy)ethyl)-4-methoxy-N,2,6-trimethylphenylsulfonamide hydrochloride
4    N-{2-[2-(4'-hydroxy-3',4',5',6'-tetrahydro-2'H-[2,4']bipyridinyl-1'-yl)-2-oxo-ethoxy]-ethyl}-4-methoxy-2,6,N-trimethyl-phenylsulfonamide
5    2,4,6-trichloro-N-(2-(2-(4-hydroxy-4-(pyridin-3-yl)piperidin-1-yl)-2-oxoethoxy)ethyl)-N-methylphenylsulfonamide hydrochloride
6    2,4,6-trichloro-N-{2-[2-(4'-hydroxy-3',4',5',6'-tetrahydro-2'H-[2,4']bipyridinyl-1'-yl)-2-oxo-ethoxy]-ethyl}-N-methyl-phenylsulfonamide
7    1-(4-benzyl-4-hydroxy-piperidin-1-yl)-2-[1-(4-methoxy-2,3,6-trimethyl-phenylsulfonyl)-pyrrolidin-3-yloxy]-ethanone
8    1-(4-benzyl-4-hydroxy-piperidin-1-yl)-2-[1-(4-methoxy-2,3,6-trimethyl-phenylsulfonyl)-piperidin-4-yloxy]-ethanone
9    N-{2-[2-(4-benzyl-4-hydroxy-piperidin-1-yl)-2-oxo-ethoxy]-ethyl}-2,4,6-trichloro-N-methyl-phenylsulfonamide
10    2,6-dichloro-N-{2-[2-(4'-hydroxy-3',4',5',6'-tetrahydro-2'H-[2,4']bipyridinyl-1'-yl)-2-oxo-ethoxy]-ethyl}-N-methyl-phenylsulfonamide
11    1-(4-benzyl-4-hydroxy-piperidin-1-yl)-2-[1-(4-methoxy-2,3,6-trimethyl-phenylsulfonyl)-piperidin-3-yloxy]-ethanone
12    2-[1-(3,4-dichloro-phenylsulfonyl)-piperidin-2-ylmethoxy]-1-(4'-hydroxy-3',4',5',6'-tetrahydro-2'H-[3,4']bipyridinyl-1'-yl)-ethanone
13    N-benzyl-N-{2-[2-(4-benzyl-4-hydroxy-piperidin-1-yl)-2-oxo-ethoxy]-ethyl}-4-methoxy-2,3,6-trimethyl-phenylsulfonamide
14    1-(4-benzyl-4-hydroxy-piperidin-1-yl)-2-{2-[1-(4-methoxy-2,3,6-trimethyl-phenylsulfonyl)-piperidin-4-yl]-ethoxy}-ethanone
15    1-(4-benzyl-4-hydroxy-piperidin-1-yl)-2-[1-(4-fluoro-phenylsulfonyl)-pyrrolidin-3-yloxy]-ethanone
16    N-{2-[2-(4-benzyl-4-hydroxy-piperidin-1-yl)-2-oxo-ethoxy]-ethyl}-3,4-dimethoxy-N-methyl-phenylsulfonamide
17    2-[1-(2,4-dichloro-phenylsulfonyl)-pyrrolidin-3-yloxy]-1-(4'-hydroxy-3',4',5',6'-tetrahydro-2'H-[2,4']bipyridinyl-1'-yl)-ethanone
18    1-(4-benzyl-4-hydroxy-piperidin-1-yl)-2-{2-[4-(4-methoxy-2,3,6-trimethyl-phenylsulfonyl)-piperazin-1-yl]-ethoxy}-ethanone
19    2-[1-(3,4-dichloro-phenylsulfonyl)-pyrrolidin-2-ylmethoxy]-1-(4'-hydroxy-3',4',5',6'-tetrahydro-2'H-[3,4']bipyridinyl-1'-yl)-ethanone
20    N-{2-[2-(4'-hydroxy-3',4',5',6'-tetrahydro-2'H-[2,4']bipyridinyl-1'-yl)-2-oxo-ethoxy]-ethyl}-N-methyl-4-trifluoromethoxy-phenylsulfonamide
21    1-(4'-hydroxy-3',4',5',6'-tetrahydro-2'H-[2,4']bipyridinyl-1'-yl)-2-[1-(4-methoxy-2,6-dimethyl-phenylsulfonyl)-pyrrolidin-3-yloxy]-ethanone
22    2-(1-phenylsulfonyl-pyrrolidin-3-yloxy)-1-(4-benzyl-4-hydroxy-piperidin-1-yl)-ethanone
23    1-(4-benzyl-4-hydroxy-piperidin-1-yl)-2-[2-(4-methoxy-phenylsulfonyl)-1,2,3,4-tetrahydro-isoquinolin-3-ylmethoxy]-ethanone
24    1-(4-benzyl-4-hydroxy-piperidin-1-yl)-2-[1-(toluene-4-sulfonyl)-pyrrolidin-3-yloxy]-ethanone
25    2-[1-(3,4-dichloro-phenylsulfonyl)-piperidin-2-ylmethoxy]-1-(4'-hydroxy-3',4',5',6'-tetrahydro-2'H-[2,4']bipyridinyl-1'-yl)-ethanone
26    1-(4-hydroxy-3,4,5,6-tetrahydro-2H-[4,4']bipyridinyl-1-yl)-2-[1-(4-methoxy-phenylsulfonyl)-pyrrolidin-2-ylmethoxy]-ethanone
27    2-(1-phenylsulfonyl-piperidin-3-yloxy)-1-(4-benzyl-4-hydroxy-piperidin-1-yl)-ethanone
28    N-{2-[2-(4-benzyl-4-hydroxy-piperidin-1-yl)-2-oxo-ethoxy]-ethyl}-4-methoxy-N-methyl-phenylsulfonamide
29    1-(4-benzyl-4-hydroxy-piperidin-1-yl)-2-{2-[1-(4-methoxy-phenylsulfonyl)-piperidin-2-yl]-ethoxy}-ethanone
30    1-(4'-hydroxy-3',4',5',6'-tetrahydro-2'H-[2,4']bipyridinyl-1'-yl)-2-[1-(2,4,6-trimethyl-phenylsulfonyl)-pyrrolidin-3-yloxy]-ethanone 31 1-(4-benzyl-4-hydroxy-piperidin-1-yl)-2-[1-(4-chloro-phenylsulfonyl)-pyrrolidin-3-yloxy]-ethanone
32 2-[2-(4-phenylsulfonyl-piperazin-1-yl)-ethoxy]-1-(4-benzyl-4-hydroxy-piperidin-1-yl)-ethanone
33 N-{2-[2-(4-benzyl-4-hydroxy-piperidin-1-yl)-2-oxo-ethoxy]-phenyl}-3,4-dichloro-N-methyl-phenylsulfonamide
34 2-(1-phenylsulfonyl-pyrrolidin-3-yloxy)-1-(4'-hydroxy-3',4',5',6'-tetrahydro-2'H-[2,4']bipyridinyl-1'-yl)-ethanone
35 1-(4-benzyl-4-hydroxy-piperidin-1-yl)-2-[1-(4-methoxy-phenylsulfonyl)-piperidin-2-ylmethoxy]-ethanone
36 2-[1-(3,4-dichloro-phenylsulfonyl)-pyrrolidin-2-yl-methoxy]-1-(4'-hydroxy-3',4',5',6'-tetrahydro-2'H-[2,4']bipyridinyl-1'-yl)-ethanone
37 2-(1-phenylsulfonyl-piperidin-4-yloxy)-1-(4-benzyl-4-hydroxy-piperidin-1-yl)-ethanone
38 N-{2-[2-(4-benzyl-4-hydroxy-piperidin-1-yl)-2-oxo-ethoxy]-ethyl}-N-methyl-3-trifluoromethyl-phenylsulfonamide
39 N-{2-[2-(4-benzyl-4-hydroxy-piperidin-1-yl)-2-oxo-ethoxy]-ethyl}-N-methyl-phenylsulfonamide
40 1-(4'-hydroxy-3',4',5',6'-tetrahydro-2'H-[2,4']bipyridinyl-1'-yl)-2-[1-(4-methoxy-phenylsulfonyl)-pyrrolidin-2-yl-methoxy]-ethanone
41 N-{2-[2-(4'-hydroxy-3',4',5',6'-tetrahydro-2'H-[2,4']bipyridinyl-1'-yl)-2-oxo-ethoxy]-ethyl}-3,4-dimethoxy-N-methyl-phenylsulfonamide
42 N-{2-[2-(4'-hydroxy-3',4',5',6'-tetrahydro-2'H-[2,4']bipyridinyl-1'-yl)-2-oxo-ethoxy]-ethyl}-4-methoxy-N-methyl-phenylsulfonamide
43 N-{2-[2-(4-benzyl-4-hydroxy-piperidin-1-yl)-2-oxo-ethoxy]-cyclohexyl}-3,4-dichloro-N-methyl-phenylsulfonamide
44 1-(4'-hydroxy-3',4',5',6'-tetrahydro-2'H-[2,4']bipyridinyl-1'-yl)-2-{2-[1-(4-methoxy-phenylsulfonyl)-piperidin-2-yl]-ethoxy}-ethanone
45 1-(4'-hydroxy-3',4',5',6'-tetrahydro-2'H-[2,4']bipyridinyl-1'-yl)-2-{2-[1-(4-methoxy-2,3,6-trimethyl-phenylsulfonyl)-piperidin-4-yl]-ethoxy}-ethanone
46 2-(1-phenylsulfonyl-piperidin-4-yloxy)-1-(4'-hydroxy-3',4',5',6'-tetrahydro-2'H-[3,4']bipyridinyl-1'-yl)-ethanone
47 1-(4'-hydroxy-3',4',5',6'-tetrahydro-2'H-[3,4']bipyridinyl-1'-yl)-2-{2-[4-(4-methoxy-2,3,6-trimethyl-phenylsulfonyl)-piperazin-1-yl]-ethoxy}-ethanone
48 1-(4'-hydroxy-3',4',5',6'-tetrahydro-2'H-[2,4']bipyridinyl-1'-yl)-2-{2-[4-(4-methoxy-2,3,6-trimethyl-phenylsulfonyl)-piperazin-1-yl]-ethoxy}-ethanone
49 2-[2-(4-phenylsulfonyl-piperazin-1-yl)-ethoxy]-1-(4-hydroxy-3,4,5,6-tetrahydro-2H-[4,4']bipyridinyl-1-yl)-ethanone
50 1-(4'-hydroxy-3',4',5',6'-tetrahydro-2'H-[2,4']bipyridinyl-1'-yl)-2-[2-(4-methoxy-phenylsulfonyl)-1,2,3,4-tetrahydro-isoquinolin-3-ylmethoxy]-ethanone
51 2-(1-phenylsulfonyl-piperidin-3-yloxy)-1-(4'-hydroxy-3',4',5',6'-tetrahydro-2'H-[2,4']bipyridinyl-1'-yl)-ethanone
52 2-[1-(3,4-dimethoxy-phenylsulfonyl)-pyrrolidin-3-yloxy]-1-(4'-hydroxy-3',4',5',6'-tetrahydro-2'H-[2,4']bipyridinyl-1'-yl)-ethanone
53 1-(4-benzyl-4-hydroxy-piperidin-1-yl)-2-[1-(4-chloro-phenylsulfonyl)-piperidin-2-ylmethoxy]-ethanone
54 2-(1-phenylsulfonyl-piperidin-4-yloxy)-1-(4'-hydroxy-3',4',5',6'-tetrahydro-2'H-[2,4']bipyridinyl-1'-yl)-ethanone
55 1-(4'-hydroxy-3',4',5',6'-tetrahydro-2'H-[2,4']bipyridinyl-1'-yl)-2-[1-(4-methoxy-2,3,6-trimethyl-phenylsulfonyl)-piperidin-3-yloxy]-ethanone
56 4-fluoro-N-{2-[2-(4'-hydroxy-3',4',5',6'-tetrahydro-2'H-[2,4']bipyridinyl-1'-yl)-2-oxo-ethoxy]-ethyl}-N-methyl-phenylsulfonamide
57 1-(4-benzyl-4-hydroxy-piperidin-1-yl)-2-[1-(4-methoxy-phenylsulfonyl)-pyrrolidin-2-ylmethoxy]-ethanone
58 2-[1-(4-fluoro-phenylsulfonyl)-pyrrolidin-3-yloxy]-1-(4'-hydroxy-3',4',5',6'-tetrahydro-2'H-[2,4']bipyridinyl-1'-yl)-ethanone
59 1-(4'-hydroxy-3',4',5',6'-tetrahydro-2'H-[2,4']bipyridinyl-1'-yl)-2-[1-(3-trifluoromethyl-phenylsulfonyl)-pyrrolidin-3-yloxy]-ethanone
60 1-(4-benzyl-4-hydroxy-piperidin-1-yl)-2-[1-(2,4-dimethoxy-phenylsulfonyl)-piperidin-2-ylmethoxy]-ethanone
61 N-(2-(2-(4-(4-chlorophenyl)-4-hydroxypiperidin-1-yl)-2-oxoethoxy)ethyl)-5-fluoro-N,2-dimethylphenylsulfonamide
62 N-{2-[2-(4-benzyl-4-hydroxy-piperidin-1-yl)-2-oxo-ethoxy]-ethyl}-5-fluoro-2,N-dimethyl-phenylsulfonamide
63 1-(4-(4-chlorophenyl)-4-hydroxypiperidin-1-yl)-2-((1-(naphthalen-1-ylsulfonyl)piperidin-2-yl)methoxy)ethanone
64 1-(4-benzyl-4-hydroxy-piperidin-1-yl)-2-[1-(naphthalene-1-sulfonyl)-piperidin-2-ylmethoxy]-ethanone
65 1-(4-benzyl-4-hydroxy-piperidin-1-yl)-2-[1-(3-trifluoromethyl-phenylsulfonyl)-piperidin-2-ylmethoxy]-ethanone
66 1-(4-(4-chlorophenyl)-4-hydroxypiperidin-1-yl)-2-((1-(mesitylsulfonyl)piperidin-2-yl)methoxy)ethanone
67 1-(4-benzyl-4-hydroxy-piperidin-1-yl)-2-[1-(2,4,6-trimethyl-phenylsulfonyl)-piperidin-2-ylmethoxy]-ethanone
68 1-(4'-hydroxy-3',4',5',6'-tetrahydro-2'H-[3,4']bipyridinyl-1'-yl)-2-[1-(2,4,6-trimethyl-phenylsulfonyl)-piperidin-2-ylmethoxy]-ethanone
69 N-benzyl-N-{2-[2-(4-benzyl-4-hydroxy-piperidin-1-yl)-2-oxo-ethoxymethyl]-thiophen-3-yl}-3,4-dichloro-phenylsulfonamide
70 3,5-difluoro-N-{2-[2-(4'-hydroxy-3',4',5',6'-tetrahydro-2'H-[2,4']bipyridinyl-1'-yl)-2-oxo-ethoxy]-ethyl}-N-methyl-phenylsulfonamide
71 2,5-difluoro-N-{2-[2-(4'-hydroxy-3',4',5',6'-tetrahydro-2'H-[2,4']bipyridinyl-1'-yl)-2-oxo-ethoxy]-ethyl}-N-methyl-phenylsulfonamide
72 2-[2-(4-fluoro-phenylsulfonyl)-1,2,3,4-tetrahydro-isoquinolin-3-ylmethoxy]-1-(4'-hydroxy-3',4',5',6'-tetrahydro-2'H-[2,4']bipyridinyl-1'-yl)-ethanone
73 2-(2-phenylsulfonyl-1,2,3,4-tetrahydro-isoquinolin-3-ylmethoxy)-1-(4'-hydroxy-3',4',5',6'-tetrahydro-2'H-[2,4']bipyridinyl-1'-yl)-ethanone
74 1-(4'-hydroxy-3',4',5',6'-tetrahydro-2'H-[2,4']bipyridinyl-1'-yl)-2-[1-(4-methoxy-phenylsulfonyl)-4-phenyl-piperidin-4-yloxy]-ethanone
75 1-(4-benzyl-4-hydroxy-piperidin-1-yl)-2-[2-(4-fluoro-phenylsulfonyl)-1,2,3,4-tetrahydro-isoquinolin-3-ylmethoxy]-ethanone
76 2-((2-(3,4-dichlorophenylsulfonyl)-1,2,3,4-tetrahydroisoquinolin-3-yl)methoxy)-1-(4-hydroxy-4-phenylpiperidin-1-yl)ethanone
77 2-(2-phenylsulfonyl-1,2,3,4-tetrahydro-isoquinolin-3-ylmethoxy)-1-(4-benzyl-4-hydroxy-piperidin-1-yl)-ethanone
78 2-((2-(3,4-dichlorophenylsulfonyl)-1,2,3,4-tetrahydroisoquinolin-3-yl)methoxy)-1-(4-hydroxy-4-phenylpiperidin-1-yl)ethanone 79 1-(4-(4-chlorophenyl)-4-hydroxypiperidin-1-yl)-2-((2-(2,4-dichlorophenylsulfonyl)-1,2,3,4-tetrahydroisoquinolin-3-yl)methoxy)ethanone 80 2-((2-(2,4-dichlorophenylsulfonyl)-1,2,3,4-tetrahydroisoquinolin-3-yl)methoxy)-1-(4-hydroxy-4-phenylpiperidin-1-yl)ethanone 81 1-(4-benzyl-4-hydroxy-piperidin-1-yl)-2-[2-(2,4-dichloro-phenylsulfonyl)-1,2,3,4-tetrahydro-isoquinolin-3-ylmethoxy]-ethanone 82 1-(4-benzyl-4-hydroxy-piperidin-1-yl)-2-[1-(4-methoxy-phenylsulfonyl)-4-phenyl-piperidin-4-yloxy]-ethanone 83 N-benzyl-3,4-dichloro-N-(2-(2-(4-(4-chlorophenyl)-4-hydroxypiperidin-1-yl)-2-oxoethoxy)cyclohexyl)phenylsulfonamide 84 N-benzyl-N-{2-[2-(4-benzyl-4-hydroxy-piperidin-1-yl)-2-oxo-ethoxy]-cyclohexyl}-3,4-dichloro-phenylsulfonamide 85 1-(4-hydroxy-4-thiophen-2-yl-piperidin-1-yl)-2-[1-(4-methoxy-2,6-dimethyl-phenylsulfonyl)-piperidin-2-ylmethoxy]-ethanone 86 N-{2-[2-(4-hydroxy-4-thiophen-2-yl-piperidin-1-yl)-2-oxo-ethoxy]-ethyl}-4-methoxy-2,6,N-trimethyl-phenylsulfonamide 87 1-(4'-hydroxy-3',4',5',6'-tetrahydro-2'H-[3,4']bipyridinyl-1'-yl)-2-[1-(4-methoxy-2,6-dimethyl-phenylsulfonyl)-piperidin-2-ylmethoxy]-ethanone; hydrochloride 88 N-{2-[2-(4-hydroxy-3,4,5,6-tetrahydro-2H-[4,4']bipyridinyl-1'-yl)-2-oxo-ethoxy]-ethyl}-4-methoxy-2,6,N-trimethyl-phenylsulfonamide 89 1-(4'-hydroxy-3',4',5',6'-tetrahydro-2'H-[3,4']bipyridinyl-1'-yl)-2-[1-(4-methoxy-2,6-dimethyl-phenylsulfonyl)-pyrrolidin-2-ylmethoxy]-ethanone; hydrochloride 90 2-(2-phenylsulfonyl-1,2,3,4-tetrahydro-isoquinolin-3-ylmethoxy)-1-(4'-hydroxy-3',4',5',6'-tetrahydro-2'H-[3,4']bipyridinyl-1'-yl)-ethanone 91 2-[2-(3,4-dichloro-phenylsulfonyl)-1,2,3,4-tetrahydro-isoquinolin-3-ylmethoxy]-1-(4'-hydroxy-3',4',5',6'-tetrahydro-2'H-[3,4']bipyridinyl-1'-yl)-ethanone 92 2-[2-(2,4-dichloro-phenylsulfonyl)-1,2,3,4-tetrahydro-isoquinolin-3-ylmethoxy]-1-(4'-hydroxy-3',4',5',6'-tetrahydro-2'H-[3,4']bipyridinyl-1'-yl)-ethanone 93 N-(2-(2-(4-(4-chlorophenyl)-4-hydroxypiperidin-1-yl)-2-oxoethoxy)ethyl)-3,5-difluoro-N-methylphenylsulfonamide 94 1-(4'-hydroxy-3',4',5',6'-tetrahydro-2'H-[2,4']bipyridinyl-1'-yl)-2-[1-(2,4,6-trimethyl-phenylsulfonyl)-piperidin-2-ylmethoxy]-ethanone 95 N-benzyl-3,4-dichloro-N-{2-[2-(4'-hydroxy-3',4',5',6'-tetrahydro-2'H-[2,4']bipyridinyl-1'-yl)-2-oxo-ethoxy]-cyclohexyl}-phenylsulfonamide 96 1-(4'-hydroxy-3',4',5',6'-tetrahydro-2'H-[2,4']bipyridinyl-1'-yl)-2-[1-(3-trifluoromethyl-phenylsulfonyl)-piperidin-2-ylmethoxy]-ethanone 97 5-fluoro-N-{2-[2-(4'-hydroxy-3',4',5',6'-tetrahydro-2'H-[2,4']bipyridinyl-1'-yl)-2-oxo-ethoxy]-ethyl}-2,N-dimethyl-phenylsulfonamide 98 1-(4'-hydroxy-3',4',5',6'-tetrahydro-2'H-[2,4']bipyridinyl-1'-yl)-2-[1-(2,4,6-trichloro-phenylsulfonyl)-pyrrolidin-3-yloxy]-ethanone 99 1-(4-benzyl-4-hydroxy-piperidin-1-yl)-2-[1-(3,4-dichloro-phenylsulfonyl)-2,3-dihydro-1H-indol-2-ylmethoxy]-ethanone 100 2-[1-(3,4-dichloro-phenylsulfonyl)-2,3-dihydro-1H-indol-2-ylmethoxy]-1-(4'-hydroxy-3',4',5',6'-tetrahydro-2'H-[3,4']bipyridinyl-1'-yl)-ethanone 101 1-(4-hydroxy-4-phenylpiperidin-1-yl)-2-((2-(mesitylsulfonyl)-1,2,3,4-tetrahydroisoquinolin-3-yl)methoxy)ethanone 102 5-chloro-thiophene-2-sulfonic acid {2-[2-(4'-hydroxy-3',4',5',6'-tetrahydro-2'H-[3,4']bipyridinyl-1'-yl)-2-oxo-ethoxy]-ethyl}-methyl-amide 103 5-chloro-thiophene-2-sulfonic acid {2-[2-(4'-hydroxy-3',4',5',6'-tetrahydro-2'H-[2,4']bipyridinyl-1'-yl)-2-oxo-ethoxy]-ethyl}-methyl-amide 104 2,4-dichloro-N-(2-(2-(4-(4-chlorophenyl)-4-hydroxypiperidin-1-yl)-2-oxoethoxy)ethyl)-N,6-dimethylphenylsulfonamide 105 2,4-dichloro-N-(2-(2-(4-hydroxy-4-phenylpiperidin-1-yl)-2-oxoethoxy)ethyl)-N,6-dimethylphenylsulfonamide 106 N-{2-[2-(4-benzyl-4-hydroxy-piperidin-1-yl)-2-oxo-ethoxy]-ethyl}-2,4-dichloro-6,N-dimethyl-phenylsulfonamide 107 1-(4-(4-chlorophenyl)-4-hydroxypiperidin-1-yl)-2-(1-(2,4,6-trichlorophenylsulfonyl)pyrrolidin-3-yloxy)ethanone 108 1-(4-hydroxy-4-phenylpiperidin-1-yl)-2-(1-(2,4,6-trichlorophenylsulfonyl)pyrrolidin-3-yloxy)ethanone 109 1-(4-benzyl-4-hydroxy-piperidin-1-yl)-2-[1-(2,4,6-trichloro-phenylsulfonyl)-pyrrolidin-3-yloxy]-ethanone 111 3-(1-(4-chloro-2,5-dimethylphenylsulfonyl)piperidin-2-yl)-1-(4-hydroxy-4-(pyridin-3-yl)piperidin-1-yl)propan-1-one hydrochloride 112 1-(4-hydroxy-4-(pyridin-3-yl)piperidin-1-yl)-3-(1-(4-methoxy-2,6-dimethylphenylsulfonyl)piperidin-2-yl)propan-1-one 113 4-chloro-N-(4-(4-hydroxy-4-(pyridin-3-yl)piperidin-1-yl)-4-oxobutyl)-N,2,5-trimethylphenylsulfonamide hydrochloride 114 N-(4-(4-hydroxy-4-(pyridin-3-yl)piperidin-1-yl)-4-oxobutyl)-4-methoxy-N,2,6-trimethylphenylsulfonamide 115 N-(4-(4-hydroxy-4-(pyridin-3-yl)piperidin-1-yl)-4-oxobutyl)-N-methylnaphthalene-2-sulfonamide 116 2,4-dichloro-N-(4-(4-hydroxy-4-(pyridin-3-yl)piperidin-1-yl)-4-oxobutyl)-N-methylphenylsulfonamide 117 1-(4-hydroxy-4-(pyridin-3-yl)piperidin-1-yl)-3-(1-(naphthalen-2-ylsulfonyl)piperidin-2-yl)propan-1-one 118 3-(1-(2,4-dichlorophenylsulfonyl)piperidin-2-yl)-1-(4-hydroxy-4-(pyridin-3-yl)piperidin-1-yl)propan-1-one 119 3-(1-(4-chloro-2,5-dimethylphenylsulfonyl)piperidin-2-yl)-1-(4-hydroxy-4-(pyridin-2-yl)piperidin-1-yl)propan-1-one 120 3-(1-(4-chloro-2,5-dimethylphenylsulfonyl)piperidin-2-yl)-1-(4-(3-fluorophenyl)-4-hydroxypiperidin-1-yl)propan-1-one 121 N-(5-(4-hydroxy-4-(pyridin-3-yl)piperidin-1-yl)-5-oxopentyl)-4-methoxy-N,2,6-trimethylphenylsulfonamide 122 3-(1-(4-chloro-2,5-dimethylphenylsulfonyl)piperidin-2-yl)-1-(4-hydroxy-4-(pyridin-3-yl)piperidin-1-yl)propan-1-one 123 1-(4-(4-bromophenyl)-4-hydroxypiperidin-1-yl)-3-(1-(3-(trifluoromethyl)phenylsulfonyl)piperidin-2-yl)propan-1-one 124 3,4-dichloro-N-(2-(3-(4-(4-chloro-3-(trifluoromethyl)phenyl)-4-hydroxypiperidin-1-yl)-3-oxopropyl)phenyl)-N-methylphenylsulfonamide 125 3,4-dichloro-N-(2-(3-(4-hydroxy-4-(pyridin-3-yl)piperidin-1-yl)-3-oxopropyl)phenyl)-N-methylphenylsulfonamide 127 1-(4-hydroxy-4-(pyridin-3-yl)piperidin-1-yl)-2-((1-(4-methoxy-2,6-dimethylphenylsulfonyl)piperidin-2-yl)methoxy)ethanone 128 (S)-1-(4-hydroxy-4-(pyridin-3-yl)piperidin-1-yl)-2-((2-(4-methoxy-2,6-dimethylphenylsulfonyl)-1,2,3,4-tetrahydroisoquinolin-3-yl)methoxy)ethanone 129 (S)-2-((2-(2,4-dichlorophenylsulfonyl)-1,2,3,4-tetrahydroisoquinolin-3-yl)methoxy)-1-(4-hydroxy-4-(pyridin-3-yl)piperidin-1-yl)ethanone 130 N-benzyl-N-(2-(2-(4-hydroxy-4-(pyridin-3-yl)piperidin-1-yl)-2-oxoethoxy)ethyl)-4-methoxy-2,6-dimethylphenylsulfonamide 131 2-((2-(2,4-dichlorophenylsulfonyl)-1,2,3,4-tetrahydroisoquinolin-3-yl)methoxy)-1-(4-hydroxy-4-(pyridin-3-yl)piperidin-1-yl)ethanone hydrochloride 132 N-(2-(2-(4-hydroxy-4-(3-(trifluoromethyl)phenyl)piperidin-1-yl)-2-oxoethoxy)ethyl)-4-methoxy-N,2,6-trimethylphenylsulfonamide 133 N-(2-(3-(4-hydroxy-4-(pyridin-3-yl)piperidin-1-yl)-3-oxopropoxy)ethyl)-4-methoxy-N,2,6-trimethylphenylsulfonamide 134 (S)-1-(4-hydroxy-4-(pyridin-3-yl)piperidin-1-yl)-2-((2-(4-methoxyphenylsulfonyl)-1,2,3,4-tetrahydroisoquinolin-3-yl)methoxy)ethanone 135 2-((1-(2,4-dichlorophenylsulfonyl)indolin-2-yl)methoxy)-1-(4-hydroxy-4-(pyridin-3-yl)piperidin-1-yl)ethanone 136 N-(2-(2-(4-(4-chlorophenyl)-4-hydroxypiperidin-1-yl)-2-oxoethoxy)ethyl)-4-methoxy-N,2,6-trimethylphenylsulfonamide 137 N-(2-(2-(4-hydroxy-4-phenylpiperidin-1-yl)-2-oxoethoxy)ethyl)-4-methoxy-N,2,6-trimethylphenylsulfonamide 138 1-(4-hydroxy-4-(pyridin-2-yl)piperidin-1-yl)-2-((1-(4-methoxy-2,6-dimethylphenylsulfonyl)piperidin-2-yl)methoxy)ethanone 139 N-cyclopropyl-N-(2-(2-(4-hydroxy-4-(pyridin-3-yl)piperidin-1-yl)-2-oxoethoxy)ethyl)-4-methoxy-2,6-dimethylphenylsulfonamide 140 N-(2-(2-(4-hydroxy-4-(2-(pyridin-3-yl)ethyl)piperidin-1-yl)-2-oxoethoxy)ethyl)-4-methoxy-N,2,6-trimethylphenylsulfonamide 141 N-(2-(2-(4-(3-fluorophenyl)-4-hydroxypiperidin-1-yl)-2-oxoethoxy)ethyl)-4-methoxy-N,2,6-trimethylphenylsulfonamide 142 1-(4-(3-fluorophenyl)-4-hydroxypiperidin-1-yl)-2-((1-(4-methoxy-2,6-dimethylphenylsulfonyl)piperidin-2-yl)methoxy)ethanone 143 N-(2-(2-(4-hydroxy-4-(pyridin-3-yl)piperidin-1-yl)-2-oxoethoxy)ethyl)-4-methoxy-N,2,6-trimethylphenylsulfonamide 144 1-(4-hydroxy-4-(pyridin-4-yl)piperidin-1-yl)-2-((1-(4-methoxy-2,6-dimethylphenylsulfonyl)piperidin-2-yl)methoxy)ethanone 145 2-((1-(3,4-dichlorophenylsulfonyl)-1,2,3,4-tetrahydroquinolin-2-yl)methoxy)-1-(4-(3-fluorophenyl)-4-hydroxypiperidin-1-yl)ethanone 146 2-((1-(3,4-dichlorophenylsulfonyl)-1,2,3,4-tetrahydroquinolin-2-yl)methoxy)-1-(4-hydroxy-4-(pyridin-2-yl)piperidin-1-yl)ethanone 147 2-((1-(3,4-dichlorophenylsulfonyl)-1,2,3,4-tetrahydroquinolin-2-yl)methoxy)-1-(4-hydroxy-4-(pyridin-4-yl)piperidin-1-yl)ethanone 148 N-(2-(2-(4-hydroxy-4-(pyridin-3-yl)piperidin-1-yl)-2-oxoethoxy)ethyl)-N,2-dimethylnaphthalene-1-sulfonamide 149 4-chloro-N-(2-(2-(4-hydroxy-4-(pyridin-3-yl)piperidin-1-yl)-2-oxoethoxy)ethyl)-N,2,5-trimethylphenylsulfonamide 150 4-chloro-N-(2-(2-(4-(4-chlorophenyl)-4-hydroxypiperidin-1-yl)-2-oxoethoxy)ethyl)-N,2,5-trimethylphenylsulfonamide 151 N-(2-(2-(4-(4-bromophenyl)-4-hydroxypiperidin-1-yl)-2-oxoethoxy)ethyl)-4-chloro-N,2,5-trimethylphenylsulfonamide 152 4-chloro-N-(2-(2-(4-hydroxy-4-phenylpiperidin-1-yl)-2-oxoethoxy)ethyl)-N,2,5-trimethylphenylsulfonamide 153 N-(2-(2-(4-benzyl-4-hydroxypiperidin-1-yl)-2-oxoethoxy)ethyl)-4-chloro-N,2,5-trimethylphenylsulfonamide 154 4-chloro-N-(2-(2-(4-hydroxy-4-(3-(trifluoromethyl)phenyl)piperidin-1-yl)-2-oxoethoxy)ethyl)-N,2,5-trimethylphenylsulfonamide 155 1-(4-hydroxy-4-(pyridin-3-yl)piperidin-1-yl)-2-((1-(4-(trifluoromethyl)phenylsulfonyl)piperidin-2-yl)methoxy)ethanone 156 1-(4-(4-chlorophenyl)-4-hydroxypiperidin-1-yl)-2-((1-(4-(trifluoromethyl)phenylsulfonyl)piperidin-2-yl)methoxy)ethanone 157 2-((1-(4-chloro-2,5-dimethylphenylsulfonyl)piperidin-2-yl)methoxy)-1-(4-hydroxy-4-(pyridin-3-yl)piperidin-1-yl)ethanone 158 2-((1-(4-chloro-2,5-dimethylphenylsulfonyl)piperidin-2-yl)methoxy)-1-(4-hydroxy-4-phenylpiperidin-1-yl)ethanone 159 1-(4-benzyl-4-hydroxypiperidin-1-yl)-2-((1-(4-chloro-2,5-dimethylphenylsulfonyl)piperidin-2-yl)methoxy)ethanone 160 2-((1-(4-chloro-2,5-dimethylphenylsulfonyl)piperidin-2-yl)methoxy)-1-(4-(4-chloro-3-(trifluoromethyl)phenyl)-4-hydroxypiperidin-1-yl)ethanone 161 2-((1-(3-chloro-4-methylphenylsulfonyl)piperidin-2-yl)methoxy)-1-(4-hydroxy-4-(pyridin-3-yl)piperidin-1-yl)ethanone 162 2-((1-(2,6-dichloro-4-(trifluoromethyl)phenylsulfonyl)piperidin-2-yl)methoxy)-1-(4-hydroxy-4-phenylpiperidin-1-yl)ethanone 163 1-(4-benzyl-4-hydroxypiperidin-1-yl)-2-((1-(2,6-dichloro-4-(trifluoromethyl)phenylsulfonyl)piperidin-2-yl)methoxy)ethanone 164 2-((1-(2,6-dichloro-4-(trifluoromethyl)phenylsulfonyl)piperidin-2-yl)methoxy)-1-(4-hydroxy-4-(3-(trifluoromethyl)phenyl)piperidin-1-yl)ethanone 165 1-(4-(4-chloro-3-(trifluoromethyl)phenyl)-4-hydroxypiperidin-1-yl)-2-((1-(2,6-dichloro-4-(trifluoromethyl)phenylsulfonyl)piperidin-2-yl)methoxy)ethanone 166 1-(4-(4-chlorophenyl)-4-hydroxypiperidin-1-yl)-2-((1-(2,6-dichloro-4-(trifluoromethyl)phenylsulfonyl)pyrrolidin-2-yl)methoxy)ethanone 167 1-(4-(4-bromophenyl)-4-hydroxypiperidin-1-yl)-2-((1-(2,6-dichloro-4-(trifluoromethyl)phenylsulfonyl)pyrrolidin-2-yl)methoxy)ethanone 168 2-((1-(2,6-dichloro-4-(trifluoromethyl)phenylsulfonyl)pyrrolidin-2-yl)methoxy)-1-(4-hydroxy-4-phenylpiperidin-1-yl)ethanone 169 1-(4-benzyl-4-hydroxypiperidin-1-yl)-2-((1-(2,6-dichloro-4-(trifluoromethyl)phenylsulfonyl)pyrrolidin-2-yl)methoxy)ethanone 170 2-((1-(2,6-dichloro-4-(trifluoromethyl)phenylsulfonyl)pyrrolidin-2-yl)methoxy)-1-(4-hydroxy-4-(3-(trifluoromethyl)phenyl)piperidin-1-yl)ethanone 171 1-(4-(4-chloro-3-(trifluoromethyl)phenyl)-4-hydroxypiperidin-1-yl)-2-((1-(2,6-dichloro-4-(trifluoromethyl)phenylsulfonyl)pyrrolidin-2-yl)methoxy)ethanone 172 1-(4-hydroxy-4-(pyridin-3-yl)piperidin-1-yl)-2-((1-(2-(trifluoromethyl)phenylsulfonyl)piperidin-2-yl)methoxy)ethanone 173 1-(4-(4-chlorophenyl)-4-hydroxypiperidin-1-yl)-2-((1-(2-(trifluoromethyl)phenylsulfonyl)piperidin-2-yl)methoxy)ethanone
174 1-(4-(4-bromophenyl)-4-hydroxypiperidin-1-yl)-2-((1-(2-(trifluoromethyl)phenylsulfonyl)piperidin-2-yl)methoxy)ethanone
175 1-(4-hydroxy-4-phenylpiperidin-1-yl)-2-((1-(2-(trifluoromethyl)phenylsulfonyl)piperidin-2-yl)methoxy)ethanone
176 1-(4-benzyl-4-hydroxypiperidin-1-yl)-2-((1-(2-(trifluoromethyl)phenylsulfonyl)piperidin-2-yl)methoxy)ethanone
177 1-(4-hydroxy-4-(3-(trifluoromethyl)phenyl)piperidin-1-yl)-2-((1-(2-(trifluoromethyl)phenylsulfonyl)piperidin-2-yl)methoxy)ethanone
178 1-(4-(4-chloro-3-(trifluoromethyl)phenyl)-4-hydroxypiperidin-1-yl)-2-((1-(2-(trifluoromethyl)phenylsulfonyl)piperidin-2-yl)methoxy)ethanone
179 1-(4-benzyl-4-hydroxypiperidin-1-yl)-3-((1-(4-methoxy-2,6-dimethylphenylsulfonyl)piperidin-2-yl)methoxy)propan-1-one
180 1-(4-(4-chloro-3-(trifluoromethyl)phenyl)-4-hydroxypiperidin-1-yl)-3-((1-(4-methoxy-2,6-dimethylphenylsulfonyl)piperidin-2-yl)methoxy)propan-1-one
181 1-(4-(4-chlorophenyl)-4-hydroxypiperidin-1-yl)-3-((1-(4-methoxy-2,6-dimethylphenylsulfonyl)piperidin-2-yl)methoxy)propan-1-one
182 1-(4-(4-bromophenyl)-4-hydroxypiperidin-1-yl)-3-((1-(4-methoxy-2,6-dimethylphenylsulfonyl)piperidin-2-yl)methoxy)propan-1-one
183 1-(4-hydroxy-4-phenylpiperidin-1-yl)-3-((1-(4-methoxy-2,6-dimethylphenylsulfonyl)piperidin-2-yl)methoxy)propan-1-one
184 1-(4-(4-chlorophenyl)-4-hydroxypiperidin-1-yl)-3-(1-(4-methoxy-2,6-dimethylphenylsulfonyl)piperidin-3-yloxy)propan-1-one
185 1-(4-(4-bromophenyl)-4-hydroxypiperidin-1-yl)-3-(1-(4-methoxy-2,6-dimethylphenylsulfonyl)piperidin-3-yloxy)propan-1-one
186 1-(4-(4-chlorophenyl)-4-hydroxypiperidin-1-yl)-3-(1-(4-methoxy-2,6-dimethylphenylsulfonyl)pyrrolidin-3-yloxy)propan-1-one
187 1-(4-(4-bromophenyl)-4-hydroxypiperidin-1-yl)-3-(1-(4-methoxy-2,6-dimethylphenylsulfonyl)pyrrolidin-3-yloxy)propan-1-one
188 1-(4-hydroxy-4-phenylpiperidin-1-yl)-3-(1-(4-methoxy-2,6-dimethylphenylsulfonyl)pyrrolidin-3-yloxy)propan-1-one
189 1-(4-benzyl-4-hydroxypiperidin-1-yl)-3-(1-(4-methoxy-2,6-dimethylphenylsulfonyl)pyrrolidin-3-yloxy)propan-1-one
190 1-(4-hydroxy-4-(3-(trifluoromethyl)phenyl)piperidin-1-yl)-3-(1-(4-methoxy-2,6-dimethylphenylsulfonyl)pyrrolidin-3-yloxy)propan-1-one
191 N-benzyl-N-(2-(2-(4-benzyl-4-hydroxypiperidin-1-yl)-2-oxoethoxy)ethyl)-4-methoxy-2,3,6-trimethylphenylsulfonamide
192 1-(4-benzyl-4-hydroxypiperidin-1-yl)-2-(1-(4-methoxy-2,3,6-trimethylphenylsulfonyl)piperidin-3-yloxy)ethanone
193 1-(4-hydroxy-4-(pyridin-3-yl)piperidin-1-yl)-2-((1-(4-methoxy-2,6-dimethylphenylsulfonyl)pyrrolidin-2-yl)methoxy)ethanone
194 1-(4-hydroxy-4-(pyridin-3-yl)piperidin-1-yl)-2-((1-(4-methoxy-2,6-dimethylphenylsulfonyl)pyrrolidin-3-yl)methoxy)ethanone
195 1-(4-hydroxy-4-(pyridin-3-yl)piperidin-1-yl)-2-((2-(4-methoxy-2,3,6-trimethylphenylsulfonyl)-1,2,3,4-tetrahydroisoquinolin-3-yl)methoxy)ethanone
196 2-((1-(2,6-dichlorophenylsulfonyl)piperidin-2-yl)methoxy)-1-(4-hydroxy-4-(pyridin-3-yl)piperidin-1-yl)ethanone
197 2-((1-(2,6-dichlorophenylsulfonyl)pyrrolidin-2-yl)methoxy)-1-(4-hydroxy-4-(pyridin-3-yl)piperidin-1-yl)ethanone
198 2,4-dichloro-N-(2-(2-(4-hydroxy-4-(pyridin-2-yl)piperidin-1-yl)-2-oxoethoxy)ethyl)-N,6-dimethylphenylsulfonamide
199 2,4-dichloro-N-(2-(2-(4-hydroxy-4-(pyridin-3-yl)piperidin-1-yl)-2-oxoethoxy)ethyl)-N,5-dimethylphenylsulfonamide
200 1-(4-(4-chlorophenyl)-4-hydroxypiperidin-1-yl)-2-((2-(mesitylsulfonyl)-1,2,3,4-tetrahydroisoquinolin-3-yl)methoxy)ethanone
201 1-(4-benzyl-4-hydroxypiperidin-1-yl)-2-((2-(mesitylsulfonyl)-1,2,3,4-tetrahydroisoquinolin-3-yl)methoxy)ethanone
202 1-(4-(4-chlorophenyl)-4-hydroxypiperidin-1-yl)-2-((1-(4-methoxy-2,6-dimethylphenylsulfonyl)pyrrolidin-3-yl)methoxy)ethanone
203 2-((1-(2,5-dichlorothiophen-3-ylsulfonyl)pyrrolidin-2-yl)methoxy)-1-(4-hydroxy-4-(pyridin-3-yl)piperidin-1-yl)ethanone
204 1-(4-hydroxy-4-(pyridin-3-yl)piperidin-1-yl)-2-((1-(2,4,6-trichlorophenylsulfonyl)pyrrolidin-2-yl)methoxy)ethanone
205 N-(2-(2-(4-(4-bromophenyl)-4-hydroxypiperidin-1-yl)-2-oxoethoxy)ethyl)-N-(cyclopropylmethyl)-4-methoxy-2,3,6-trimethylphenylsulfonamide
206 N-(cyclopropylmethyl)-N-(2-(2-(4-hydroxy-4-phenylpiperidin-1-yl)-2-oxoethoxy)ethyl)-4-methoxy-2,3,6-trimethylphenylsulfonamide
207 N-(2-(2-(4-benzyl-4-hydroxypiperidin-1-yl)-2-oxoethoxy)ethyl)-N-(cyclopropylmethyl)-4-methoxy-2,3,6-trimethylphenylsulfonamide
208 N-(cyclopropylmethyl)-N-(2-(2-(4-hydroxy-4-(3-(trifluoromethyl)phenyl)-piperidin-1-yl)-2-oxoethoxy)ethyl)-4-methoxy-2,3,6-trimethylphenylsulfonamide
209 N-(2-(2-(4-(4-chlorophenyl)-4-hydroxypiperidin-1-yl)-2-oxoethoxy)ethyl)-N-isobutyl-4-methoxy-2,3,6-trimethylphenylsulfonamide
210 N-(2-(2-(4-(4-bromophenyl)-4-hydroxypiperidin-1-yl)-2-oxoethoxy)ethyl)-N-isobutyl-4-methoxy-2,3,6-trimethylphenylsulfonamide
211 N-(2-(2-(4-benzyl-4-hydroxypiperidin-1-yl)-2-oxoethoxy)ethyl)-N-isobutyl-4-methoxy-2,3,6-trimethylphenylsulfonamide
212 N-(2-(2-(4-hydroxy-4-(3-(trifluoromethyl)phenyl)piperidin-1-yl)-2-oxoethoxy)ethyl)-N-isobutyl-4-methoxy-2,3,6-trimethylphenylsulfonamide
213 1-(4-(4-chloro-3-(trifluormethyl)phenyl)-4-hydroxypiperidin-1-yl)-2-((1-(4-methoxy-2,6-dimethylphenylsulfonyl)pyrrolidin-2-yl)methoxy)ethanone
214 1-(4-(4-bromophenyl)-4-hydroxypiperidin-1-yl)-2-((1-(4-methoxy-2,6-dimethylphenylsulfonyl)pyrrolidin-2-yl)methoxy)ethanone
215 1-(4-hydroxy-4-phenylpiperidin-1-yl)-2-((1-(4-methoxy-2,6-dimethylphenylsulfonyl)pyrrolidin-2-yl)methoxy)ethanone
216 1-(4-benzyl-4-hydroxypiperidin-1-yl)-2-((1-(4-methoxy-2,6-dimethylphenylsulfonyl)pyrrolidin-2-yl)methoxy)ethanone 217 1-(4-hydroxy-4-(3-(trifluoromethyl)phenyl)piperidin-1-yl)-2-((1-(4-methoxy-2,6-dimethylphenylsulfonyl)pyrrolidin-2-yl)methoxy)ethanone
218 1-(4-(4-chloro-3-(trifluoromethyl)phenyl)-4-hydroxypiperidin-1-yl)-2-((1-(2,6-dichlorophenylsulfonyl)pyrrolidin-2-yl)methoxy)ethanone
219 1-(4-(4-bromophenyl)-4-hydroxypiperidin-1-yl)-2-((1-(2,6-dichlorophenylsulfonyl)pyrrolidin-2-yl)methoxy)ethanone
220 2-((1-(2,6-dichlorophenylsulfonyl)pyrrolidin-2-yl)methoxy)-1-(4-hydroxy-4-phenylpiperidin-1-yl)ethanone
221 1-(4-benzyl-4-hydroxypiperidin-1-yl)-2-((1-(2,6-dichlorophenylsulfonyl)pyrrolidin-2-yl)methoxy)ethanone
222 2-((1-(2,6-dichlorophenylsulfonyl)pyrrolidin-2-yl)methoxy)-1-(4-hydroxy-4-(3-(trifluoromethyl)phenyl)piperidin-1-yl)ethanone
223 1-(4-(4-chloro-3-(trifluoromethyl)phenyl)-4-hydroxypiperidin-1-yl)-2-((1-(2,5-dichlorothiophen-3-ylsulfonyl)pyrrolidin-2-yl)methoxy)ethanone
224 1-(4-(4-bromophenyl)-4-hydroxypiperidin-1-yl)-2-((1-(2,5-dichlorothiophen-3-ylsulfonyl)pyrrolidin-2-yl)methoxy)ethanone
225 2-((1-(2,5-dichlorothiophen-3-ylsulfonyl)pyrrolidin-2-yl)methoxy)-1-(4-hydroxy-4-phenylpiperidin-1-yl)ethanone
226 1-(4-benzyl-4-hydroxypiperidin-1-yl)-2-((1-(2,5-dichlorothiophen-3-ylsulfonyl)pyrrolidin-2-yl)methoxy)ethanone
227 2-((1-(2,5-dichlorothiophen-3-ylsulfonyl)pyrrolidin-2-yl)methoxy)-1-(4-hydroxy-4-(3-(trifluoromethyl)phenyl)piperidin-1-yl)ethanone
228 1-(4-(4-chloro-3-(trifluoromethyl)phenyl)-4-hydroxypiperidin-1-yl)-2-((1-(4-methoxy-2,6-dimethylphenylsulfonyl)pyrrolidin-3-yl)methoxy)ethanone
229 2-((1-(2,5-dichlorothiophen-3-ylsulfonyl)piperidin-2-yl)methoxy)-1-(4-hydroxy-4-(pyridin-3-yl)piperidin-1-yl)ethanone
230 1-(4-(4-bromophenyl)-4-hydroxypiperidin-1-yl)-2-((1-(4-methoxy-2,6-dimethylphenylsulfonyl)pyrrolidin-3-yl)methoxy)ethanone
231 1-(4-hydroxy-4-(3-(trifluoromethyl)phenyl)piperidin-1-yl)-2-((1-(4-methoxy-2,6-dimethylphenylsulfonyl)pyrrolidin-3-yl)methoxy)ethanone
232 1-(4-benzyl-4-hydroxypiperidin-1-yl)-2-((2-(4-methoxy-2,3,6-trimethylphenylsulfonyl)-1,2,3,4-tetrahydroisoquinolin-3-yl)methoxy)ethanone
233 1-(4-hydroxy-4-(3-(trifluoromethyl)phenyl)piperidin-1-yl)-2-((2-(4-methoxy-2,3,6-trimethylphenylsulfonyl)-1,2,3,4-tetrahydroisoquinolin-3-yl)methoxy)ethanone
234 1-(4-(4-bromophenyl)-4-hydroxypiperidin-1-yl)-2-((1-(2,6-dichlorophenylsulfonyl)piperidin-2-yl)methoxy)ethanone
235 2-((1-(2,6-dichlorophenylsulfonyl)piperidin-2-yl)methoxy)-1-(4-hydroxy-4-(3-(trifluoromethyl)phenyl)piperidin-1-yl)ethanone
236 1-(4-(4-chloro-3-(trifluoromethyl)phenyl)-4-hydroxypiperidin-1-yl)-2-((1-(2,6-dichlorophenylsulfonyl)piperidin-2-yl)methoxy)ethanone
237 N-(2-(2-(4-(4-chloro-3-(trifluoromethyl)phenyl)-4-hydroxypiperidin-1-yl)-2-oxoethoxy)ethyl)-N-(cyclopropylmethyl)-4-methoxy-2,3,6-trimethylphenyl-sulfonamide
238 N-(2-(2-(4-(4-chloro-3-(trifluoromethyl)phenyl)-4-hydroxypiperidin-1-yl)-2-oxoethoxy)ethyl)-N-isobutyl-4-methoxy-2,3,6-trimethylphenylsulfonamide
239 1-(4-hydroxy-4-(thiophen-2-yl)piperidin-1-yl)-2-((1-(4-methoxy-2,6-dimethylphenylsulfonyl)pyrrolidin-2-yl)methoxy)ethanone
240 N-(cyclopropylmethyl)-N-(2-(2-(4-hydroxy-4-(pyridin-3-yl)piperidin-1-yl)-2-oxoethoxy)ethyl)-4-methoxy-2,3,6-trimethylphenylsulfonamide
241 N-(2-(2-(4-hydroxy-4-(pyridin-3-yl)piperidin-1-yl)-2-oxoethoxy)ethyl)-N-isobutyl-4-methoxy-2,3,6-trimethylphenylsulfonamide
242 1-(4-(4-chlorophenyl)-4-hydroxypiperidin-1-yl)-2-((1-(4-methoxy-2,6-dimethylphenylsulfonyl)piperidin-2-yl)methoxy)ethanone
243 1-(4-(4-bromophenyl)-4-hydroxypiperidin-1-yl)-2-((1-(4-methoxy-2,6-dimethylphenylsulfonyl)piperidin-2-yl)methoxy)ethanone
244 1-(4-hydroxy-4-phenylpiperidin-1-yl)-2-((1-(4-methoxy-2,6-dimethylphenylsulfonyl)piperidin-2-yl)methoxy)ethanone
245 1-(4-benzyl-4-hydroxypiperidin-1-yl)-2-((1-(4-methoxy-2,6-dimethylphenylsulfonyl)piperidin-2-yl)methoxy)ethanone
246 1-(4-(4-chloro-3-(trifluoromethyl)phenyl)-4-hydroxypiperidin-1-yl)-2-((1-(4-methoxy-2,6-dimethylphenylsulfonyl)piperidin-2-yl)methoxy)ethanone
247 1-(4-(4-chloro-3-(trifluoromethyl)phenyl)-4-hydroxypiperidin-1-yl)-2-((1-(2,5-dichlorothiophen-3-ylsulfonyl)piperidin-2-yl)methoxy)ethanone
248 1-(4-benzyl-4-hydroxypiperidin-1-yl)-2-((1-(2,4,6-trichlorophenylsulfonyl)pyrrolidin-3-yl)methoxy)ethanone
249 1-(4-benzyl-4-hydroxypiperidin-1-yl)-2-(1-(2,4,6-trichlorophenylsulfonyl)piperidin-3-yloxy)ethanone
250 1-(4-(4-chloro-3-(trifluoromethyl)phenyl)-4-hydroxypiperidin-1-yl)-2-(1-(2,4,6-trichlorophenylsulfonyl)piperidin-3-yloxy)ethanone
251 1-(4-(4-chlorophenyl)-4-hydroxypiperidin-1-yl)-2-((1-(4-methoxy-2,6-dimethylphenylsulfonyl)piperidin-3-yl)methoxy)ethanone
252 1-(4-benzyl-4-hydroxypiperidin-1-yl)-2-((1-(4-methoxy-2,6-dimethylphenylsulfonyl)piperidin-3-yl)methoxy)ethanone
253 1-(4-(4-chloro-3-(trifluoromethyl)phenyl)-4-hydroxypiperidin-1-yl)-2-((1-(4-methoxy-2,6-dimethylphenylsulfonyl)piperidin-3-yl)methoxy)ethanone
254 1-(4-(4-chlorophenyl)-4-hydroxypiperidin-1-yl)-2-((1-(2,4,6-trichlorophenylsulfonyl)piperidin-3-yl)methoxy)ethanone
255 1-(4-hydroxy-4-phenylpiperidin-1-yl)-2-((1-(2,4,6-trichlorophenylsulfonyl)piperidin-3-yl)methoxy)ethanone
256 N-(2-(2-(4-(4-chlorophenyl)-4-hydroxypiperidin-1-yl)-2-oxoethoxy)ethyl)-N,2,5-trimethylthiophene-3-sulfonamide
257 N-(2-(2-(4-(4-bromophenyl)-4-hydroxypiperidin-1-yl)-2-oxoethoxy)ethyl)-N,2,5-trimethylthiophene-3-sulfonamide
258 N-(2-(2-(4-hydroxy-4-(3-(trifluoromethyl)phenyl)piperidin-1-yl)-2-oxoethoxy)ethyl)-N,2,5-trimethylthiophene-3-sulfonamide
259 N-(2-(2-(4-(4-chloro-3-(trifluoromethyl)phenyl)-4-hydroxypiperidin-1-yl)-2-oxoethoxy)ethyl)-N,2,5-trimethylthiophene-3-sulfonamide
260 2,5-dichloro-N-(2-(2-(4-(4-chlorophenyl)-4-hydroxypiperidin-1-yl)-2-oxoethoxy)ethyl)-N-methylthiophene-3-sulfonamide 261 N-(2-(2-(4-(4-bromophenyl)-4-hydroxypiperidin-1-yl)-2-oxoethoxy)ethyl)-2,5-dichloro-N-methylthiophene-3-sulfonamide
262 2,5-dichloro-N-(2-(2-(4-hydroxy-4-(3-(trifluoromethyl)phenyl)piperidin-1-yl)-2-oxoethoxy)ethyl)-N-methylthiophene-3-sulfonamide
263 2,5-dichloro-N-(2-(2-(4-(4-chloro-3-(trifluoromethyl)phenyl)-4-hydroxypiperidin-1-yl)-2-oxoethoxy)ethyl)-N-methylthiophene-3-sulfonamide
264 1-(4-(4-bromophenyl)-4-hydroxypiperidin-1-yl)-2-(1-(2-methoxy-4,6-dimethylphenylsulfonyl)pyrrolidin-3-yloxy)ethanone
265 1-(4-benzyl-4-hydroxypiperidin-1-yl)-2-(1-(2-methoxy-4,6-dimethylphenylsulfonyl)pyrrolidin-3-yloxy)ethanone
266 2-((1-(2,5-dichlorothiophen-3-ylsulfonyl)pyrrolidin-2-yl)methoxy)-1-(4-hydroxy-4-(thiophen-2-yl)piperidin-1-yl)ethanone
267 1-(4-hydroxy-4-(thiophen-2-yl)piperidin-1-yl)-2-((1-(4-methoxy-2,6-dimethylphenylsulfonyl)pyrrolidin-3-yl)methoxy)ethanone
268 N-(cyclopropylmethyl)-N-(2-(2-(4-hydroxy-4-(thiophen-2-yl)piperidin-1-yl)-2-oxoethoxy)ethyl)-4-methoxy-2,3,6-trimethylphenylsulfonamide
269 N-(2-(2-(4-hydroxy-4-(thiophen-2-yl)piperidin-1-yl)-2-oxoethoxy)ethyl)-N-isobutyl-4-methoxy-2,3,6-trimethylphenylsulfonamide
270 2-((1-(2,6-dichlorophenylsulfonyl)piperidin-2-yl)methoxy)-1-(4-hydroxy-4-(thiophen-2-yl)piperidin-1-yl)ethanone
271 2-((1-(2,5-dichlorothiophen-3-ylsulfonyl)piperidin-2-yl)methoxy)-1-(4-hydroxy-4-phenylpiperidin-1-yl)ethanone
272 1-(4-(4-chlorophenyl)-4-hydroxypiperidin-1-yl)-2-((1-(2,4,6-trichlorophenylsulfonyl)pyrrolidin-3-yl)methoxy)ethanone
273 2-((1-(benzo[b]thiophen-3-ylsulfonyl)piperidin-2-yl)methoxy)-1-(4-hydroxy-4-(pyridin-3-yl)piperidin-1-yl)ethanone
274 2-((1-(benzo[b]thiophen-3-ylsulfonyl)piperidin-2-yl)methoxy)-1-(4-benzyl-4-hydroxypiperidin-1-yl)ethanone
275 N-(2-(3-(4-(4-chlorophenyl)-4-hydroxypiperidin-1-yl)-3-oxopropoxy)ethyl)-4-methoxy-N,2,6-trimethylphenylsulfonamide
276 N-(2-(3-(4-hydroxy-4-phenylpiperidin-1-yl)-3-oxopropoxy)ethyl)-4-methoxy-N,2,6-trimethylphenylsulfonamide
277 N-(2-(3-(4-benzyl-4-hydroxypiperidin-1-yl)-3-oxopropoxy)ethyl)-4-methoxy-N,2,6-trimethylphenylsulfonamide
278 N-(2-(3-(4-(4-chloro-3-(trifluoromethyl)phenyl)-4-hydroxypiperidin-1-yl)-3-oxopropoxy)ethyl)-4-methoxy-N,2,6-trimethylphenylsulfonamide
279 N-(2-(2-(4-hydroxy-4-(pyridin-3-ylmethyl)piperidin-1-yl)-2-oxoethoxy)ethyl)-4-methoxy-N,2,6-trimethylphenylsulfonamide hydrochloride
280 N-(2-(2-(4-hydroxy-4-(pyridin-4-ylmethyl)piperidin-1-yl)-2-oxoethoxy)ethyl)-4-methoxy-N,2,6-trimethylphenylsulfonamide The numbering used above for the individual substances according to the invention is retained in the following explanations of the present invention, including in the description of the examples.

The compounds according to the invention relate to B1R modulators. Compounds that bind both to the rat receptor and to the human receptor are particularly advantageous in this connection.

The compounds according to the invention preferably exhibit an antagonistic action on the human B1R receptor or the B1R receptor of the rat. In a preferred embodiment of the invention, the substances according to the invention exhibit an antagonistic action both on the human B1R receptor and on the B1R receptor of the rat.

Particular preference is given to compounds which exhibit at least 15%, 25%, 50%, 70%, 80% or 90% inhibition on the human B1R receptor and/or on the B1R receptor of the rat in the FLIPR assay at a concentration of 10 µM. Very particular preference is given to compounds which exhibit at least 70%, especially 80% and particularly preferably 90% inhibition on the human B1R receptor and on the B1R receptor of the rat.

The agonistic or antagonistic action of substances can be quantified on the bradykinin receptor 1 (B1R) of the species human and rat with ectopically expressing cell lines (CHO K1 cells) and with the aid of a $Ca^{2+}$-sensitive dye (Fluo-4) using a fluorescent imaging plate reader (FLIPR). The indication in % activation is based on the $Ca^{2+}$ signal after addition of Lys-Des-$Arg^9$-bradykinin (0.5 nM) or Des-$Arg^9$-bradykinin (100 nM). Antagonists result in a suppression of the $Ca^{2+}$ influx following administration of the agonist. The % inhibition in comparison with the maximum achievable inhibition is indicated.

The invention also provides a process for the preparation of a substituted sulfonamide derivative according to the invention. The general synthesis scheme is as follows:

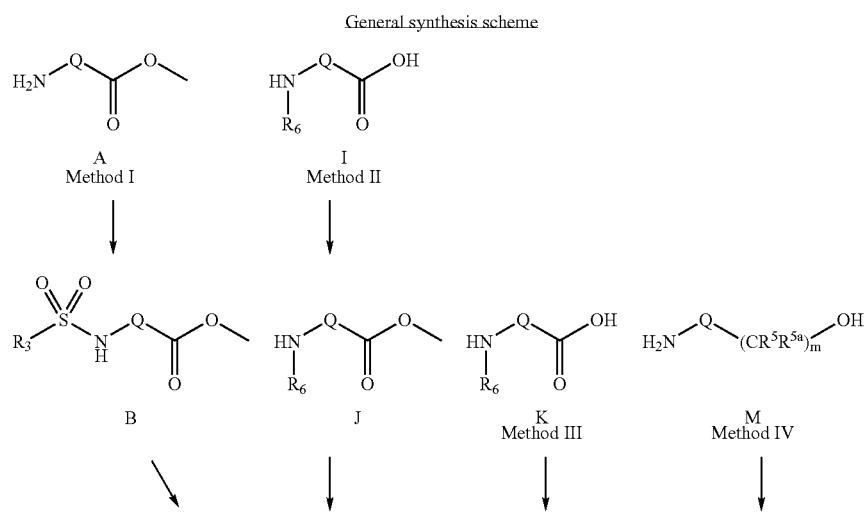

-continued

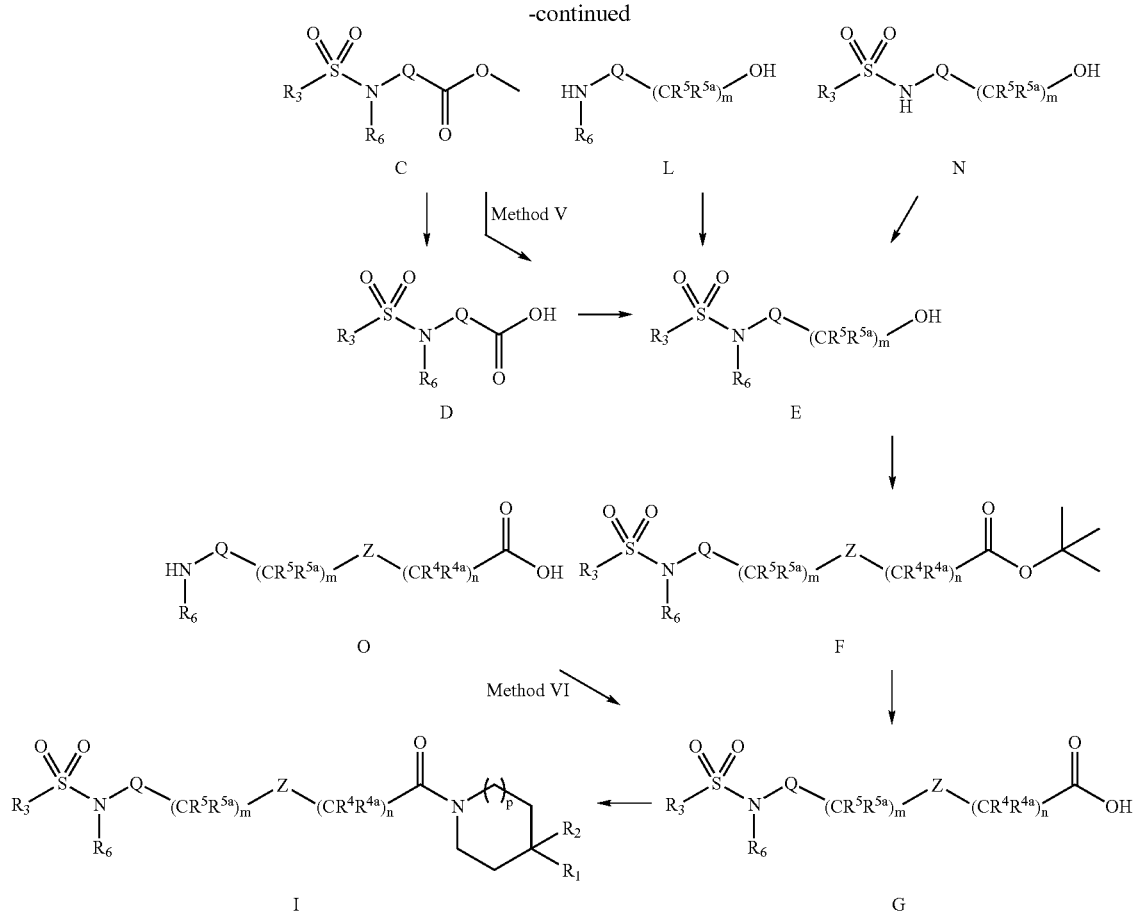

In the scheme shown above, $R^{1-6}$, Z, Q, m, n and p have the same meaning as already described in connection with the general formula I.

General Synthesis Method

Abbreviations

TBTU=O-(benzotriazol-1-yl)-N,N,N',N'-tetramethyluronium tetrafluoroborate
CDI=1,1'-carbonyldiimidazole
DCC=dicyclohexylcarbodiimide
EDCI=1-ethyl-3-(3-dimethylaminopropyl)carbodiimide (HCl salt—see below)
HOAt=1-hydroxy-7-azabenzotriazole
DIPEA=N,N-diisopropylamine
HOBt=1-hydroxybenzotriazole
EDCI=N-(3-dimethylaminopropyl)-N'-ethylcarbodiimide hydrochloride
PyBOP=benzotriazol-1-yl-oxy-tris-pyrrolidino-phosphonium hexafluorophosphate
PFPTFA=pentafluorophenyl trifluoroacetate
PFP=pentafluorophenol
DBU=1,8-diazabicyclo(5.4.0)undec-7-ene In Method I, the amino esters A are converted into the sulfonylated amino esters B in a sulfonylation with sulfonyl chlorides, bromides or pentafluorophenolates $R_3SO_2X$ (X=Cl, Br, OPFP), optionally in the presence of an organic or inorganic base, for example potassium carbonate, sodium bicarbonate, diisopropylethylamine, triethylamine, pyridine, diethylamine or DBU, preferably in an organic solvent, for example acetonitrile, methylene chloride or tetrahydrofuran. The sulfonylated amino esters B are then converted into the sulfonylated amino esters C in an alkylation reaction with alkyl halides (RX, X=I, Br, Cl), mesylates or alternative alkylating reagents, optionally in the presence of an organic or inorganic base, for example sodium hydride, potassium carbonate, caesium carbonate, DBU or DIPEA, preferably in an organic solvent, for example dimethylformamide, acetone, THF, acetonitrile, dioxane or these solvents as mixtures.

In Method II, the racemic (R and S configuration) or enantiomerically pure (R or S configuration) amino acids I are esterified to the amino esters J using dehydrating reagents, for example inorganic acids, such as $H_2SO_4$, or phosphorus oxides, or organic reagents, such as thionyl chloride, in organic solvents, such as THF, diethyl ether, methanol, ethanol or methylene chloride, and then converted into the sulfonylated amino esters C in a sulfonylation with sulfonyl chlorides, bromides or pentafluorophenolates $R_3SO_2X$ (X=Cl, Br, OPFP), optionally in the presence of an organic or inorganic base, for example potassium carbonate, sodium bicarbonate, diisopropylethylamine, triethylamine, pyridine, diethylamine or DBU, preferably in an organic solvent, for example acetonitrile, methylene chloride or tetrahydrofuran.

In Method I and II, the sulfonylated amino esters C will yield the sulfonylated amino acids D in an ester cleavage using organic acids, such as trifluoroacetic acid, or aqueous inorganic acids, such as hydrochloric acid, or using aqueous inorganic bases, such as lithium hydroxide, potassium hydroxide, sodium hydroxide, sodium carbonate, sodium bicarbonate or potassium carbonate, in organic solvents, such as methanol, dioxane, methylene chloride, THF, diethyl ether or in mixtures of these solvents. The amino acids D are converted by a reduction into a sulfonylated amino alcohol E using metal hydrides as reducing agents, such as, for example, $LiAlH_4$, $BH_3$ x DMS or $NaBH_4$, in an organic solvent, such as THF or diethyl ether.

In Method III, the racemic (R and S configuration) or enantiomerically pure (R or S configuration) amino acids K are converted by a reduction into an amino alcohol L (if this is not commercially available) using metal hydrides as reducing agents, such as, for example, $LiAlH_4$, $BH_3$ x DMS or $NaBH_4$, in an organic solvent, such as THF or diethyl ether. The amino alcohols L are converted further into the sulfonylated amino alcohols E in a sulfonylation with sulfonyl chlorides, bromides or pentafluorophenolate $R^3SO_2X$ (X=Cl, Br, OPFP), optionally in the presence of an organic or inorganic base, for example potassium carbonate, sodium bicarbonate, diisopropylethylamine, triethylamine, pyridine, diethylamine or DBU, preferably in an organic solvent, for example acetonitrile, methylene chloride or tetrahydrofuran.

In Method IV, the amino alcohols M are converted into the sulfonylated amino alcohols N in a sulfonylation with sulfonyl chlorides, bromides or pentafluorophenolate $R^3SO_2X$ (X=Cl, Br, OPFP), optionally in the presence of an organic or inorganic base, for example potassium carbonate, sodium bicarbonate, diisopropylethylamine, triethylamine, pyridine, diethylamine or DBU, preferably in an organic solvent, for example acetonitrile, methylene chloride or tetrahydrofuran. The sulfonylated amino alcohols N are then converted into the sulfonylated amino alcohols E in an alkylation reaction with alkyl halides (RX, X=I, Br, Cl), mesylates or alternative alkylating reagents, optionally in the presence of an organic or inorganic base, for example sodium hydride, potassium carbonate, caesium carbonate, DBU or DIPEA, preferably in an organic solvent, for example dimethylformamide, acetone, THF, acetonitrile, dioxane or these solvents as mixtures.

In Methods I to IV, the sulfonylated amino alcohols E are converted into the products of the general structure F in an alkylation reaction with halogenated ester derivatives using tetrabutylammonium chloride or bromide or tetrabutylammonium hydrogen sulfate in a phase transfer reaction using an organic solvent, such as toluene, benzene or xylene, and an inorganic base, such as potassium hydroxide, sodium hydroxide, sodium carbonate, sodium bicarbonate, potassium carbonate, or in the presence of an organic or inorganic base, for example metal alcoholates, such as sodium methanolate, sodium ethanolate, potassium tert-butylate, lithium bases or sodium bases, such as lithium diisopropylamide, butyllithium, tert-butyllithium, sodium methylate, or metal hydrides, such as potassium hydride, lithium hydride, sodium hydride, diisopropylethylamine or triethylamine, in an organic solvent, such as methylene chloride, THF or diethyl ether, and these products give the acid stages of the general formula G in an ester cleavage using organic acids, such as trifluoroacetic acid, or aqueous inorganic acids, such as hydrochloric acid, or using aqueous inorganic bases, such as lithium hydroxide, potassium hydroxide, sodium hydroxide, sodium carbonate, sodium bicarbonate or potassium carbonate, in organic solvents, such as methanol, dioxane, methylene chloride, THF, diethyl ether, or in mixtures of these solvents. The carboxylic acids G are converted into the compounds of the general formula I according to the invention in an amide formation using primary or secondary amines in the presence of dehydrating agents, such as sodium sulfate or magnesium sulfate, phosphorus oxide or reagents such as, for example, CDI, DCC (optionally polymer-bonded), TBTU, EDCI, PyBOP or PFPTFA, also in the presence of HOAt or HOBt and an organic base, for example DIPEA or pyridine, in an organic solvent, such as THF, methylene chloride, diethyl ether, dioxane, DMF or acetonitrile.

In the general Method V, ester derivatives C are converted directly into the sulfonylated amino alcohols E in a reduction reaction using metal hydrides as reducing agent, such as, for example, $LiAlH_4$, $BH_3$ x DMS or $NaBH_4$, in an organic solvent, such as THF or diethyl ether, at a temperature of from −20° C. to reflux temperature.

In the general Method VI, the amino acids O are converted into the sulfonylated amino acids G in a sulfonylation with sulfonyl chlorides, bromides or pentafluorophenolate $R^3SO_2X$ (X=Cl, Br, OPFP), optionally in the presence of an organic or inorganic base, for example potassium hydroxide, sodium hydroxide, potassium carbonate, sodium bicarbonate, diisopropylethylamine, triethylamine, pyridine, diethylamine or DBU, preferably in a solvent, such as, for example, water, tetrahydrofuran, ethanol, acetonitrile or methylene chloride.

The carboxylic acids G are converted into the compounds of the general formula I according to the invention in an amide formation as described under Method I to IV.

The separation of diastereomers and/or enantiomers is carried out by methods known to persons skilled in the art, for example by recrystallization, chromatography or, in particular, HPLC chromatography or crystallization with an optionally chiral acid or base and separation of the salts or chiral HPLC chromatography (Fogassy et al., Optical resolution methods, Org. Biomol. Chem. 2006, 4, 3011-3030). RP-HPLC (mobile phase acetonitrile/water or methanol/water) is particularly suitable for separation of the diastereomers.

The substances according to the invention are suitable as pharmaceutical active compounds in medicaments. The invention therefore also provides pharmaceutical compositions comprising at least one substituted sulfonamide derivative according to the invention and optionally suitable additives and/or auxiliary substances and/or optionally further active compounds.

B1R has been identified, in particular, as being involved in the occurrence of pain. Substituted sulfonamide derivatives according to the invention can accordingly be used for the treatment and/or inhibition of pain, in particular acute, visceral, neuropathic or chronic pain. The invention therefore also provides the use of a substituted sulfonamide derivative according to the invention for the treatment and/or inhibition of pain, in particular acute, visceral, neuropathic or chronic pain.

B1R antagonists are furthermore suitable for treatment of diabetes, diseases of the respiratory tract, inflammatory bowel diseases, neurological diseases, inflammations of the skin, rheumatic diseases, septic shock, reperfusion syndrome, obesity and as an angiogenesis inhibitor. The invention therefore also provides the use of a substituted sulfonamide derivative according to the invention for the treatment and/or alleviation of diabetes, diseases of the respiratory tract, inflammatory bowel diseases, neurological diseases, inflammations of the skin, rheumatic diseases, septic shock, reperfusion syndrome, obesity and as an angiogenesis inhibitor.

In this context, in one of the above uses it may be preferable for a substituted sulfonamide derivative used to be in the form of a pure diastereomer and/or enantiomer, in the form of a racemate or in the form of a non-equimolar or equimolar mixture of the diastereomers and/or enantiomers.

The invention also provides a method for treatment, in particular in one of the above-mentioned indications, of a non-human mammal or human which or who requires treatment of pain, in particular chronic pain, by administration of a therapeutically effective dose of a substituted sulfonamide derivative according to the invention or of a medicament according to the invention.

The pharmaceutical compositions according to the invention optionally comprise, in addition to at least one substituted sulfonamide derivative according to the invention, suitable additives and/or auxiliary substances, that is to say also carrier materials, fillers, solvents, diluents, dyestuffs and/or binders, and can be administered as liquid medicament forms in the form of injection solutions, drops or juices, or as semi-solid medicament forms in the form of granules, tablets, pellets, patches, capsules, plasters or aerosols. The choice of the auxiliary substances etc. and the amounts thereof to be employed depend on whether the pharmaceutical composition is to be administered orally, perorally, parenterally, intravenously, intraperitoneally, intradermally, intramuscularly, intranasally, buccally, rectally or locally, for example to the skin, the mucous membranes or into the eyes. Formulations in the form of tablets, coated tablets, capsules, granules, drops, juices and syrups are suitable for oral administration, and solutions, suspensions, easily reconstitutable dry formulations and sprays are suitable for parenteral, topical and inhalatory administration. Substituted sulfonamide derivatives according to the invention in a depot, in dissolved form or in a plaster, optionally with the addition of agents which promote penetration through the skin, are suitable formulations for percutaneous administration. Formulation forms which can be used orally or percutaneously can release the substituted sulfonamide derivatives according to the invention in a delayed manner. In principle, other further active compounds known to the person skilled in the art can be added to the medicaments according to the invention.

The amount of active compound to be administered to the patient varies according to the weight of the patient, the mode of administration, the indication and the severity of the disease. From 0.005 to 20 mg/kg, preferably from 0.05 to 5 mg/kg of at least one substituted sulfonamide derivative according to the invention are conventionally administered.

The pharmaceutical composition can comprise a substituted sulfonamide compound according to the invention as a pure diastereomer and/or enantiomer, as a racemate or as a non-equimolar or equimolar mixture of the diastereomers and/or enantiomers.

The invention also provides the use of a substituted sulfonamide derivative according to the invention for the preparation of a medicament for treatment of pain, in particular acute, neuropathic or chronic pain.

EXAMPLES

The following examples are intended to illustrate the invention, but do not limit the invention. The yields of the compounds prepared are not optimized. All the temperatures are uncorrected. The term "ether" means diethyl ether, "EA" ethyl acetate, "MC" methylene chloride, "DMF" dimethylformamide, "DME" dimethoxyethane, "DMSO" dimethylsulfoxide and "THF" tetrahydrofuran. The term "equivalents" means equivalent substance amounts, "m.p." melting point or melting range, "decomp." decomposition, "RT" room temperature, "abs." absolute (anhydrous), "rac." racemic, "conc." concentrated, "min" minutes, "h" hours, "d" days, "vol. %" percent by volume, "wt. %" percent by weight and "M" is a concentration stated in moles/liter.

The chemicals and solvents employed were obtained commercially from the conventional suppliers (Acros, Acocado, Aldrich, Bachem, Fluka, Lancaster, Maybridge, Merck, Sigma, TCi, Fulcrum Scientific, Array Biopharma, Asinex, ChemDiv etc.). Silica gel 60 (0.040-0.063 mm) from E. Merck, Darmstadt was employed as the stationary phase for the column chromatography. The thin-layer chromatography investigations were carried out using HPTLC precoated plates, silica gel 60 F 254 from E. Merck, Darmstadt. The mixture ratios of mobile phases for chromatography investigations are always stated in volume/volume. The analysis was carried out via HPLC-MS, and precursors were confirmed via NMR.

Preparation of the Acid Units
Examples of the acid units, table

| Example | Synthesis method | Ester cleavage variant | Structure | Name |
|---|---|---|---|---|
| S1 | 1 | A | 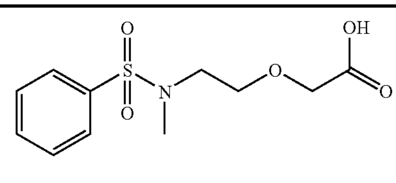 | [2-(Phenylsulfonyl-methyl-amino)-ethoxy]-acetic acid |
| S2 | 1 | A | 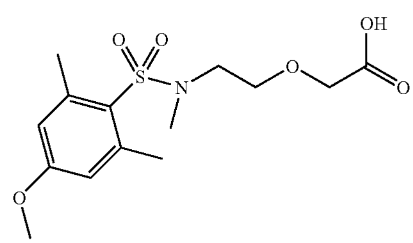 [SMILES: COc1cc(C)c(S(=O)(=O)N(C)CCOCC(=O)O)c(C)c1] | {2-[(4-Methoxy-2,6-dimethyl-phenylsulfonyl)-methyl-amino]-ethoxy}-acetic acid |
| S3 | 1 | A | 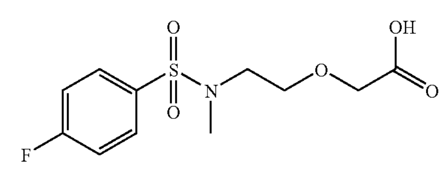 [SMILES: CN(CCOCC(=O)O)S(=O)(=O)c1ccc(F)cc1] | {2-[(4-Fluoro-phenyl-sulfonyl)-methyl-amino]-ethoxy}-acetic acid |

-continued

| Example | Synthesis method | Ester cleavage variant | Structure | Name |
|---|---|---|---|---|
| S4 | 1 | A | 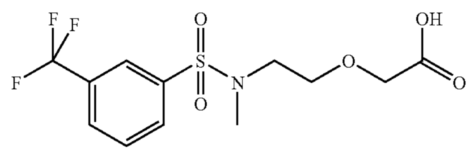 [SMILES: CN(CCOCC(=O)O)S(=O)(=O)c1cccc(C(F)(F)F)c1] | {2-[Methyl-(3-trifluoro-methyl-phenylsulfonyl)-amino]-ethoxy}-acetic acid |
| S5 | 1 | A | 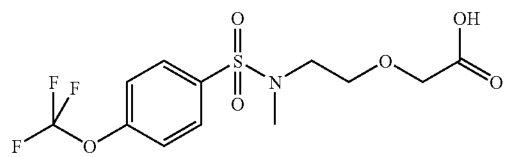 [SMILES: CN(CCOCC(=O)O)S(=O)(=O)c1ccc(OC(F)(F)F)cc1] | {2-[Methyl-(4-trifluoro-methoxy-phenylsulfonyl)-amino]-ethoxy}-acetic acid |
| S6 | 1 | C | 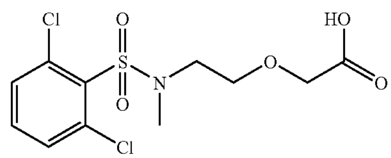 [SMILES: CN(CCOCC(=O)O)S(=O)(=O)c1c(Cl)cccc1Cl] | {2-[(2,6-Dichloro-phenyl-sulfonyl)-methyl-amino]-ethoxy}-acetic acid |
| S7 | 1 | A | 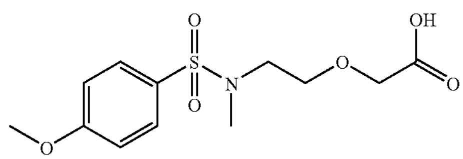 [SMILES: COc1ccc(S(=O)(=O)N(C)CCOCC(=O)O)cc1] | {2-[(4-Methoxy-phenylsulfonyl)-methyl-amino]-ethoxy}-acetic acid |
| S8 | 1 | A | 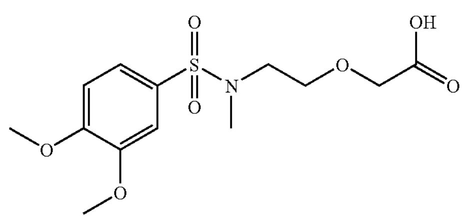 [SMILES: COc1ccc(S(=O)(=O)N(C)CCOCC(=O)O)cc1OC] | {2-[(3,4-Dimethoxy-phenylsulfonyl)-methyl-amino]-ethoxy}-acetic acid |
| S9 | 1 | C | 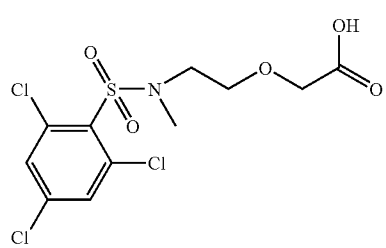 [SMILES: CN(CCOCC(=O)O)S(=O)(=O)c1c(Cl)cc(Cl)cc1Cl] | {2-[Methyl-(2,4,6-trichloro-phenylsulfonyl)-amino]-ethoxy}-acetic acid |
| S10 | 1 | A | 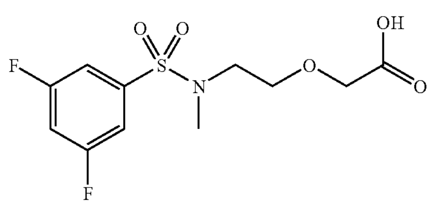 [SMILES: CN(CCOCC(=O)O)S(=O)(=O)c1cc(F)cc(F)c1] | {2-[(3,5-Difluoro-phenylsulfonyl)-methyl-amino]-ethoxy}-acetic acid |
| S11 | 1 | A | 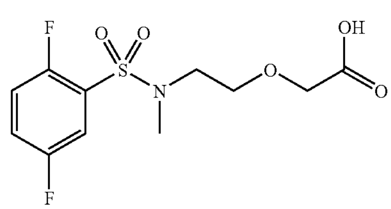 [SMILES: CN(CCOCC(=O)O)S(=O)(=O)c1cc(F)ccc1F] | {2-[(2,5-Difluoro-phenylsulfonyl)-methyl-amino]-ethoxy}-acetic acid |

-continued

| Example | Synthesis method | Ester cleavage variant | Structure | Name |
|---|---|---|---|---|
| S12 | 1 | A | 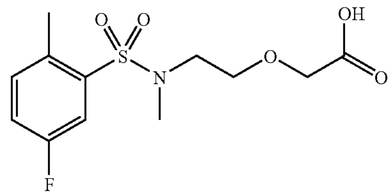 | {2-[(5-Fluoro-2-methyl-phenylsulfonyl)-methyl-amino]-ethoxy}-acetic acid |
| S13 | 1 | A | 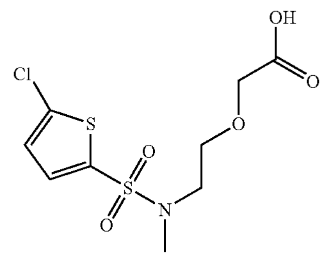 [SMILES: CN(CCOCC(=O)O)S(=O)(=O)c1ccc(Cl)s1] | {2-[(5-Chloro-thiophene-2-sulfonyl)-methyl-amino]-ethoxy}-acetic acid |
| S14 | 1 | C | 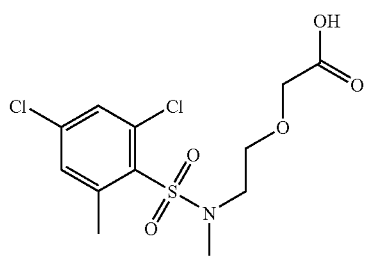 [SMILES: Cc1cc(Cl)cc(Cl)c1S(=O)(=O)N(C)CCOCC(=O)O] | {2-[(2,4-Dichloro-6-methyl-phenylsulfonyl)-methyl-amino]-ethoxy}-acetic acid |
| S15 | 3 | C | 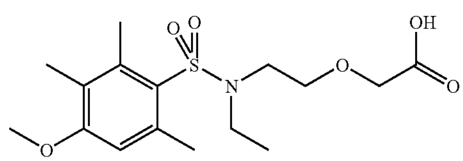 [SMILES: CCN(CCOCC(=O)O)S(=O)(=O)c1c(C)cc(OC)c(C)c1C] | {2-[Ethyl-(4-methoxy-2,3,6-trimethyl-phenylsulfonyl)-amino]-ethoxy}-acetic acid |
| S16 | 1 | B | 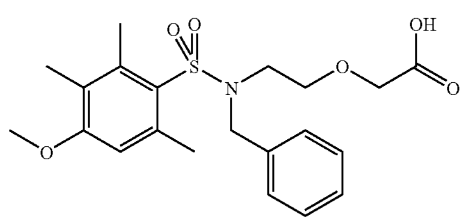 [SMILES: COc1cc(C)c(S(=O)(=O)N(CCOCC(=O)O)Cc2ccccc2)c(C)c1C] | {2-[Benzyl-(4-methoxy-2,3,6-trimethyl-phenyl-sulfonyl)-amino]-ethoxy}-acetic acid |
| S17 | 2 | B | 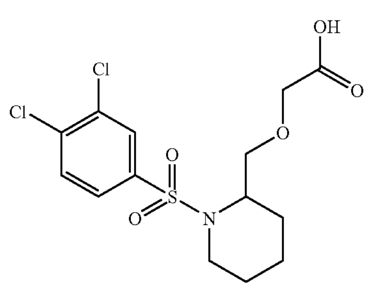 [SMILES: O=C(O)COCC1CCCCN1S(=O)(=O)c1ccc(Cl)c(Cl)c1] | [1-(3,4-Dichloro-phenylsulfonyl)-piperidin-2-ylmethoxy]-acetic acid |

-continued

| Example | Synthesis method | Ester cleavage variant | Structure | Name |
|---|---|---|---|---|
| S18 | 2 | B | 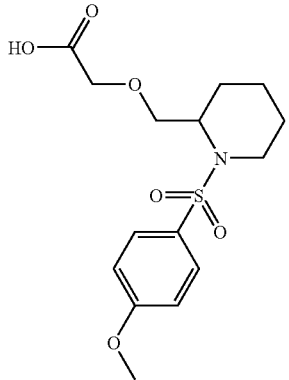 [SMILES: COc1ccc(S(=O)(=O)N2CCCCC2COCC(=O)O)cc1] | [1-(4-Methoxy-phenyl-sulfonyl)-piperidin-2-ylmethoxy]-acetic acid |
| S19 | 2 | B | 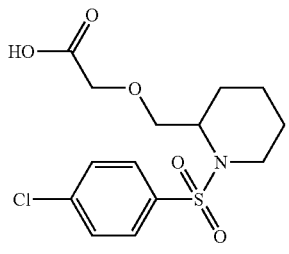 [SMILES: O=C(O)COCC1CCCCN1S(=O)(=O)c1ccc(Cl)cc1] | [1-(4-Chloro-phenyl-sulfonyl)-piperidin-2-ylmethoxy]-acetic acid |
| S20 | 2 | B | 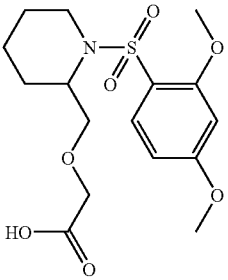 [SMILES: COc1ccc(S(=O)(=O)N2CCCCC2COCC(=O)O)c(OC)c1] | [1-(2,4-Dimethoxy-phenylsulfonyl)-piperidin-2-ylmethoxy]-acetic acid |
| S21 | 2 | B | 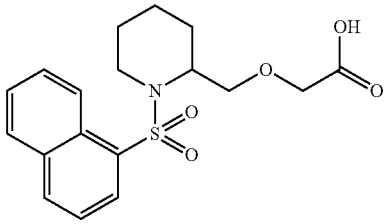 [SMILES: O=C(O)COCC1CCCCN1S(=O)(=O)c1cccc2ccccc12] | [1-(Naphthalene-1-sulfonyl)-piperidin-2-ylmethoxy]-acetic acid |
| S22 | 2 | B | 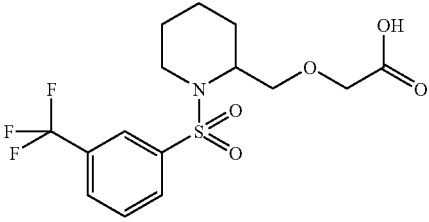 [SMILES: O=C(O)COCC1CCCCN1S(=O)(=O)c1cccc(C(F)(F)F)c1] | [1-(3-Trifluoromethyl-phenylsulfonyl)-piperidin-2-ylmethoxy]-acetic acid |

-continued

| Example | Synthesis method | Ester cleavage variant | Structure | Name |
|---|---|---|---|---|
| S23 | 2 | B | 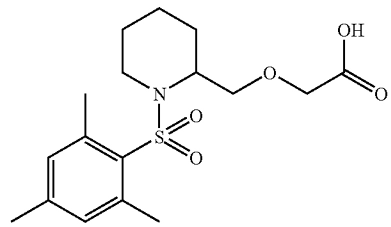 [SMILES: Cc1cc(C)c(S(=O)(=O)N2CCCCC2COCC(=O)O)c(C)c1] | [1-(2,4,6-Trimethyl-phenylsulfonyl)-piperidin-2-ylmethoxy]-acetic acid |
| S24 | 2 | B | 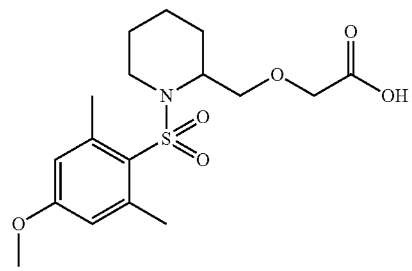 [SMILES: COc1cc(C)c(S(=O)(=O)N2CCCCC2COCC(=O)O)c(C)c1] | [1-(4-Methoxy-2,6-dimethyl-phenylsulfonyl)-piperidin-2-ylmethoxy]-acetic acid |
| S25 | 2 | B | 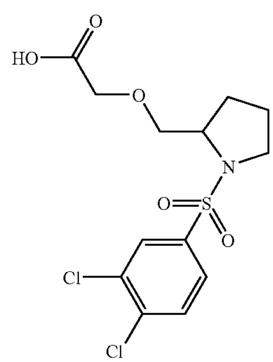 [SMILES: O=C(O)COCC1CCCN1S(=O)(=O)c1ccc(Cl)c(Cl)c1] | [1-(3,4-Dichloro-phenyl-sulfonyl)-pyrrolidin-2-ylmethoxy]-acetic acid |
| S26 | 2 | B | 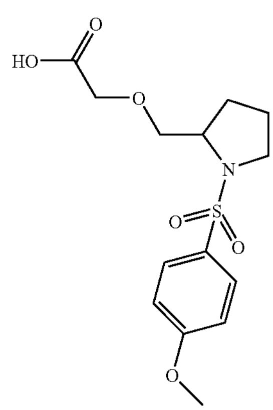 [SMILES: COc1ccc(S(=O)(=O)N2CCCC2COCC(=O)O)cc1] | [1-(4-Methoxy-phenylsulfonyl)-pyrrolidin-2-ylmethoxy]-acetic acid |
| S27 | 2 | B | 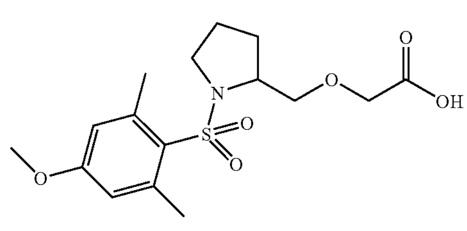 [SMILES: COc1cc(C)c(S(=O)(=O)N2CCCC2COCC(=O)O)c(C)c1] | [1-(4-Methoxy-2,6-dimethyl-phenylsulfonyl)-pyrrolidin-2-ylmethoxy]-acetic acid |

-continued

| Example | Synthesis method | Ester cleavage variant | Structure | Name |
|---------|------------------|------------------------|-----------|------|
| S28 | 1 | B | 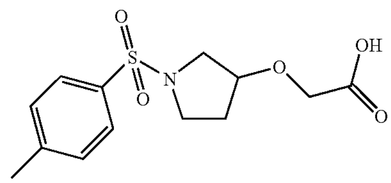 [SMILES: Cc1ccc(S(=O)(=O)N2CCC(OCC(=O)O)C2)cc1] | [1-(Toluene-4-sulfonyl)-pyrrolidin-3-yloxy]-acetic acid |
| S29 | 1 | B | 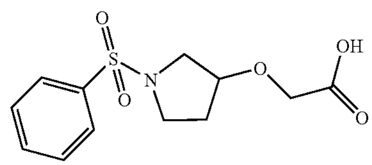 [SMILES: O=C(O)COC1CCN(S(=O)(=O)c2ccccc2)C1] | (1-Phenylsulfonyl-pyrrolidin-3-yloxy)-acetic acid |
| S30 | 1 | B | 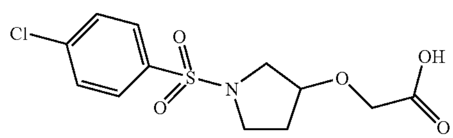 [SMILES: O=C(O)COC1CCN(S(=O)(=O)c2ccc(Cl)cc2)C1] | [1-(4-Chloro-phenyl-sulfonyl)-pyrrolidin-3-yloxy]-acetic acid |
| S31 | 1 | C | 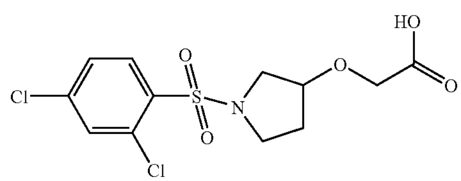 [SMILES: O=C(O)COC1CCN(S(=O)(=O)c2ccc(Cl)cc2Cl)C1] | [1-(2,4-Dichloro-phenyl-sulfonyl)-pyrrolidin-3-yloxy]-acetic acid |
| S32 | 1 | B | 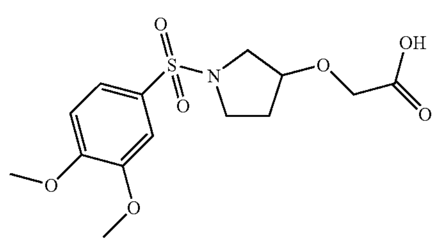 [SMILES: COc1ccc(S(=O)(=O)N2CCC(OCC(=O)O)C2)cc1OC] | [1-(3,4-Dimethoxy-phenylsulfonyl)-pyrrolidin-3-yloxy]-acetic acid |
| S33 | 1 | B | 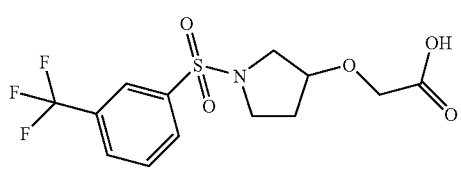 [SMILES: O=C(O)COC1CCN(S(=O)(=O)c2cccc(C(F)(F)F)c2)C1] | [1-(3-Trifluoromethyl-phenylsulfonyl)-pyrrolidin-3-yloxy]-acetic acid |
| S34 | 1 | B | 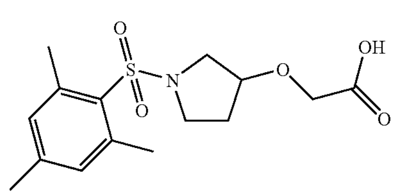 [SMILES: Cc1cc(C)c(S(=O)(=O)N2CCC(OCC(=O)O)C2)c(C)c1] | [1-(2,4,6-Trimethyl-phenylsulfonyl)-pyrrolidin-3-yloxy]-acetic acid |
| S35 | 1 | B | 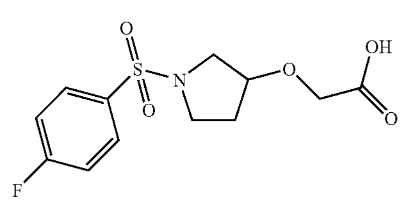 [SMILES: O=C(O)COC1CCN(S(=O)(=O)c2ccc(F)cc2)C1] | [1-(4-Fluoro-phenyl-sulfonyl)-pyrrolidin-3-yloxy]-acetic acid |

| Example | Synthesis method | Ester cleavage variant | Structure | Name |
|---------|------------------|------------------------|-----------|------|
| S36 | 1 | B | 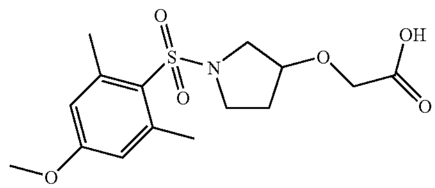 [SMILES: COc1cc(C)c(S(=O)(=O)N2CCC(OCC(=O)O)C2)c(C)c1] | [1-(4-Methoxy-2,6-dimethyl-phenylsulfonyl)-pyrrolidin-3-yloxy]-acetic acid |
| S37 | 1 | B | 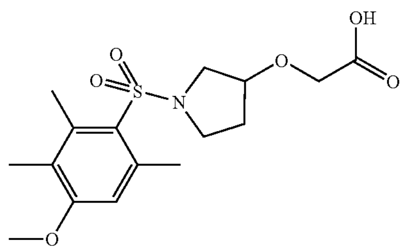 [SMILES: COc1cc(C)c(S(=O)(=O)N2CCC(OCC(=O)O)C2)c(C)c1C] | [1-(4-Methoxy-2,3,6-trimethyl-phenylsulfonyl)-pyrrolidin-3-yloxy]-acetic acid |
| S38 | 1 | C | 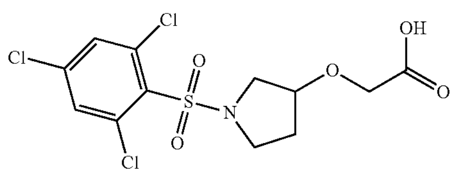 [SMILES: O=C(O)COC1CCN(S(=O)(=O)c2c(Cl)cc(Cl)cc2Cl)C1] | [1-(2,4,6-Trichloro-phenyl-sulfonyl)-pyrrolidin-3-loxy]-acetic acid |
| S39 | 2 | B | 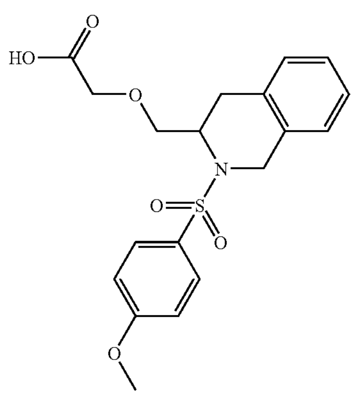 [SMILES: COc1ccc(S(=O)(=O)N2Cc3ccccc3CC2COCC(=O)O)cc1] | [2-(4-Methoxy-phenylsulfonyl)-1,2,3,4-tetrahydro-isoquinolin-3-ylmethoxy]-acetic acid |
| S40 | 2 | B | 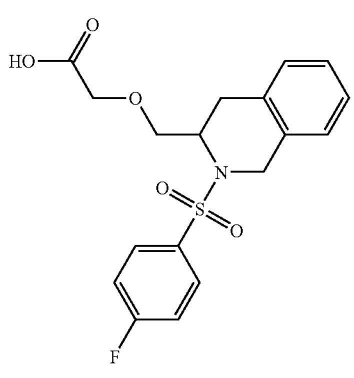 [SMILES: O=C(O)COCC1Cc2ccccc2CN1S(=O)(=O)c1ccc(F)cc1] | [2-(4-Fluoro-phenyl-sulfonyl)-1,2,3,4-tetrahydro-isoquinolin-3-ylmethoxy]-acetic acid |

-continued

| Example | Synthesis method | Ester cleavage variant | Structure | Name |
|---|---|---|---|---|
| S41 | 2 | B | 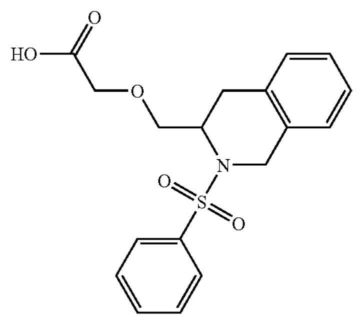 [SMILES: O=C(O)COCC1Cc2ccccc2CN1S(=O)(=O)c1ccccc1] | (2-Phenylsulfonyl-1,2,3,4-tetrahydro-isoquinolin-3-ylmethoxy)-acetic acid |
| S42 | 2 | B | 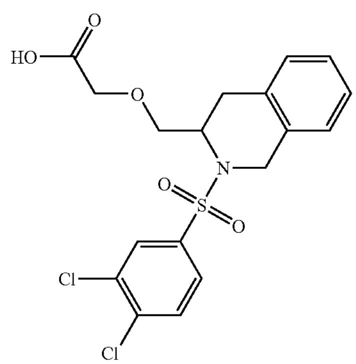 [SMILES: O=C(O)COCC1Cc2ccccc2CN1S(=O)(=O)c1ccc(Cl)c(Cl)c1] | [2-(3,4-Dichloro-phenyl-sulfonyl)-1,2,3,4-tetrahydro-isoquinolin-3-ylmethoxy]-acetic acid |
| S43 | 2 | B | 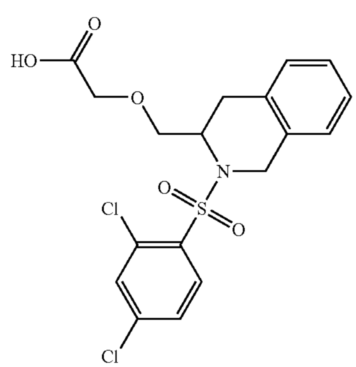 [SMILES: O=C(O)COCC1Cc2ccccc2CN1S(=O)(=O)c1ccc(Cl)cc1Cl] | [2-(2,4-Dichloro-phenyl-sulfonyl)-1,2,3,4-tetrahydro-isoquinolin-3-ylmethoxy]-acetic acid |
| S44 | 2 | B | 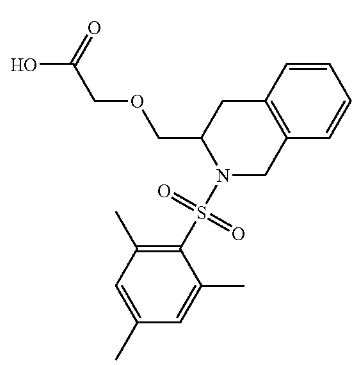 [SMILES: Cc1cc(C)c(S(=O)(=O)N2Cc3ccccc3CC2COCC(=O)O)c(C)c1] | [2-(2,4,6-Trimethyl-phenylsulfonyl)-1,2,3,4-tetrahydro-isoquinolin-3-ylmethoxy]-acetic acid |

-continued

| Example | Synthesis method | Ester cleavage variant | Structure | Name |
|---|---|---|---|---|
| S45 | 1 | C | 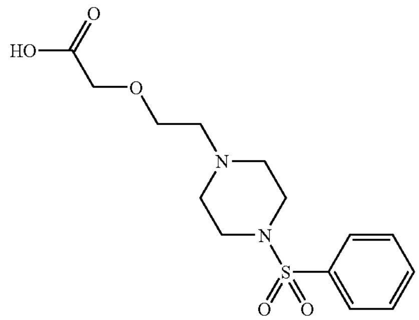 [SMILES: O=C(O)COCCN1CCN(S(=O)(=O)c2ccccc2)CC1] | [2-(4-Phenylsulfonyl-piperazin-1-yl)-ethoxy]-acetic acid |
| S46 | 1 | C | 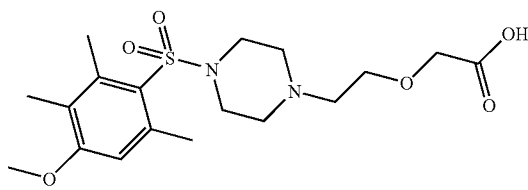 [SMILES: COc1cc(C)c(S(=O)(=O)N2CCN(CCOCC(=O)O)CC2)c(C)c1C] | {2-[4-(4-Methoxy-2,3,6-trimethyl-phenylsulfonyl)-piperazin-1-yl]-ethoxy}-acetic acid |
| S47 | 1 | C | 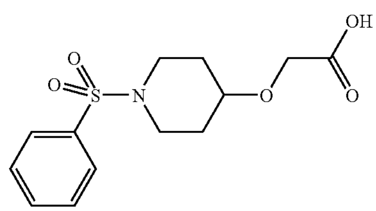 [SMILES: O=C(O)COC1CCN(S(=O)(=O)c2ccccc2)CC1] | (1-Phenylsulfonyl-piperidin-4-yloxy)-acetic acid |
| S48 | 1 | C | 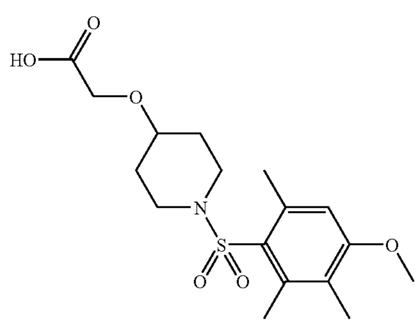 [SMILES: COc1cc(C)c(S(=O)(=O)N2CCC(OCC(=O)O)CC2)c(C)c1C] | [1-(4-Methoxy-2,3,6-trimethyl-phenylsulfonyl)-piperidin-4-yloxy]-acetic acid |
| S49 | 1 | C | 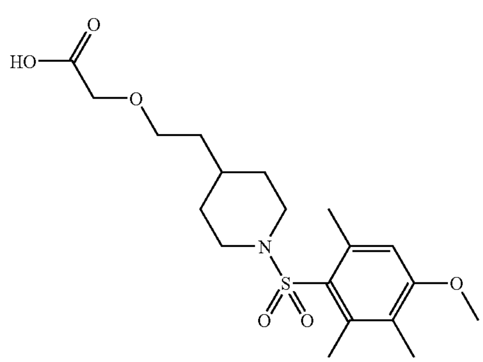 [SMILES: COc1cc(C)c(S(=O)(=O)N2CCC(CCOCC(=O)O)CC2)c(C)c1C] | {2-[1-(4-Methoxy-2,3,6-trimethyl-phenylsulfonyl)-piperidin-4-yl]-ethoxy}-acetic acid |
| S50 | 1 | C | 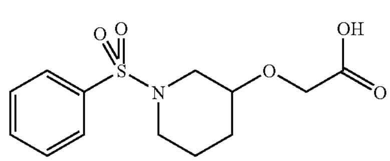 [SMILES: O=C(O)COC1CCCN(S(=O)(=O)c2ccccc2)C1] | (1-Phenylsulfonyl-piperidin-3-yloxy)-acetic acid |

-continued

| Example | Synthesis method | Ester cleavage variant | Structure | Name |
|---|---|---|---|---|
| S51 | 1 | C | 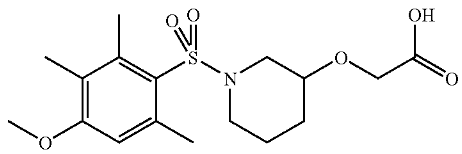 [SMILES: COc1cc(C)c(S(=O)(=O)N2CCCC(OCC(=O)O)C2)c(C)c1C] | [1-(4-Methoxy-2,3,6-trimethyl-phenylsulfonyl)-piperidin-3-yloxy]-acetic acid |
| S52 | 1 | C | 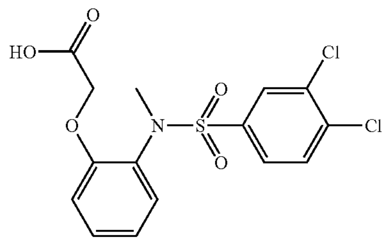 [SMILES: CN(c1ccccc1OCC(=O)O)S(=O)(=O)c1ccc(Cl)c(Cl)c1] | {2-[(3,4-Dichloro-phenyl-sulfonyl)-methyl-amino]-phenoxy}-acetic acid |
| S53 | 1 | C | 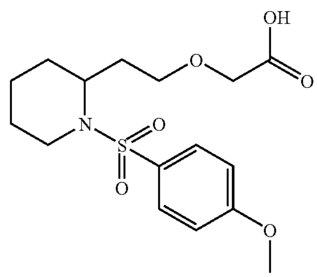 [SMILES: COc1ccc(S(=O)(=O)N2CCCCC2CCOCC(=O)O)cc1] | {2-[1-(4-Methoxy-phenyl-sulfonyl)-piperidin-2-yl]-ethoxy}-acetic acid |
| S54 | 3 | B | 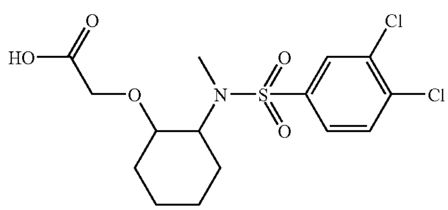 [SMILES: CN(C1CCCCC1OCC(=O)O)S(=O)(=O)c1ccc(Cl)c(Cl)c1] | {2-[(3,4-Dichloro-phenyl-sulfonyl)-methyl-amino]-cyclohexyloxy}-acetic acid |
| S55 | 3 | B | 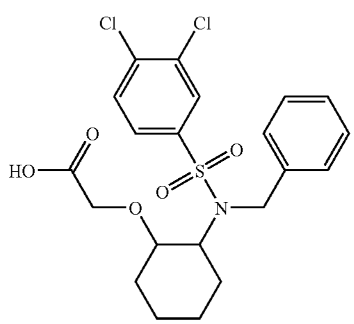 [SMILES: O=C(O)COC1CCCCC1N(Cc1ccccc1)S(=O)(=O)c1ccc(Cl)c(Cl)c1] | {2-[Benzyl-(3,4-dichloro-phenylsulfonyl)-amino]-cyclohexyloxy}-acetic acid |
| S56 | 5 | — | 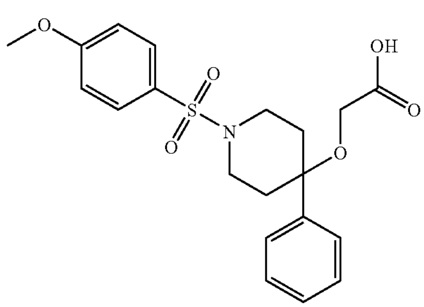 [SMILES: COc1ccc(S(=O)(=O)N2CCC(OCC(=O)O)(c3ccccc3)CC2)cc1] | [1-(4-Methoxy-phenyl-sulfonyl)-4-phenyl-piperidin-4-yloxy]-acetic acid |

-continued

| Example | Synthesis method | Ester cleavage variant | Structure | Name |
|---|---|---|---|---|
| S57 | 6 | — | 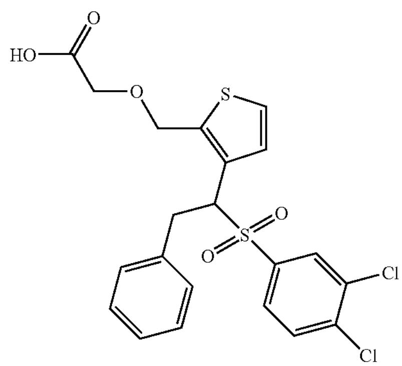 [SMILES: O=C(O)COCc1sccc1C(Cc1ccccc1)S(=O)(=O)c1ccc(Cl)c(Cl)c1] | {3-[Benzyl-(3,4-dichloro-phenylsulfonyl)-amino]-thiophen-2-ylmethoxy}-acetic acid |
| S58 | 4 | — | 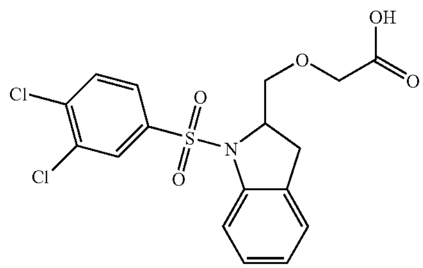 [SMILES: O=C(O)COCC1Cc2ccccc2N1S(=O)(=O)c1ccc(Cl)c(Cl)c1] | [1-(3,4-Dichloro-phenyl-sulfonyl)-2,3-dihydro-1H-indol-2-ylmethoxy]-acetic acid |
| S59 | 1 | D | 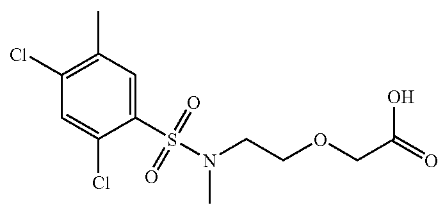 | 2-(2-(2,4-Dichloro-N,5-dimethylphenylsulfon-amide)ethoxy)-acetic acid |
| S60 | 1 | E | 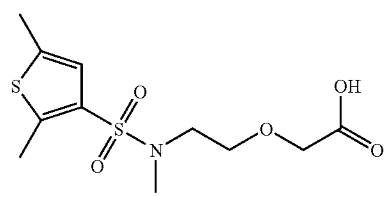 [SMILES: Cc1cc(S(=O)(=O)N(C)CCOCC(=O)O)c(C)s1] | 2-(2-(N,2,5-Trimethyl-thiophene-3-sulfonamide)-ethoxy)-acetic acid |
| S61 | 1 | A | 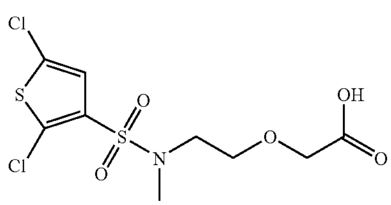 [SMILES: CN(CCOCC(=O)O)S(=O)(=O)c1cc(Cl)sc1Cl] | 2-(2-(2,5-Dichloro-N-methylthiophene-3-sulfonamide)ethoxy)-acetic acid |
| S62 | 1 | F | 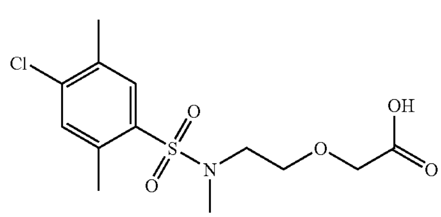 [SMILES: Cc1cc(S(=O)(=O)N(C)CCOCC(=O)O)c(C)cc1Cl] | 2-(2-(4-Chloro-N,2,5-trimethylphenylsulfon-amide)ethoxy)-acetic acid |

-continued

| Example | Synthesis method | Ester cleavage variant | Structure | Name |
|---------|------------------|------------------------|-----------|------|
| S63 | 7 | E | 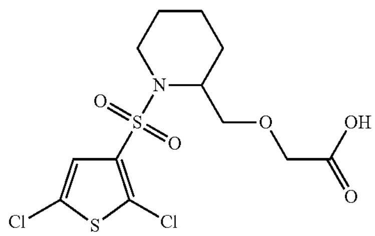 [SMILES: O=C(O)COCC1CCCCN1S(=O)(=O)c1cc(Cl)sc1Cl] | 2-((1-(2,5-Dichlorothiophen-3-ylsulfonyl)piperidin-2-yl)methoxy)-acetic acid |
| S64 | 7 | G | 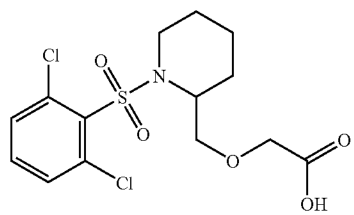 [SMILES: O=C(O)COCC1CCCCN1S(=O)(=O)c1c(Cl)cccc1Cl] | 2-((1-(2,6-Dichlorophenyl-sulfonyl)piperidin-2-yl)-methoxy)-acetic acid |
| S65 | 7 | F | 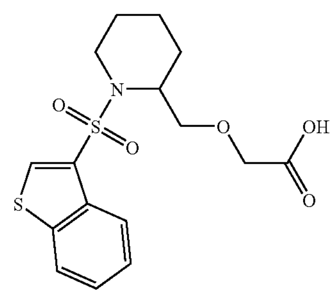 [SMILES: O=C(O)COCC1CCCCN1S(=O)(=O)c1csc2ccccc12] | 2-((1-(Benzo[b]thiophen-3-ylsulfonyl)piperidin-2-yl)-methoxy)-acetic acid |
| S66 | 7 | E | 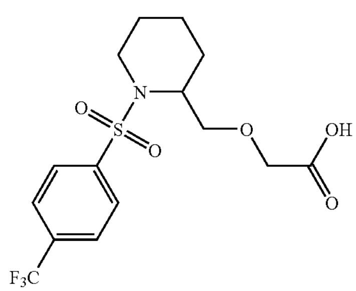 [SMILES: O=C(O)COCC1CCCCN1S(=O)(=O)c1ccc(C(F)(F)F)cc1] | 2-((1-(4-(Trifluoromethyl)-phenylsulfonyl)piperidin-2-yl)methoxy)-acetic acid |
| S67 | 7 | E | 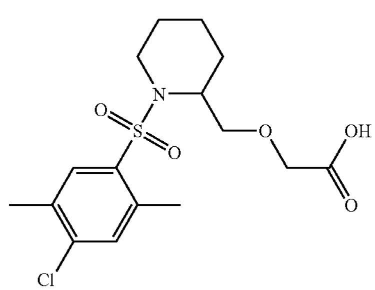 [SMILES: Cc1cc(S(=O)(=O)N2CCCCC2COCC(=O)O)c(C)cc1Cl] | 2-((1-(4-Chloro-2,5-dimethylphenylsulfonyl)-piperidin-2-yl)methoxy)-acetic acid |

-continued

| Example | Synthesis method | Ester cleavage variant | Structure | Name |
|---|---|---|---|---|
| S68 | 7 | F | 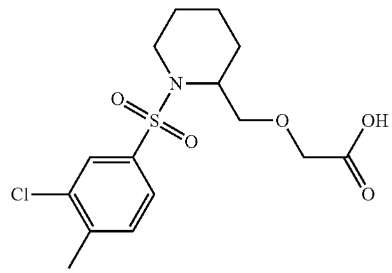 [SMILES: Cc1ccc(S(=O)(=O)N2CCCCC2COCC(=O)O)cc1Cl] | 2-((1-(3-Chloro-4-methyl-phenylsulfonyl)piperidin-2-yl)methoxy)-acetic acid |
| S69 | — | — | 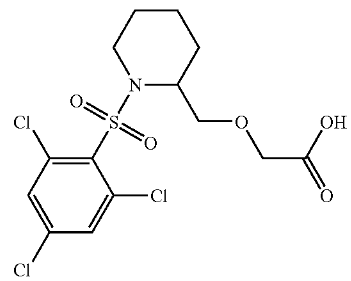 [SMILES: O=C(O)COCC1CCCCN1S(=O)(=O)c1c(Cl)cc(Cl)cc1Cl] | 2-((1-(2,6-Dichloro-4-(trifluoromethyl)phenyl-sulfonyl)piperidin-2-yl)-methoxy)-acetic acid |
| S70 | 7 | E | 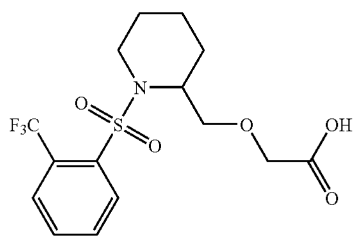 [SMILES: O=C(O)COCC1CCCCN1S(=O)(=O)c1ccccc1C(F)(F)F] | 2-((1-(2-(Trifluoromethyl)-phenylsulfonyl)piperidin-2-yl)methoxy)-acetic acid |
| S71 | 7 | B | 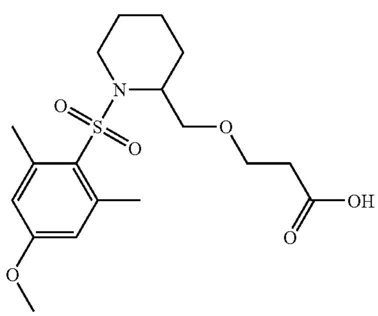 [SMILES: COc1cc(C)c(S(=O)(=O)N2CCCCC2COCCC(=O)O)c(C)c1] | 3-((1-(4-Methoxy-2,6-dimethylphenylsulfonyl)-piperidin-2-yl)methoxy)-propionic acid |
| S72 | 1 | C | 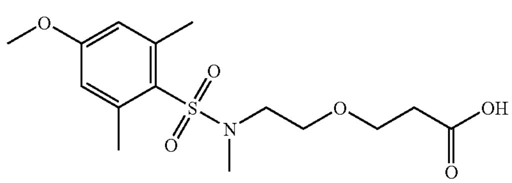 [SMILES: COc1cc(C)c(S(=O)(=O)N(C)CCOCCC(=O)O)c(C)c1] | 3-(2-(4-Methoxy-N,2,6-trimethylphenylsulfon-amide)ethoxy)-propionic acid |
| S73 | 1 | G | 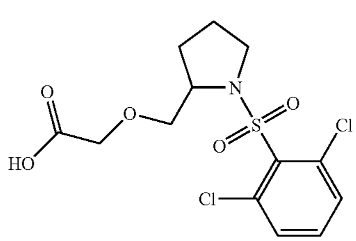 [SMILES: O=C(O)COCC1CCCN1S(=O)(=O)c1c(Cl)cccc1Cl] | 2-((1-(2,6-Dichlorophenyl-sulfonyl)pyrrolidin-2-yl)-methoxy)-acetic acid |

-continued

| Example | Synthesis method | Ester cleavage variant | Structure | Name |
|---------|------------------|------------------------|-----------|------|
| S74 | 1 | A | 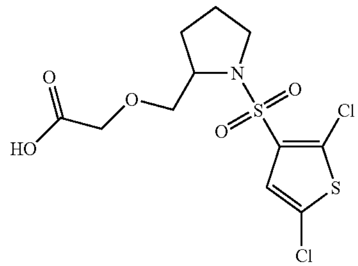 [SMILES: O=C(O)COCC1CCCN1S(=O)(=O)c1cc(Cl)sc1Cl] | 2-((1-(2,5-Dichlorothiophen-3-ylsulfonyl)pyrrolidin-2-yl)-methoxy)-acetic acid |
| S75 | 1 | A | 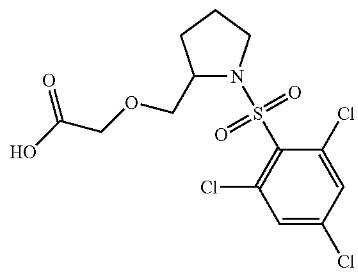 [SMILES: O=C(O)COCC1CCCN1S(=O)(=O)c1c(Cl)cc(Cl)cc1Cl] | 2-((1-(2,4,6-Trichloro-phenylsulfonyl)pyrrolidin-2-yl)methoxy)-acetic acid |
| S76 | — | — | 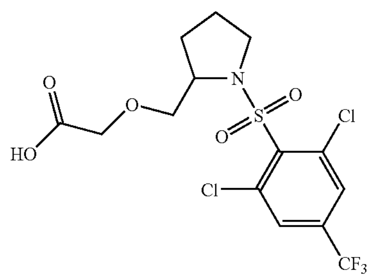 [SMILES: O=C(O)COCC1CCCN1S(=O)(=O)c1c(Cl)cc(C(F)(F)F)cc1Cl] | 2-((1-(2,6-Dichloro-4-(trifluoromethyl)phenyl-sulfonyl)pyrrolidin-2-yl)-methoxy)-acetic acid |
| S77 | 1 | G | 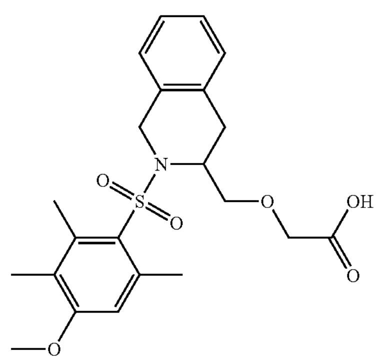 [SMILES: COc1cc(C)c(S(=O)(=O)N2Cc3ccccc3CC2COCC(=O)O)c(C)c1C] | 2-((2-(4-Methoxy-2,3,6-trimethylphenylsulfonyl)-1,2,3,4-tetrahydroiso-quinolin-3-yl)methoxy)-acetic acid |
| S78 | — | — | 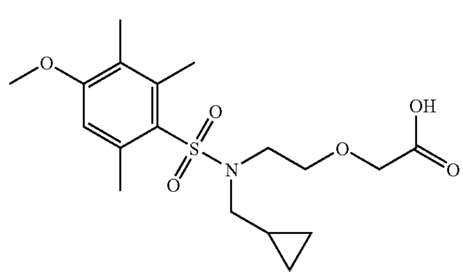 [SMILES: COc1cc(C)c(S(=O)(=O)N(CCOCC(=O)O)CC2CC2)c(C)c1C] | 2-(2-(N-(Cyclopropyl-methyl)-4-methoxy-2,3,6-trimethylphenylsulfon-amide)ethoxy)-acetic acid |

-continued

| Example | Synthesis method | Ester cleavage variant | Structure | Name |
|---|---|---|---|---|
| S79 | — | — | 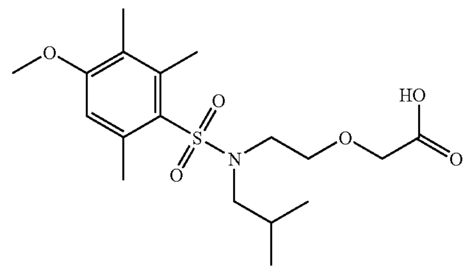 [SMILES: COc1cc(C)c(S(=O)(=O)N(CCOCC(=O)O)CC(C)C)c(C)c1C] | 2-(2-(N-Isobutyl-4-methoxy-2,3,6-trimethylphenylsulfonamide)ethoxy)-acetic acid |
| S80 | — | — | 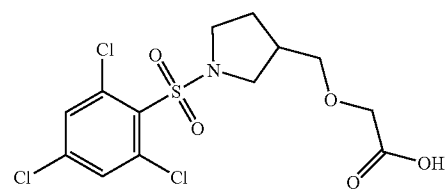 [SMILES: O=C(O)COCC1CCN(S(=O)(=O)c2c(Cl)cc(Cl)cc2Cl)C1] | 2-((1-(2,4,6-Trichlorophenylsulfonyl)pyrrolidin-3-yl)methoxy)-acetic acid |
| S81 | 1 | F | 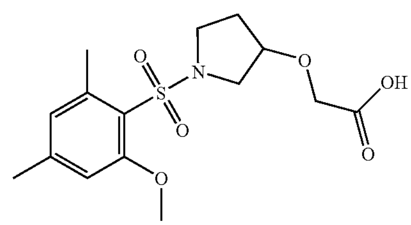 [SMILES: COc1cc(C)cc(C)c1S(=O)(=O)N1CCC(OCC(=O)O)C1] | 2-(1-(2-Methoxy-4,6-dimethylphenylsulfonyl)-pyrrolidin-3-yloxy)-acetic acid |
| S82 | 1 | F | 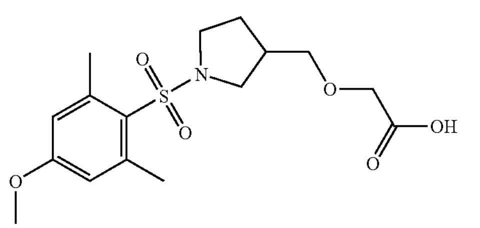 [SMILES: COc1cc(C)c(S(=O)(=O)N2CCC(COCC(=O)O)C2)c(C)c1] | 2-((1-(4-Methoxy-2,6-dimethylphenylsulfonyl)-pyrrolidin-3-yl)methoxy)-acetic acid |
| S83 | 1 | C | 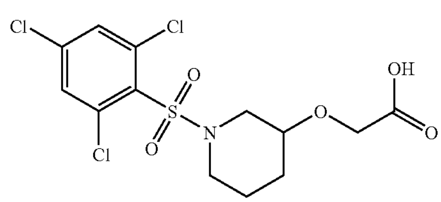 [SMILES: O=C(O)COC1CCCN(S(=O)(=O)c2c(Cl)cc(Cl)cc2Cl)C1] | 2-(1-(2,4,6-Trichlorophenylsulfonyl)piperidin-3-yloxy)-acetic acid |
| S84 | 1 | B | 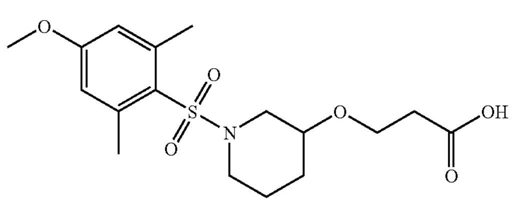 [SMILES: COc1cc(C)c(S(=O)(=O)N2CCCC(OCCC(=O)O)C2)c(C)c1] | 3-(1-(4-Methoxy-2,6-dimethylphenylsulfonyl)-piperidin-3-yloxy)-propionic acid |
| S85 | 1 | F | 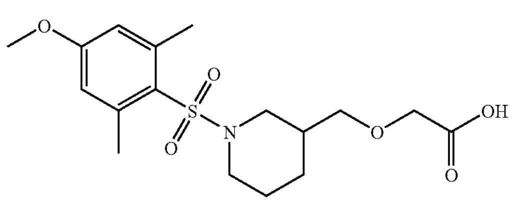 [SMILES: COc1cc(C)c(S(=O)(=O)N2CCCC(COCC(=O)O)C2)c(C)c1] | 2-((1-(4-Methoxy-2,6-dimethylphenylsulfonyl)-piperidin-3-yl)methoxy)-acetic acid |

-continued

| Example | Synthesis method | Ester cleavage variant | Structure | Name |
|---|---|---|---|---|
| S86 | 1 | A | 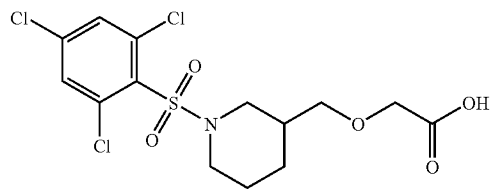 [SMILES: O=C(O)COCC1CCCN(S(=O)(=O)c2c(Cl)cc(Cl)cc2Cl)C1] | 2-((1-(2,4,6-Trichloro-phenylsulfonyl)piperidin-3-yl)methoxy)-acetic acid |
| S87 | 1 | B | 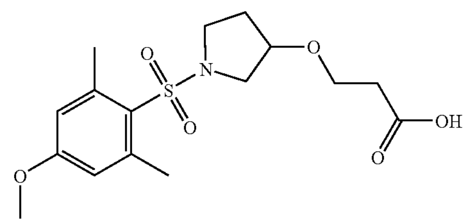 [SMILES: COc1cc(C)c(S(=O)(=O)N2CCC(OCCC(=O)O)C2)c(C)c1] | 3-(1-(4-Methoxy-2,6-dimethylphenylsulfonyl)-pyrrolidin-3-yloxy)-propionic acid |
| S88 | — | — | 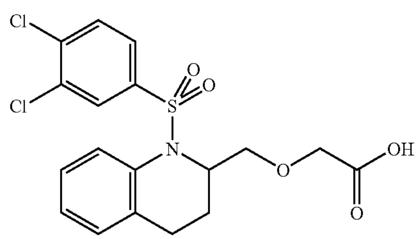 [SMILES: O=C(O)COCC1CCc2ccccc2N1S(=O)(=O)c1ccc(Cl)c(Cl)c1] | 2-((1-(3,4-Dichloro-phenylsulfonyl)-1,2,3,4-tetrahydroquinolin-2-yl)methoxy)-acetic acid |
| S89 | — | — | 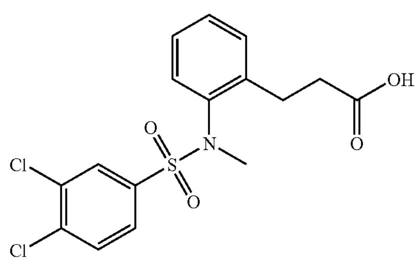 [SMILES: CN(c1ccccc1CCC(=O)O)S(=O)(=O)c1ccc(Cl)c(Cl)c1] | 3-(2-(3,4-Dichloro-N-methylphenylsulfonamide)-phenyl)-propionic acid |
| S90 | — | — | 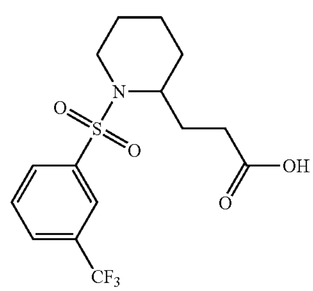 [SMILES: O=C(O)CCC1CCCCN1S(=O)(=O)c1cccc(C(F)(F)F)c1] | 3-(1-(3-(Trifluoromethyl)-phenylsulfonyl)piperidin-2-yl)-propionic acid |
| S91 | — | — | 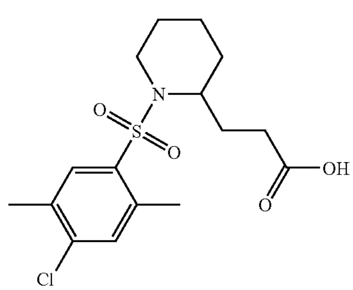 [SMILES: Cc1cc(S(=O)(=O)N2CCCCC2CCC(=O)O)c(C)cc1Cl] | 3-(1-(4-Chloro-2,5-dimethylphenylsulfonyl)-piperidin-2-yl)-propionic acid |

For the synthesis of units S71, S72, S84, S87, bromopropionic acid tert-butyl ester was used in the respective method.

General Preparation of Sulfonylated Acid Units Starting from Amino Alcohols

Method 1

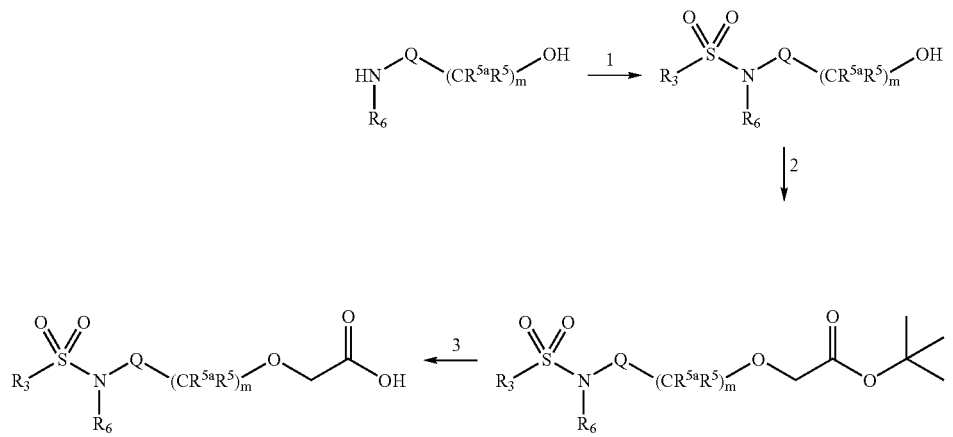

1. Et$_3$N (80 mmol) was added to a solution of the amino alcohol (35 mmol) in CH$_2$Cl$_2$ (200 ml) and the mixture was cooled to 0° C. using an ice-bath. The sulfonyl chloride (32 mmol) was subsequently added and the mixture was stirred for 3 h at RT. After addition of 0.5 M HCl (100 ml), the organic phase was separated off, washed with water, dried over Na$_2$SO$_4$ and filtered and the solvent was removed in vacuo. The crude product was used in the next stage without further purification.

2. n-Bu$_4$NCl (10 mmol) was added to a solution of the product from stage 1 (30 mmol) in toluene (125 ml), the mixture was cooled to 0° C. and first aqueous 35% strength NaOH (150 ml) and then bromoacetic acid tert-butyl ester (45 mmol) in toluene (25 ml) were added dropwise. The reaction mixture was stirred for 3 h, subsequently washed neutral with water and dried with Na$_2$SO$_4$ and the organic solvent was removed in vacuo. The crude product was used in the next stage without further purification or was purified by column chromatography.

General Preparation of Sulfonylated Acid Units Starting from Amino Acids

Method 2

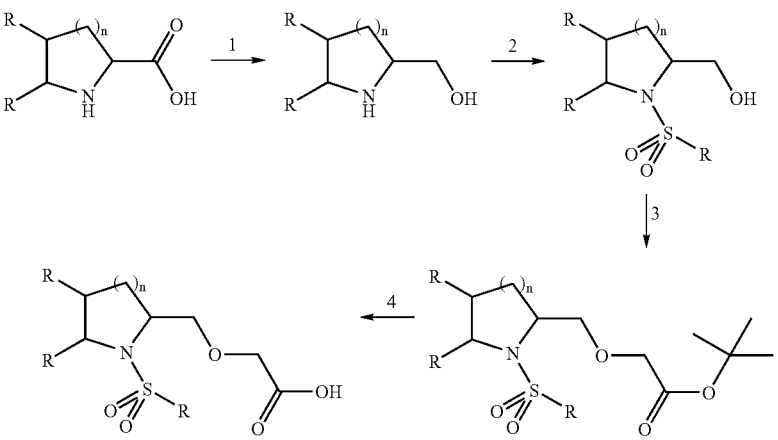

R = H, phenyl, OH, OR$^N$, F, Cl, CF$_3$ or C$_{1-6}$-alkyl

1. LiAlH$_4$ (100 ml, 1.0 M in diethyl ether) was added gradually under an inert gas atmosphere to a suspension of the amino acid (100 mmol) in THF (150 ml), while stirring and at a temperature of between −10° C. and RT. The reaction mixture was stirred for 16 h, during which it warmed up to RT. It was subsequently cooled again to 0° C. and ethyl acetate (20 ml), water (8 ml), 15% strength aqueous NaOH (8 ml) and water (20 ml) were added, while stirring. After filtration, the residue was washed with diethyl ether. The solvent of the combined organic phases was removed in vacuo and the product was employed in the next stage without further purification.

2. Et$_3$N (125 mmol) was added to a solution of the amino alcohol (100 mmol) in CH$_2$Cl$_2$ (200 ml) and the mixture was cooled to 0° C. using an ice-bath. The particular sulfonyl chloride (50 mmol) was subsequently added undiluted or as a solution in CH$_2$Cl$_2$ (100 ml) and the mixture was stirred for 3 h at RT. After addition of 0.5 M hydrochloric acid (100 ml), the organic phase was separated off, washed with water, dried over Na$_2$SO$_4$ and filtered and the solvent was removed in vacuo. The crude product was used in the next stage without further purification or was purified by column chromatography.

3. n-Bu$_4$NCl (10 mmol) was added to a solution of the product from stage 2 (31 mmol) in toluene (200 ml), the mixture was cooled to 0° C. and first aqueous 35% strength NaOH (200 ml) and then bromoacetic acid tert-butyl ester (46 mmol) were added dropwise. The reaction mixture was stirred for 3 h, subsequently washed neutral with water and dried with Na$_2$SO$_4$ and the organic solvent was removed in vacuo. The crude product was used in the next stage without further purification or was purified by column chromatography.

General Preparation of Sulfonylated Acid Units Starting from Amino Alcohols

Method 3

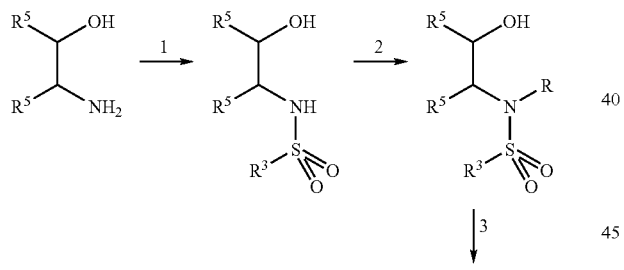

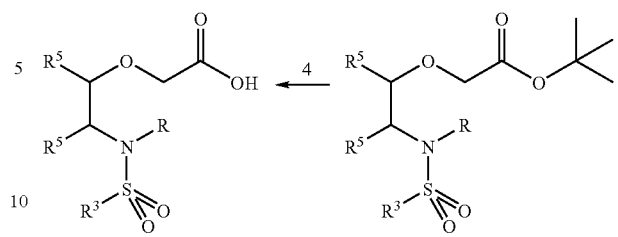

1. Et$_3$N (80 mmol) was added to a solution of the amino alcohol (35 mmol) in CH$_2$Cl$_2$ (200 ml) and the mixture was cooled to 0° C. using an ice-bath. The sulfonyl chloride (32 mmol) was subsequently added and the mixture was stirred for 3 h at RT. After addition of 0.5 M HCl (100 ml), the organic phase was separated off, washed with water, dried over Na$_2$SO$_4$ and filtered and the solvent was removed in vacuo. The crude product was used without further purification.

2. Solid K$_2$CO$_3$ (50 mmol) was added to a solution of the product from stage 1 (26 mmol) and alkyl halide (50 mmol) in acetone (200 ml) and the reaction mixture was stirred overnight at 40° C. After filtration and removal of the solvent, the product was obtained and was either used without further purification or purified via chromatography.

3. n-Bu$_4$NCl (10 mmol) was added to a solution of the product from stage 2 (30 mmol) in toluene (125 ml), the mixture was cooled to 0° C. and first aqueous 35% strength NaOH (150 ml) and then bromoacetic acid tert-butyl ester (45 mmol) in toluene (25) were added dropwise. The reaction mixture was stirred for 3 h, subsequently washed neutral with water and dried with Na$_2$SO$_4$ and the organic solvent was removed in vacuo. The crude product was used in the next stage without further purification or was purified by column chromatography.

Preparation of the Acid Unit Example 58

Method 4

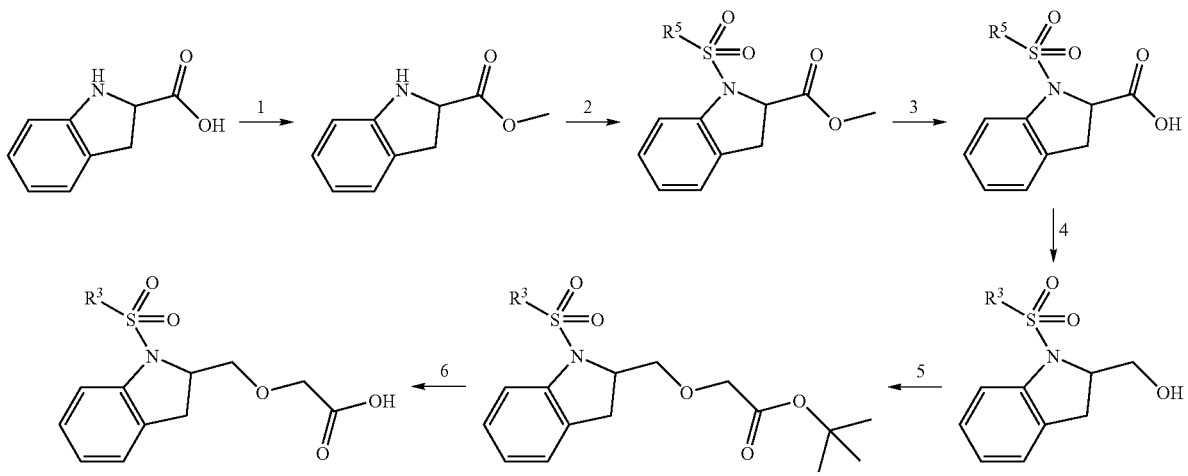

1. A solution of the amino acid (153 mmol) in methanol (500 ml) was cooled to 0° C. and thionyl chloride (168 mmol, 12 ml) was added dropwise. After warming to RT, the reaction solution was heated at 40° C. overnight. After distillation of the solvent, the crude product was obtained, and was employed in the next stage without further working up.

2. Pyridine (459 mmol) and a solution of the sulfonyl chloride (153 mmol) in CH$_2$Cl$_2$ (100 ml) were added to a solution of the methyl ester from stage 1 (152 mmol) in CH$_2$Cl$_2$ (400 ml). The reaction solution was stirred overnight at RT. The solution was diluted with a little CH$_2$Cl$_2$ and washed successively with 0.5 M KHSO$_4$, saturated aqueous NaHCO$_3$ solution and saturated aqueous NaCl solution. The organic phase separated off was dried over Na$_2$SO$_4$, the solvent was removed in vacuo and the crude product was purified by means of column chromatography.

3. 4 M NaOH (153 ml, 610 mmol, 4.5 equivalents) was added, while stirring, to a solution of the product from stage 2 (136 mmol) in a methanol/dioxane/4 M NaOH mixture in the ratio of 15/4/1 (1,020 ml, 203 mmol NaOH, 1.5 equivalents) and the mixture was stirred overnight at RT. The solvent was removed in vacuo. The residue was dissolved with ethyl acetate and the solution was washed with 0.5 M KHSO$_4$. The organic phase was washed with saturated aqueous NaCl solution and the separated organic phase was dried, after filtration, with Na$_2$SO$_4$. After removal of the solvent in vacuo and washing with diethyl ether, the purified product from stage 3 was obtained.

4. BH$_3$ x DMS (2.0 M in THF, 31.2 ml, 63 mmol) was slowly added dropwise to a solution of the product from stage 3 (31 mmol) in THF (250 ml) at 0° C., while stirring. After stirring for 30 min at RT, the solution was allowed to warm to RT slowly overnight. Methanol was subsequently added slowly until no further gas was released, and the solvent was reduced in vacuo. The crude product was filtered over silica and washed with CH$_2$Cl$_2$/methanol in the ratio of 9/1.

5. n-Bu$_4$NCl (10 mmol, 2.9 g) was added to a solution of the product from stage 4 (31 mmol) in toluene (175 ml), the mixture was cooled to 0° C. and first aqueous 35% strength NaOH (200 ml) and then bromoacetic acid tert-butyl ester (48 mmol, 7 ml) were added dropwise. The reaction mixture was stirred for 3 h, subsequently washed neutral with water and dried with Na$_2$SO$_4$ and the organic solvent was removed in vacuo. The crude product was used in the next stage without further purification.

6. The product from stage 5 (30 mmol) was dissolved in a mixture of MeOH/dioxane/4 M NaOH in the ratio of 15/4/1 (236 ml, 47 mmol NaOH), further NaOH (4 M, 35 ml, 141 mmol) was added and the mixture was stirred overnight at RT. The solvent was reduced in vacuo, the residue was diluted with ethyl acetate and the mixture was washed with 0.5 M KHSO$_4$. The organic phase was separated off, washed with saturated aqueous NaCl solution and dried with Na$_2$SO$_4$. After filtration, the solvent was removed in vacuo. The crude product was purified by co-evaporation with diethyl ether and CH$_2$Cl$_2$.

Preparation of the acid unit S56

Method 5

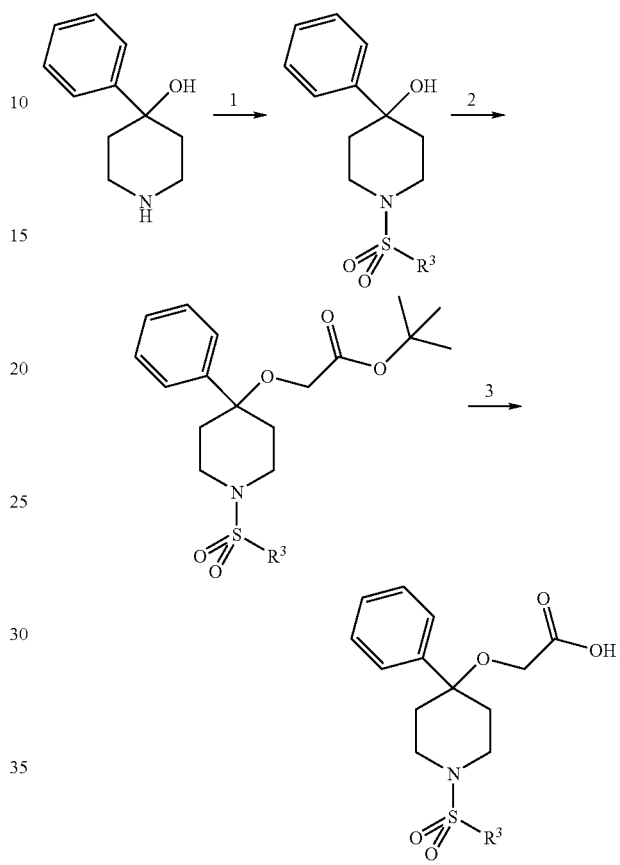

1. Et$_3$N (176 mmol) was added to a solution of the amino alcohol (70.5 mmol) in CH$_2$Cl$_2$ (300 ml), while stirring. After cooling to 0° C., the sulfonyl chloride (70.5 mmol), diluted with CH$_2$Cl$_2$ (100 ml), was slowly added dropwise and the mixture was stirred for 3 h at RT. After addition of HCl (0.5 M, 140 ml), the organic phase was separated off, washed with water, dried over Na$_2$SO$_4$ and filtered and the solvent was removed in vacuo.

2. A solution of stage 1 (58.6 mmol) in THF (200 ml) was added dropwise to a suspension of NaH (60% strength dispersion in mineral oil, 88 mmol) in THF (75 ml) at 0° C. The reaction mixture was then warmed to RT and heated under reflux for 1.5 h. After cooling to RT, bromoacetic acid tert-butyl ester (12.8 ml, 88 mmol) was added dropwise. After stirring overnight at RT, NH$_4$Cl/water (1/1, 200 ml) was added to the reaction mixture and the mixture was extracted with ethyl acetate (500 ml). After drying of the organic phase with Na$_2$SO$_4$ and filtration, the solvent was removed in vacuo and the product was purified via column chromatography.

3. Aqueous NaOH (6 M, 170 ml, 1.02 mol) was added to a solution of stage 2 (40.8 mmol), dissolved in MeOH (85 ml) and dioxane (85 ml), and the mixture was stirred overnight at RT. After cooling to 0° C., HCl (6 M, 190 ml) was added slowly. The reaction mixture was then extracted with CH$_2$Cl$_2$ (2×200 ml), the combined organic phases were dried over Na$_2$SO$_4$ and filtered and the solvent was removed in vacuo. Diisopropyl ether was added to the residue and the solid was filtered off and washed with diethyl ether.

Preparation of the Acid Unit S57

Method 6

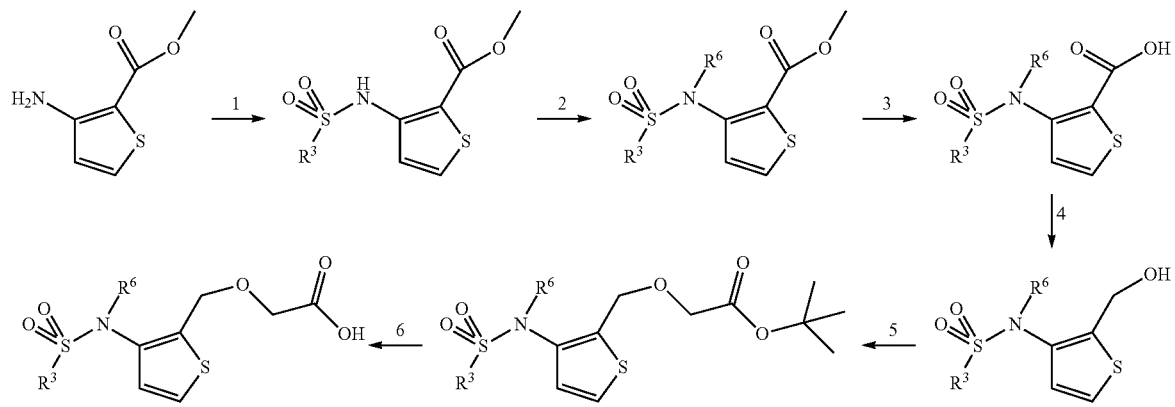

1. Pyridine (105 mmol, 1.5 equivalents) was added to a solution of methyl 3-aminothiophene-2-carboxylate (70 mmol) in CH$_2$Cl$_2$ (200 ml) and a solution of the sulfonyl chloride (105 mmol) in CH$_2$Cl$_2$ (150 ml) was subsequently added dropwise at 0° C. After stirring overnight at RT, the reaction mixture was diluted with CH$_2$Cl$_2$ (150 ml) and washed successively with 0.5 M KHSO$_4$ (500 ml), aqueous saturated NaHCO$_3$ solution (500 ml) and saturated aqueous NaCl solution (500 ml). The separated organic phase was dried over Na$_2$SO$_4$ and filtered. After removal of the solvent in vacuo, the residue was recrystallized in methanol.
2. Alkyl halide (69 mmol) was added to a solution of the sulfonamide of stage 1 (53 mmol) in acetone (350 ml) and K$_2$CO$_3$ (106 mmol) and the suspension was stirred at 40° C. overnight. The reaction mixture was filtered and the solvent of the filtrate was removed in vacuo. The residue was purified by recrystallization from methanol.
3. 4 M NaOH (25 ml, 100 mmol, 4.5 equivalents) was added to a solution of the methyl ester from stage 2 (22 mmol) in MeOH/dioxane/4 M NaOH (15/4/1) (165 ml, 33 mmol NaOH, 1.5 equivalents) and the reaction mixture was stirred at RT overnight. The solvent was removed in vacuo and the residue was taken up in ethyl acetate (800 ml). After washing with 0.5 M KHSO$_4$ (800 ml), the aqueous phase separated off was washed with ethyl acetate (2×200 ml). The combined organic phases were extracted with aqueous saturated NaCl solution (800 ml) and dried over Na$_2$SO$_4$. After filtration, the solvent was removed in vacuo and the product was employed in the next stage without further purification.
4. BH$_3$ x DMS (2 M, 15 ml, 30.6 mmol, 1.3 equivalents) was slowly added to a solution of the acid stage 3 (23.5 mmol) in THF (150 ml) at RT, while stirring. The reaction solution was heated under reflux for 5 h. After cooling to RT, methanol was slowly added until no further evolution of gas took place. The solvent was largely removed in vacuo, the residue was filtered off over silica and the product was employed in the next stage without further purification.
5. n-Bu$_4$NCl (7.35 mmol) was added to a solution of the product from stage 4 (22 mmol) in CH$_2$Cl$_2$ (90 ml), the mixture was cooled to 0° C., aqueous 35% strength NaOH (90 ml) was first added and bromoacetic acid tert-butyl ester (33.4 mmol) was then added dropwise. The reaction mixture was stirred for 3 h, CH$_2$Cl$_2$ (500 ml) was subsequently added and the mixture was extracted with water (3×500 ml). After separation and drying of the organic phase with Na$_2$SO$_4$, the solvent was removed in vacuo and the residue was co-evaporated with diisopropyl ether. Heptane was added to the crude product and the product was filtered off and used in the next stage without further purification.
6. The product from stage 5 (21 mmol) was dissolved in a mixture of MeOH/dioxane/4 M NaOH in the ratio of 15/4/1 (160 ml, 32 mmol NaOH), further NaOH (4 M, 35 ml, 96 mmol) was added and the mixture was stirred for 3 h at RT. The solvent was reduced in vacuo, the residue was diluted with ethyl acetate (800 ml) and the mixture was washed with 0.5 M KHSO$_4$ (800 ml). The aqueous phase was extracted with ethyl acetate (200 ml). The combined organic phases were separated off, washed with saturated aqueous NaCl solution (800 ml) and dried with Na$_2$SO$_4$. After filtration, the solvent was removed in vacuo. The crude product was purified by co-evaporation with CH$_2$Cl$_2$.

Method 7

1. K$_2$CO$_3$ (148 mmol) and the sulfonyl chloride (82 mmol) were added at RT to a solution or suspension of the amino alcohol (74 mmol) in acetone (350 ml) and the mixture was stirred overnight at 40-50° C. The reaction mixture was cooled to RT and filtered. The solvent of the filtrate was then removed in vacuo. The crude product was used in the next stage without further working up.
2. n-Bu$_4$NCl (10 mmol) was added to a solution of the product from stage 1 (31 mmol) in toluene (200 ml), the mixture was cooled to 0° C., and first aqueous 35% strength NaOH (200 ml) and then bromoacetic acid tert-butyl ester (46 mmol) were added dropwise. The reaction mixture was stirred for 3 h and then washed neutral with water, dried with Na$_2$SO$_4$ and filtered, and the organic solvent was removed in vacuo. The crude product was used in the next stage without further purification or was purified by column chromatography.

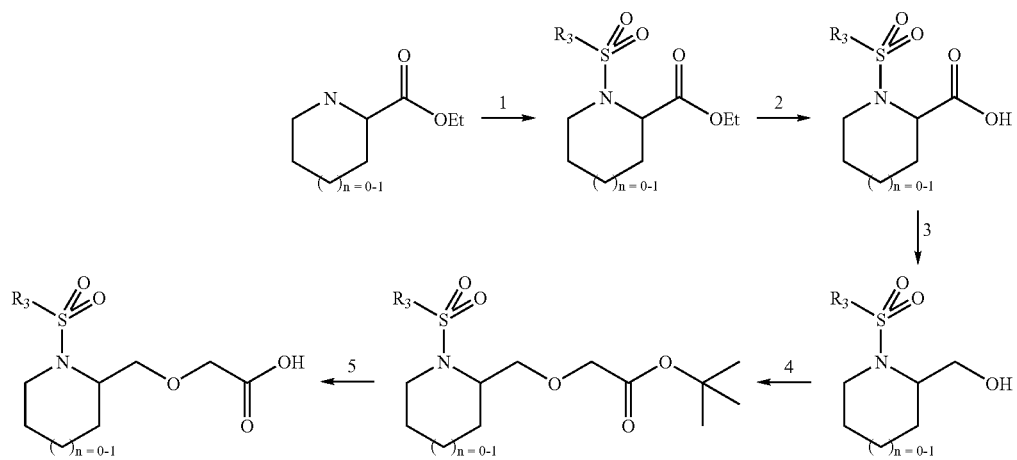

Preparation of 2-((1-(2,6-dichloro-4-(trifluoromethyl)phenylsulfonyl)piperidin-2-yl)methoxy)-acetic acid S69

1. Et₃N (95 mmol) was added to a suspension of DL-piperidine-2-carboxylic acid ethyl ester (38 mmol) in CH₂Cl₂ (150 ml). The solution was cooled to 0° C., the sulfonyl chloride (42 mmol) in a solution of CH₂Cl₂ (30 ml) was slowly added dropwise, and the mixture was stirred for 2 h at RT. The organic phase was extracted with 1 M HCl (250 ml) and H₂O (250 ml). The organic phase separated off was dried over Na₂SO₄. The solvent was removed in vacuo. The residue was co-evaporated with i-propyl ether and the product was used in the next stage without further working up.
2. 4 M NaOH (113 mmol) was added at RT, while stirring, to a solution of the ester (38 mmol) in a solvent mixture of methanol/dioxane/4 M NaOH (15/4/1) (57 mmol NaOH), and the mixture was stirred for 2 h. The organic solvent was removed in vacuo, and the residue was diluted with ethyl acetate (300 ml) and extracted with 1 M KHSO₄ (300 ml). The organic phase was washed with saturated NaCl solution (200 ml). The organic phase separated off was dried over Na₂SO₄ and filtered, and the solvent was removed in vacuo. The product was used in the next stage without further purification.
3. 2 M BH₃ x DMS in THF (82 mmol) was slowly added at 0° C., while stirring, to a solution of the carboxylic acid (27 mmol) in THF (135 ml). After cooling further for 30 min, the mixture was stirred overnight at RT. Removal of the solvent yielded the crude product, which was used in the next stage without further purification.
4. n-Bu₄NCl (8.8 mmol) was added to a solution of bromoacetic acid tert-butyl ester (40 mmol) in toluene (100 ml). The reaction mixture was cooled to 0° C., and 35% strength NaOH (150 ml) and then, dropwise, the alcohol (27 mmol) dissolved in toluene (50 ml) were added. After stirring for 1.5 h at RT, the organic phase was separated and subsequently washed with water (4×150 ml) and with saturated NaCl solution (150 ml). The organic phase separated off was dried over Na₂SO₄ and filtered, and then the solvent was removed in vacuo. The crude product was purified by column chromatography.
5. The tert-butyl ester (16 mmol) was stirred overnight at RT in 4 M HCl in dioxane (70 ml, 27 mmol). After removal of the solvent, the crude product was purified by column chromatography.

Preparation of 2-((1-(2,6-dichloro-4-(trifluoromethyl)phenylsulfonyl)pyrrolidin-2-yl)methoxy)-acetic acid S76

1. Et₃N (181 mmol) was added to a suspension of DL-pyrrolidine-2-carboxylic acid methyl ester hydrochloride (36 mmol) in CH₂Cl₂ (180 ml). The solution was cooled to 0° C., the sulfonyl chloride (40 mmol) in a solution of CH₂Cl₂ (30 ml) was slowly added dropwise, and the mixture was stirred for 2 h at RT. The organic phase was extracted with 1 M HCl (250 ml), H₂O (250 ml). The organic phase separated off was dried over Na₂SO₄. The solvent was removed in vacuo. The residue was co-evaporated with i-propyl ether and the product was used in the next stage without further working up.
2. 4 M NaOH (108 mmol) was added at RT, while stirring, to a solution of the ester (36 mmol) in a solvent mixture of methanol/dioxane/4 M NaOH (15/4/1) (54 mmol NaOH), and the mixture was stirred for 2 h. The organic solvent was removed in vacuo, and the residue was diluted with ethyl acetate (300 ml) and extracted with 1 M KHSO₄ (300 ml). The organic phase was washed with saturated NaCl solution (200 ml). The organic phase separated off was dried over Na₂SO₄ and filtered, and the solvent was removed in vacuo. The product was used in the next stage without further purification.
3. 2 M BH₃ x DMS in THF (86 mmol) was slowly added at 0° C., while stirring, to a solution of the carboxylic acid (28 mmol) in THF (140 ml). After cooling further for 30 min, the mixture was stirred overnight at RT. Removal of the solvent yielded the crude product, which was used in the next stage without further purification.
4. n-Bu₄NCl (9 mmol) was added to a solution of bromoacetic acid tert-butyl ester (42 mmol) in toluene (100 ml). The reaction mixture was cooled to 0° C., and 35% strength NaOH (150 ml) and then, dropwise, the alcohol (28 mmol) dissolved in toluene (50 ml) were added. After stirring for 1.5 h at RT, the organic phase was separated off and extracted with water (4×150 ml) and with saturated NaCl solution (150 ml). The organic phase separated off was dried over Na₂SO₄ and filtered, and then the solvent was removed in vacuo. The crude product was purified by column chromatography.
5. The tert-butyl ester (16 mmol) was stirred overnight at RT in 4 M HCl in dioxane (70 ml, 27 mmol). After removal of the solvent, the crude product was purified by column chromatography.

Preparation of 2-(2-(N-(cyclopropylmethyl)-4-methoxy-2,3,6-trimethylphenylsulfonamide)ethoxy)-acetic acid S78

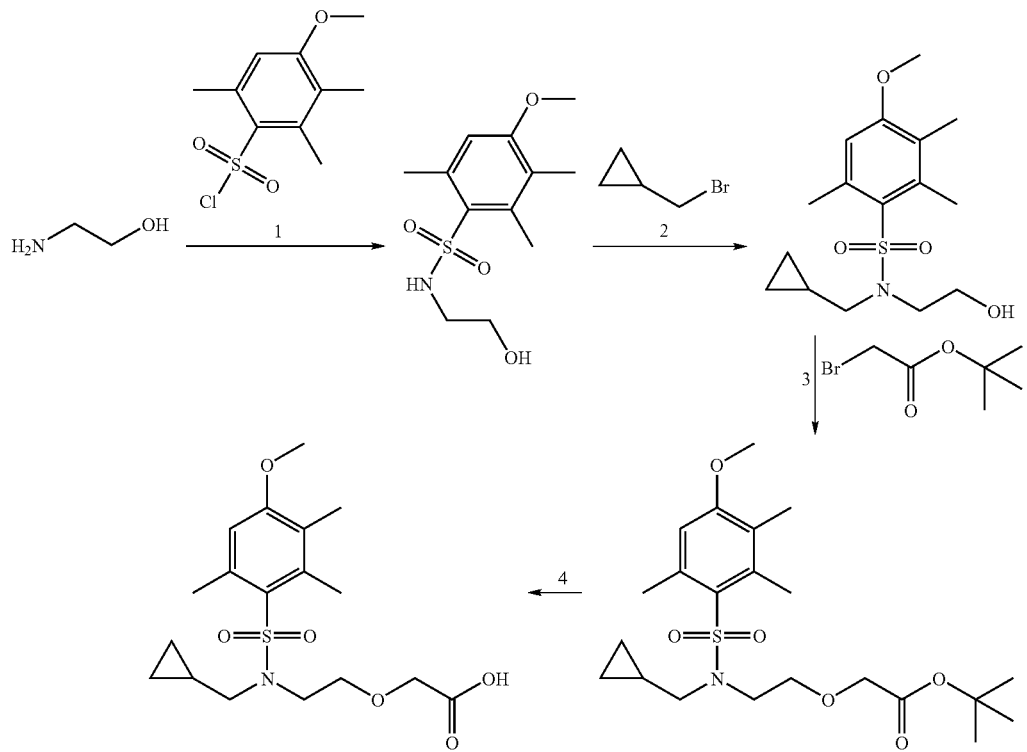

1. Et$_3$N (42.4 ml, 302 mmol) was added to a solution of aminoethanol (8.01 ml, 133 mmol) in CH$_2$Cl$_2$ (200 ml), and the solution was cooled to 0° C. A solution of the sulfonyl chloride (30.0 g, 121 mmol) in CH$_2$Cl$_2$ (200 ml) was added dropwise. The reaction mixture was then stirred overnight at RT. After addition of 1 M HCl (125 ml), the organic phase was separated off, washed with water and dried over Na$_2$SO$_4$. After filtration, the solvent was removed in vacuo.

2. NaH (60% dispersion in mineral oil, 1.69 g, 42.2 mmol) was added in portions to a solution of the sulfonamide (11.0 g, 38.69 mmol) in THF (100 ml). After stirring for 15 min, a solution of the alkyl halide (10.87 g, 80.5 mmol) in THF (50 ml) was added dropwise, and the reaction mixture was heated under reflux overnight. After cooling to RT, further NaH (60% dispersion in mineral oil, 0.34 g, 8.5 mmol) and alkyl halide (4.09 g, 30.3 mmol) were added, and the mixture was heated under reflux overnight. After cooling to RT, aqueous saturated NH$_4$Cl solution was added. The aqueous phase was separated off and extracted with ethyl acetate (100 ml). The combined organic phases were dried over Na$_2$SO$_4$. After filtration and removal of the solvent in vacuo, the product was purified by column chromatography (silica, heptane/ethyl acetate 3:1). Yield: 8.88 g, 70%

3. n-Bu$_4$NCl (2.51 g, 9.04 mmol) was added to a solution of the alkylated sulfonamide (8.88 g, 27.1 mmol) in toluene (100 ml) and CH$_2$Cl$_2$ (100 ml). After cooling to 0° C., 35% strength NaOH (175 ml) and then, dropwise, bromoacetic acid tert-butyl ester (5.93 ml, 40.7 mmol) were added. The reaction mixture was stirred for 3 h at RT. The organic phase separated off was washed with H$_2$O (3×150 ml), dried over Na$_2$SO$_4$ and after filtration removed in vacuo. The product was purified by column chromatography (silica, heptane/ethyl acetate 4:1). Yield: 11.33 g, 95%

4. 6 M NaOH (1100 ml, 600 mmol) was added to a solution of the tert-butyl ester (11.30 g, 25.6 mmol) in THF (100 ml) and MeOH (100 ml), and the reaction mixture was stirred for 1 h at RT. The organic phase was then removed in vacuo, and 6 M HCl (125 ml) was added at 0° C. The aqueous phase was extracted with ethyl acetate (2×100 ml). The combined organic phases were dried over Na$_2$SO$_4$. After filtration and removal of the solvent, the product was co-evaporated in each case twice with toluene, CH$_2$Cl$_2$ and Et$_2$O. Yield: 9.52 g, 97%

Preparation of 2-(2-(N-isobutyl-4-methoxy-2,3,6-trimethylphenylsulfonamide)ethoxy)-acetic acid S79

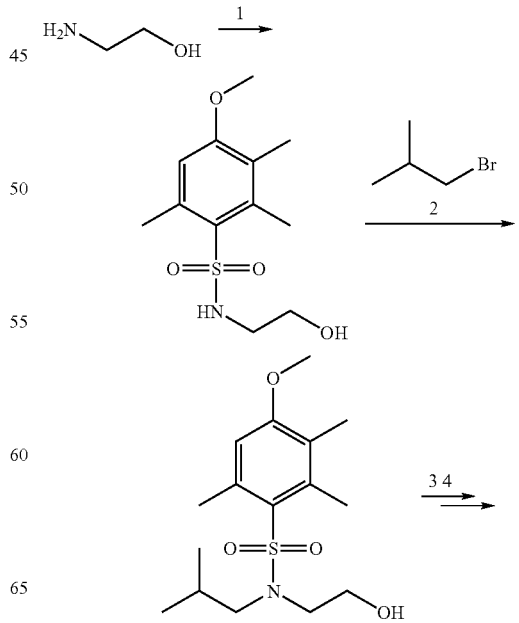

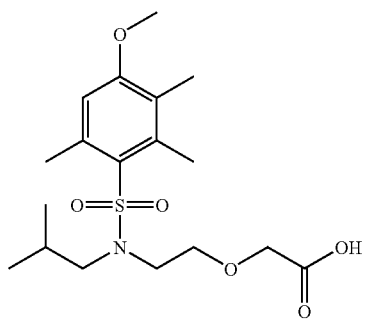

1. Stage 1 of the preparation of 2-(2-(N-isobutyl-4-methoxy-2,3,6-trimethylphenylsulfonamide)-ethoxy)-acetic acid S79 was carried out analogously to the preparation of unit S78.

2. K₂CO₃ (11.11 g, 80.4 mmol) and the alkyl halide (43.7 ml, 402 mmol) were added in succession to a solution of the sulfonamide (11.0 g, 38.69 mmol) in acetonitrile (400 ml), and the mixture was heated under reflux overnight. Further alkyl halide (9 ml, 201 mmol) was then added, and the mixture was heated under reflux overnight. After cooling to RT, the mixture was filtered off over Celite and the solvent was removed in vacuo. The product was purified by column chromatography (silica, heptane/ethyl acetate 2:1). Yield: 8.30 g, 63%

3-4. Stages 3 and 4 in the preparation of 2-(2-(N-isobutyl-4-methoxy-2,3,6-trimethylphenyl-sulfonamide)ethoxy)-acetic acid S79 also were carried out analogously to the preparation of unit S78.

Preparation of 2-((1-(2,4,6-trichlorophenylsulfonyl)pyrrolidin-3-yl)methoxy)-acetic acid S80

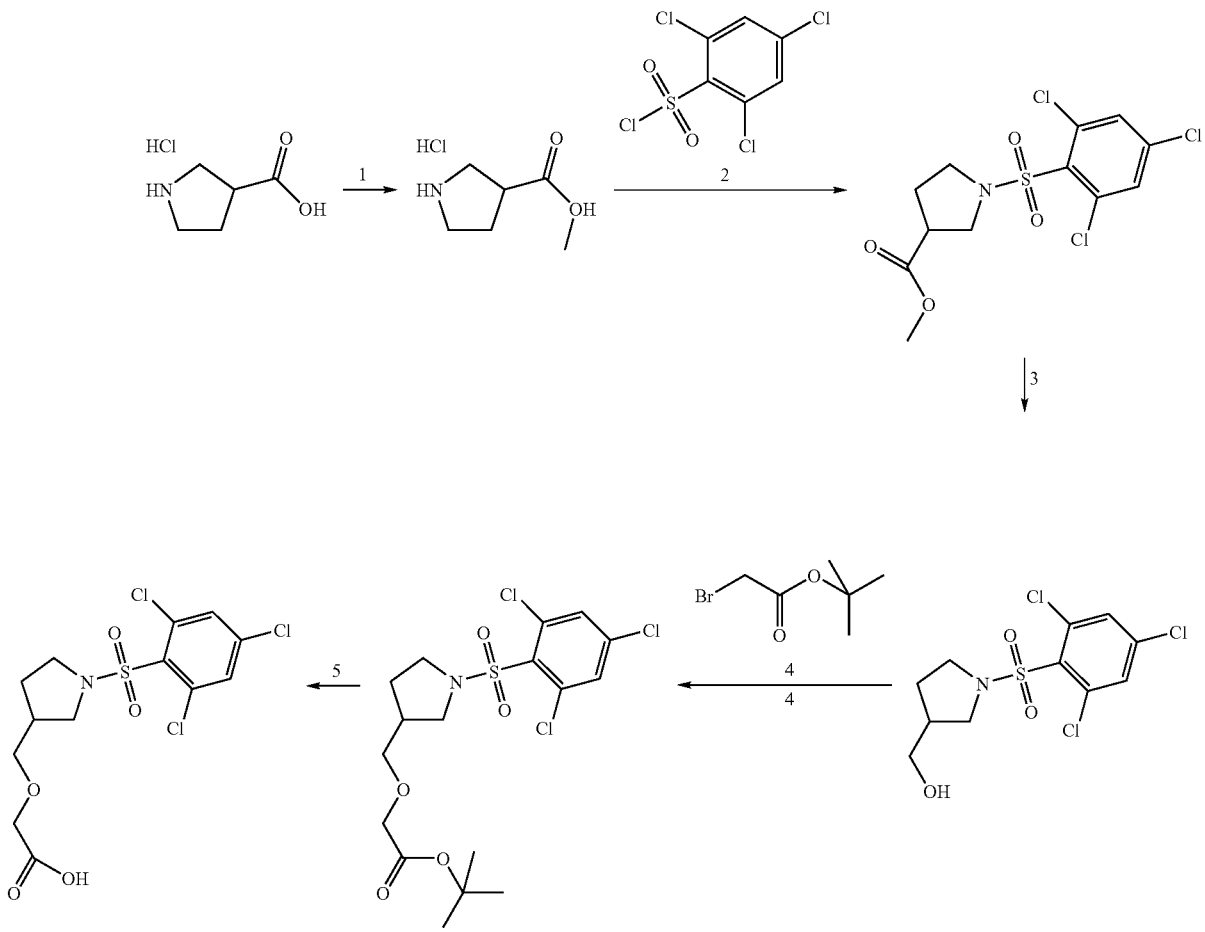

1. SOCl$_2$ (8.70 ml, 119 mmol) was added dropwise at 0° C. to methanol (450 ml). β-Proline hydrochloride (9.03 g, 59.6 mmol) was then added in portions, and the reaction mixture was stirred overnight at 40° C. The solvent was removed and the product was used in the next stage without further working up.

2. Et$_3$N (41.9 ml, 298 mmol) was added to a solution of the amino ester as the hydrochloride (11.5 g, 59.6 mmol) in CH$_2$Cl$_2$ (250 ml). After cooling to 0° C., the sulfonyl halide (16.7 g, 59.6 mmol) in CH$_2$Cl$_2$ (200 ml) was added dropwise. The reaction mixture was stirred for 1 h at RT, and 1 M HCl (200 ml) was added. The organic phase separated off was washed with H$_2$O and dried over Na$_2$SO$_4$. After filtration and removal of the solvent, the product was purified by column chromatography (silica, heptane/ethyl acetate 3:1). Yield: 21.50 g, 97%

3. The sulfonylated amino ester (21.07 g, 56.5 mmol) dissolved in THF (100 ml) was added dropwise at −20° C. to a suspension of LiAlH$_4$ (85 ml, 1.0 M in THF, 85 mmol) in THF (250 ml). The reaction mixture was stirred for 1 h at −20° C., H$_2$O (30 ml) was added, and the mixture was warmed to RT. After addition of 1 M HCl (200 ml) and ethyl acetate (300 ml), the organic phase was separated off and washed with aqueous saturated NaCl solution and dried over Na$_2$SO$_4$. Filtration and removal of the solvent yielded the product, which was used in the next stage without further working up.

4. n-Bu$_4$NCl was added to a solution of the alcohol (23.0 g, 56.5 mmol) in toluene (200 ml). After cooling to 0° C., 35% strength NaOH (250 ml) and bromoacetic acid tert-butyl ester (12.4 ml, 84.8 mmol) were added. The reaction mixture was stirred for 3 h at RT. The organic phase was separated off and washed with H$_2$O (3×150 ml). After drying over Na$_2$SO$_4$ and filtration, the solvent was removed in vacuo. The product was purified by column chromatography (silica, heptane/ethyl acetate 9:1-7:1). Yield: 13.4 g, 52%

5. The ester cleavage and preparation of 2-((1-(2,4,6-trichlorophenylsulfonyl)pyrrolidin-3-yl)methoxy)-acetic acid 80 was carried out according to Variant A.

Preparation of 2-((1-(3,4-dichlorophenylsulfonyl)-1,2,3,4-tetrahydroquinolin-2-yl)methoxy)acetic acid S88

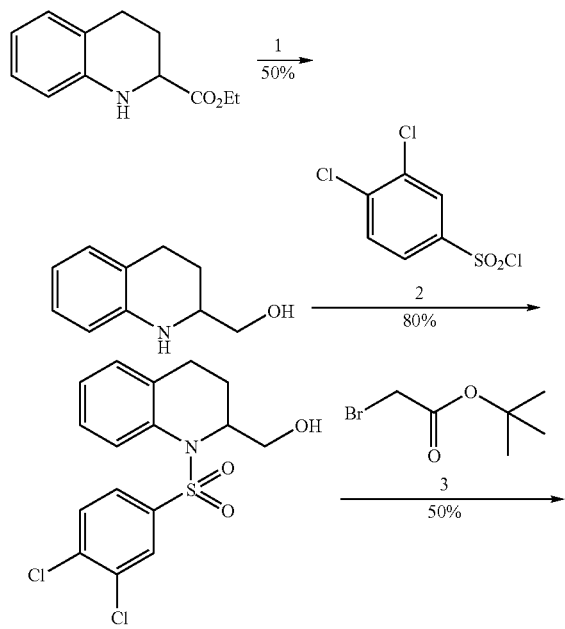

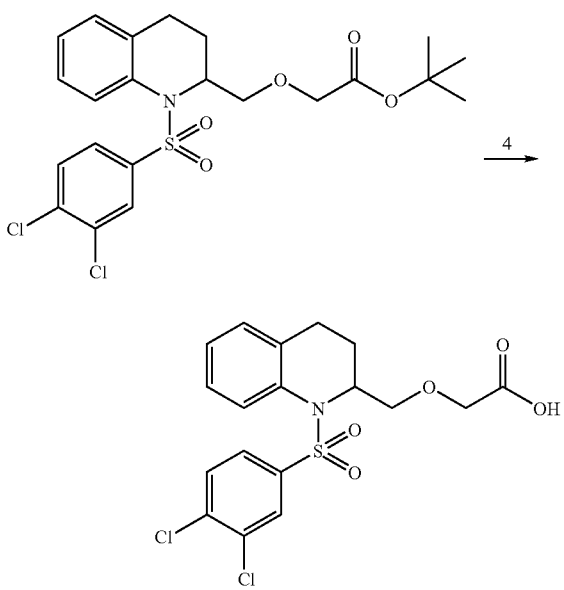

1. 1,2,3,4-Tetrahydroquinoline-2-carboxylic acid ethyl ester (25 mmol) in THF (5 ml/mol) was added dropwise at 0° C. to a suspension of LAH (2 eq.) in THF (50 ml). The reaction mixture was stirred for 1 h at RT and then heated under reflux for 4 h. After addition of aqueous saturated Na$_2$SO$_4$ solution, the mixture was filtered and the organic solvent was removed in vacuo. The product was purified by column chromatography (3:7 ethyl acetate/hexane). Yield: 50%

2. Pyridine (5 eq.), DMAP (0.5 eq.) and 3,4-dichlorobenzenesulfonyl chloride (1.2 eq.) dissolved in CH$_2$Cl$_2$ (50 ml) were added to a suspension, cooled to 0° C., of the alcohol (16 mmol) in CH$_2$Cl$_2$ (5 ml/mmol). After stirring for 5 h at 0° C., CH$_2$Cl$_2$ was added and the mixture was washed with aqueous copper sulfate solution, water and saturated NaCl solution. After drying over sodium sulfate and filtration, the solvent was removed in vacuo. The product was purified by column chromatography (5:95 ethyl acetate/CH$_2$Cl$_2$). Yield: 80%

3. A solution of the sulfonamide (16 mmol) dissolved in THF (100 ml) was added dropwise, while stirring, to a suspension, cooled to 0° C., of NaH (2 eq.) in THF (300 ml). After stirring for 45 min at that temperature, a solution of bromoacetic acid tert-butyl ester (1.5 eq.) in THF (50 ml) was added. The reaction mixture was heated for 20 h at 50° C. It was then cooled to 0° C., ice was added, and extraction with ethyl acetate was carried out. The organic phase was washed with aqueous saturated NaCl solution and dried over Na$_2$SO$_4$. After filtration, the solvent was removed in vacuo. The product was purified by column chromatography (1:9 ethyl acetate/hexane). Yield: 50%

4. TFA (13 eq.) was added at a temperature of 0° C., while stirring, to a solution of the tert-butyl ester (1 eq.) in CH$_2$Cl$_2$ (10 ml/mmol). After stirring for 3 h at 0° C., the solvent was removed in vacuo. The crude product was used without further working up.

Preparation of 3-(2-(3,4-dichloro-N-methylphenyl-sulfonamide)phenyl)-propionic acid S89

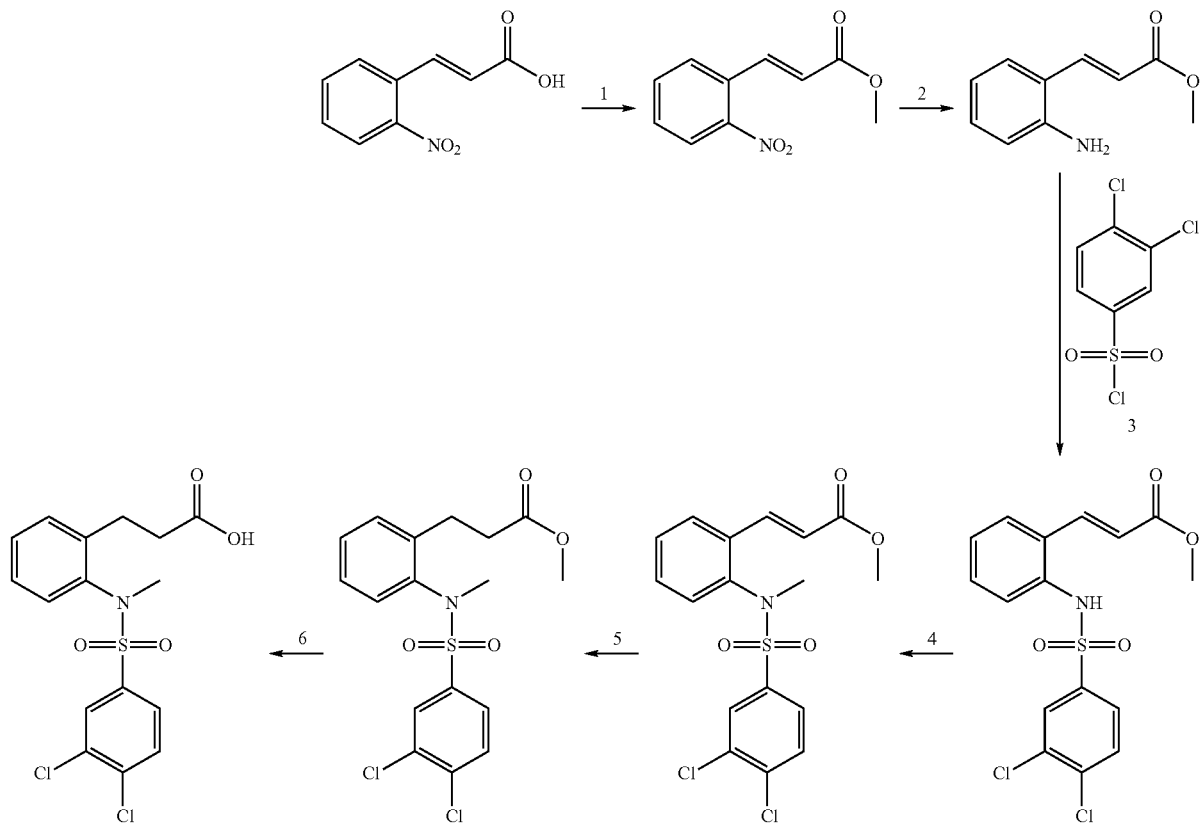

1. H$_2$SO$_4$ (27.4 ml, 514.6 mmol) was added to a solution of 3-(2-nitrophenyl)acrylic acid (49.7 g, 257.3 mmol) in MeOH (1000 ml), and the reaction mixture was heated at reflux overnight. After cooling to RT, the solvent was removed in vacuo and the residue was dissolved in CH$_2$Cl$_2$ (750 ml). The organic phase was extracted with aqueous saturated NaHCO$_3$ solution (500 ml) and with aqueous saturated NaCl solution (500 ml). Drying over Na$_2$SO$_4$ and removal of the solvent yielded the product, which was used in the next stage without further working up.

2. The ester (50.3 g, 242.8 mmol) was stirred, under N$_2$, into HOAc (500 ml), the mixture was cooled to 0° C., and iron powder (54.2 g, 971 mmol) was added in portions. Stirring was then carried out for 3 h at RT. The solvent was removed in vacuo and the residue was taken up in ethyl acetate (750 ml) and washed neutral with aqueous saturated NaHCO$_3$ solution. The organic phase was washed with aqueous saturated NaCl solution (500 ml) and dried over Na$_2$SO$_4$. Removal of the solvent yielded the product, which was used in the next stage without further working up. Yield: 42.7 g, 99%

3. Pyridine (53.2 ml, 653.3 mmol) and then a solution of the sulfonyl chloride (80.2 g, 326.7 mmol) in CH$_2$Cl$_2$ (200 ml) were added to a solution of the aniline ester (38.6 g, 217.8 mmol) in CH$_2$Cl$_2$ (550 ml), and the reaction mixture was stirred overnight at RT. CH$_2$Cl$_2$ (200 ml) was added to the solution, and the mixture was washed with aqueous 0.5 M KHSO$_4$ solution (500 ml), aqueous saturated NaHCO$_3$ solution (500 ml) and aqueous saturated NaCl solution (500 ml). After drying over Na$_2$SO$_4$, the solvent was removed in vacuo. After addition of ethyl acetate, the solid material was filtered off and washed with a small amount of ethyl acetate. Further purification was carried out by column chromatography (silica, CH$_2$Cl$_2$ to CH$_2$Cl$_2$/MeOH 98:2). Yield: 21.7 g, 26%

4. The sulfonamide (21.4 g, 55.4 mmol) and MeI (17.2 ml, 277.0 mmol) were dissolved in acetone (350 ml); K$_2$CO$_3$ (15.3 g, 110.8 mmol) was added, and the reaction mixture was stirred overnight at 40° C. After filtration, the filtrate was concentrated and again filtered over silica. Addition of CH$_2$Cl$_2$ and removal of the solvent yielded the product. Yield: 21.3 g, 96%

5. The methyl ester (21.3 g, 53.2 mmol) dissolved in THF (350 ml) was hydrogenated in an autoclave with a catalytic amount of PtO$_2$ (480 mg, 2.1 mmol) for 90 min at 30° C. (H$_2$, 1 bar). After cooling to RT, the suspension was filtered off over Celite and washed with ethyl acetate. The solvent of the filtrate was removed in vacuo. The product was used in the next stage without further working up. Yield: 20.4 g, 95%

6. 4 M NaOH (57 ml, 227 mmol, 4.5 eq.) was added to a solution of the methyl ester (20.3 g, 50.5 mmol) in MeOH/dioxane/4 M NaOH (15/4/1) (380 ml, 75.7 mmol NaOH, 1.5 eq.), and the solution was stirred for 2 h at RT. After removal of the solvent, the residue was dissolved in ethyl acetate (500 ml) and washed with aqueous saturated 1 M KHSO$_4$ solution (500 ml). The aqueous phase was extracted with ethyl acetate (2×250 ml). The combined organic phases were washed with aqueous saturated NaCl solution (500 ml) and dried over Na$_2$SO$_4$. Filtration and removal of the solvent yielded the product, which was used without further working up. Yield: 18.3 g, 93%

Preparation of 3-(1-(3-(trifluoromethyl)phenylsulfonyl)piperidin-2-yl)-propionic acid S90

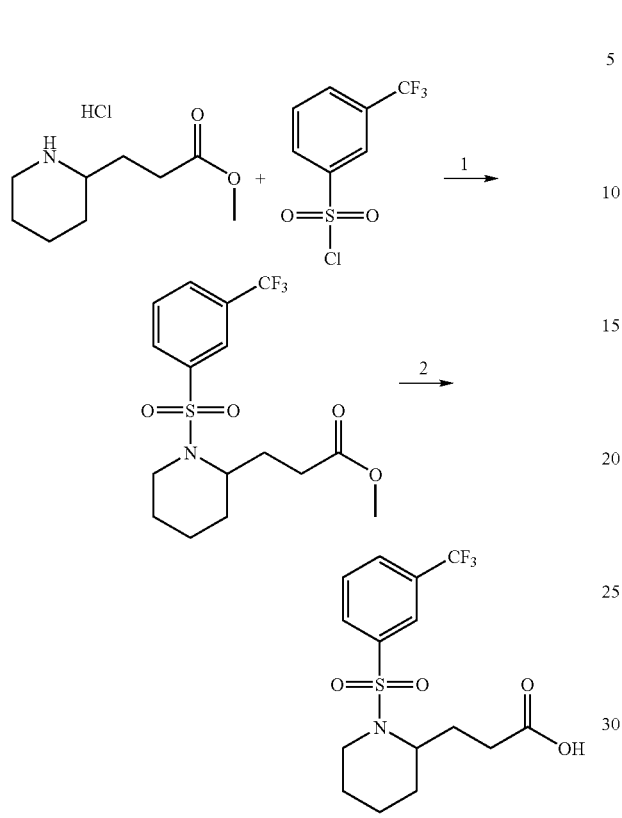

1. A solution of Et₃N (15.4 ml, 110 mmol) in CH₂Cl₂ (150 ml) was added at 0° C. to a solution of the aminomethyl ester hydrochloride (9.11 g, 43.9 mmol) and 3-(trifluoromethyl)-benzenesulfonyl chloride (10.73 g, 43.9 mmol) in CH₂Cl₂ (150 ml), and stirring was carried out for 1 h at 0° C. and for 2 h at RT. The reaction mixture was washed with 1 M HCl (300 ml), and the organic phase separated off was dried over Na₂SO₄. After filtration, the solvent was removed in vacuo and the product was purified by column chromatography (silica, heptane/ethyl acetate, 4:1). Yield: 13.76 g, 83%

2. 6 M NaOH (110 ml) was added to a solution of the ester (13.76 g, 36.3 mmol) in THF (110 ml) and MeOH (110 ml), and the mixture was stirred for 1 h. After removal of the solvent, 6 M HCl (115 ml) was again added at 0° C. After extraction with ethyl acetate (500 ml) and drying over Na₂SO₄, the solvent was removed in vacuo and the residue was co-evaporated three times with i-Pr₂O. Yield: 13.25 g, 100%

Preparation of 3-(1-(4-chloro-2,5-dimethylphenylsulfonyl)piperidin-2-yl)-propionic acid S91

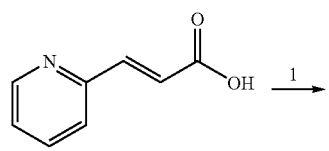

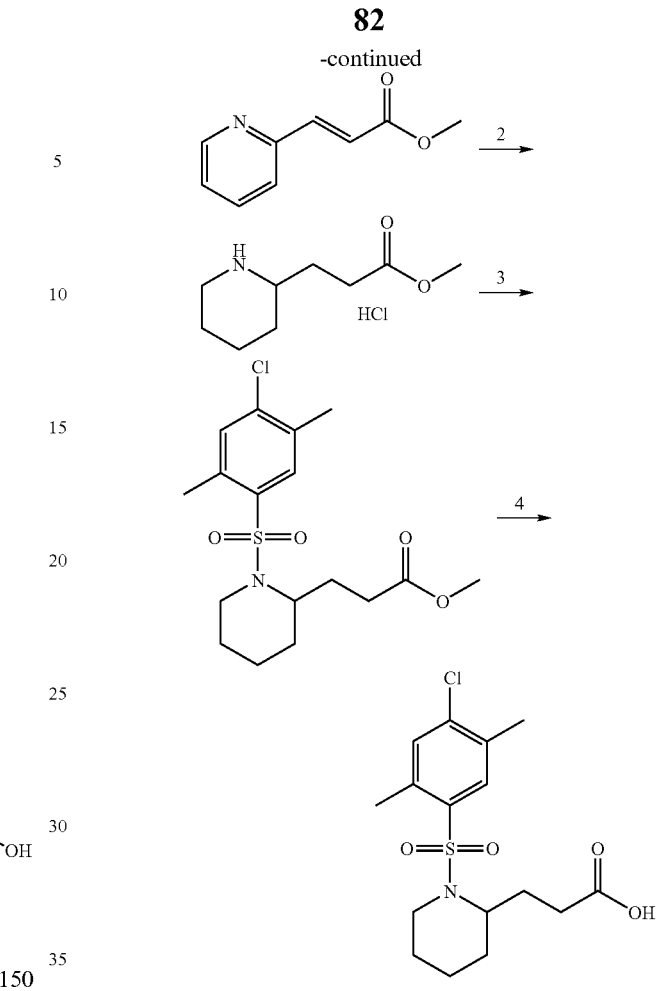

1. H₂SO₄ (12.8 ml, 240 mmol) was added to a solution of 3-(2-pyridyl)acrylic acid (23.88 g, 160 mmol) in methanol (750 ml). The reaction mixture was heated under reflux overnight and, after cooling, was poured at room temperature into saturated aqueous NaHCO₃ solution (1000 ml). The methanol was removed in a rotary evaporator and the aqueous phase was extracted twice with ethyl acetate (400 ml). The organic phase was washed with saturated NaCl solution (500 ml), dried over Na₂SO₄ and concentrated. The crude product was used in the next stage without further purification. Yield: 22.19 g, 85%

2. Methyl 3-(pyridin-2-yl)acrylate (22.15 g, 136 mmol) was dissolved in THF (300 ml) and chloroform (10.9 ml), and PtO₂ (3.08 g, 13.6 mmol, 0.1 eq.) was added under a nitrogen atmosphere. The solution was first rinsed for 10 min with nitrogen and then stirred overnight under an H₂ atmosphere (8 bar). After cooling, rinsing with nitrogen was first carried out again, the catalyst was removed by filtration over filtering earth, rinsing with CH₂Cl₂ was then carried out, and the filtrate was concentrated to dryness in vacuo. The methyl 3-(piperidin-2-yl)propionate hydrochloride was used in the next stage without further purification. Yield: 27.95 g, 99%

3. A solution of triethylamine (14.7 ml, 104.5 mmol) dissolved in CH₂Cl₂ (150 ml) was added to a solution of methyl 3-(piperidin-2-yl)propionate hydrochloride (8.69 g, 41.8 mmol) and 4-chloro-2,5-dimethylbenzenesulfonyl chloride (10.0 g, 41.8 mmol) in CH₂Cl₂ (150 ml). The reaction mixture was stirred overnight at room temperature and then washed with 1 M HCl (300 ml). The organic phase was dried over Na₂SO₄ and concentrated. The crude product was purified by column chromatography on silica gel (heptane/ethyl acetate 6:1 to 3:1). Yield: 12.82 g, 82%

4. Aqueous 6 M NaOH solution (100 ml) was added to a solution of methyl 3-(1-(4-chloro-2,5-dimethylphenylsulfonyl)piperidin-2-yl)propionate (12.82 g, 34.3 mmol) in THF (100 ml). After a reaction time of 1 h, the solvent was removed in a rotary evaporator and the residue was cooled to 0° C. 6 M HCl (100 ml) was added and extraction with ethyl acetate was carried out. The organic phase was dried over $Na_2SO_4$ and concentrated. Yield: 12.36 g, 100%

General Preparation of the Acid Units by Ester Cleavages

Variant A

The educt (20 mmol) was dissolved in 4 N hydrochloric acid in dioxane (80 mmol) and stirred overnight at RT. The solvent was largely distilled off, and the crude product was purified by recrystallization or chromatography.

Variant B

The educt (30 mmol) was dissolved in $CH_2Cl_2$ (200 ml), TFA (30 ml) was added and the mixture stirred for 2 h at RT. The solvent was largely distilled off and the crude product was purified by recrystalliztion or chromatography.

Variant C

The educt (30 mmol) was dissolved in THF (100 ml) and MeOH (100 ml); 6N NaOH (150 ml) was added, and the reaction mixture was stirred for 1 h at RT. The solvent was largely distilled off, and 6 N HCl (155 ml) was added at 0° C. Extraction with $CH_2Cl_2$, drying over $Na_2SO_4$, filtration of the drying agent and removal of the solvent by distillation yielded the crude product, which was purified by column chromatography.

Variant D

4 M NaOH (240 ml) and MeOH (25 ml) were added to a solution of the tert-butyl ester (15.6 g, 37.8 mmol) in THF (250 ml). The reaction mixture was stirred for 4 h at RT. 6 M NaOH (20 ml) was then added, and stirring was carried out overnight. The solution was cooled to 0° C., 6 M HCl (225 ml) was added thereto, and the organic phase was separated off and extracted several times with ethylacetate. After drying over $Na_2SO_4$ and filtration, the solvent was removed in vacuo.

Variant E

6 M NaOH (240 ml) was added to a solution of the tert-butyl ester (17.7 g, 48.7 mmol) in THF (200 ml). The reaction mixture was stirred overnight at RT. MeOH (20 ml) was then added thereto, and stirring was again carried out overnight. The solution was cooled to 0° C., 6 M HCl (230 ml) was added thereto, and the organic phase was separated off and extracted with ethyl acetate (200 ml) and $CH_2Cl_2$ (100 ml). After drying over $Na_2SO_4$ and filtration, the solvent was removed in vacuo.

Variant F

The tert-butyl ester (10.3 g, 23.8 mmol), 6 M NaOH (80 ml, 480 mmol), MeOH (80 ml) and THF (80 ml) were stirred for 15 min-1 h. The MeOH was then removed in vacuo, and 6 M HCl (120 ml) was added, extraction with $CH_2Cl_2$ (400 ml) was carried out, and the organic phases separated off was dried over $Na_2SO_4$. After filtration, the solvent was removed in vacuo.

Variant G

Dioxane (30 ml) was added to a suspension of the tert-butyl ester (38 mmol) in 6 M NaOH (64 ml, 384 mmol) and methanol (64 ml) until a solution was obtained. The reaction solution was stirred at RT. After 15 min-4 h, the organic solvent was removed, the residue was cooled to 0° C., and 6 M HCl (200 ml) was added. The aqueous phase was extracted with $CH_2Cl_2$ (200 ml). The combined organic phases were dried over $Na_2SO_4$. After filtration, the solvent was removed in vacuo and the residue was co-evaporated twice with i-propyl ether.

The amine units used are commercially available. Synthesis methods that are in principle possible for the amine units are described hereinbelow by means of amine units chosen by way of example.

Preparation of amine unit A3

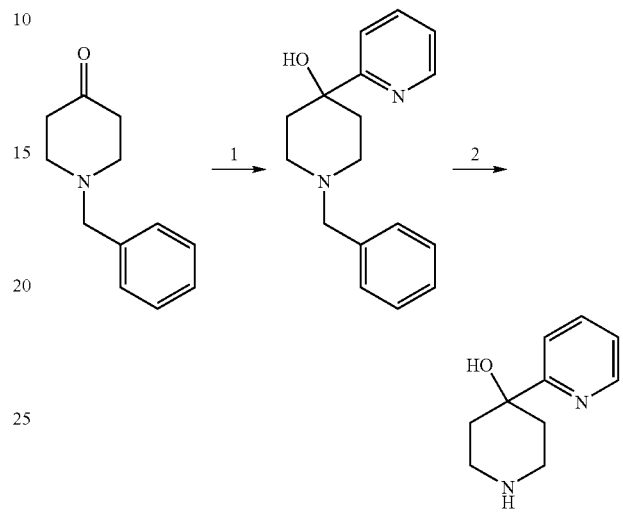

1. 2-Bromopyridine (12 g) in THF (900 ml) was cooled to −78° C., n-butyllithium (2.5 M, 61 ml) was added dropwise over a period of 2 h, and the mixture was stirred for 1 h at −78° C. N-Benzyl-4-piperidone (14.4 g) was added and the reaction mixture was stirred for 1 h at −78° C. Aqueous saturated $NH_4Cl$ solution (500 ml) was added at −10° C. to the reaction mixture. The organic phase was separated off and the aqueous phase was extracted with ethyl acetate (3×200 ml). The combined organic phases were dried over $Na_2SO_4$ and, after filtration, the solvent was removed. The residue was purified by flash chromatography (silica, gradient 30-100%, ethyl acetate/n-hexane). Yield: 9 g (44%)

2. Stage 2 (15 g) in methanol (100 ml) was added to palladium hydroxide (20%, 4 g) in methanol (50 ml). The reaction mixture was hydrogenated for 48 h at 80 psi. After filtration over Celite, the residue was washed with methanol (2×50 ml). The solvent was removed in vacuo and the solid was recrystallized from $CH_2Cl_2$. Yield: 7.8 g (75%)

Preparation of amine unit A7

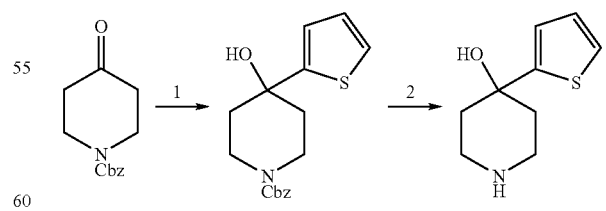

1. Thiophene (10 g) in THF (500 ml) was cooled to −78° C., and n-BuLi (66 ml) was added dropwise at −78° C. over a period of 1.5 h. After stirring for 1 h, n-Cbz-4-piperidone (25 g) in THF (50 ml) was added dropwise over a period of 20 min at −78° C., and stirring was carried out for 1 h. After warming to RT, aqueous saturated $NH_4Cl$ solution (250 ml) was added.

The organic phase was separated off and the aqueous phase was extracted with ethyl acetate (3×250 ml). The combined organic phases were dried over Na₂SO₄ and, after filtration, the solvent was removed in vacuo. The residue was crystallized (10% ethyl acetate/n-hexane) and then filtered and washed with 10% ethyl acetate/n-hexane. Yield: 22 g (66%)

2. KOH (2.7 g) in water (10 ml) was added to stage 2 (10 g) dissolved in ethanol (100 ml), and the mixture was heated under reflux for 24 h. Ethanol was removed in vacuo, water (30 ml) was added to the residue, and extraction with 20% IPA/CHCl₃ (4×40 ml) was carried out. The combined organic phases were dried over Na₂SO₄ and, after filtration, the solvent was removed in vacuo. The residue was recrystallized (50% ethyl acetate/n-hexane, 50 ml). Yield: 3 g (55%)

Preparation of amine unit A4

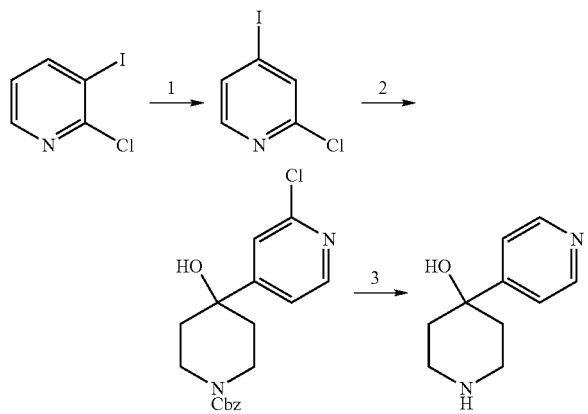

1. A solution of diisopropylamine (12.7 g) in THF (160 ml) was cooled to −15° C., and n-BuLi (83 ml) was added dropwise over a period of 20 min at −10° C. After stirring for 20 min at −5° C., the reaction mixture was cooled to −78° C., and 2-chloro-3-iodo-pyridine (20 g) dissolved in THF (40 ml) was added dropwise over a period of 20 min. The reaction mixture was stirred for 1 h at −78° C. After addition of water (40 ml), stirring was carried out for 15 min. The organic phase was separated off and dried over Na₂SO₄. After filtration, the solvent was removed in vacuo and the residue was purified by flash chromatography (silica, 5% ethyl acetate/n-hexane). Yield: 15 g (75%)

2. n-BuLi (2.5 M, 20 ml) was added dropwise over a period of 30 min to a solution of stage 2 (10 g) in THF (500 ml), and the mixture was stirred for 20 min. N-Cbz-4-piperidone (8.8 g) in THF (20 ml) was added drowpise at −78° C. over a period of 15 min, and the reaction mixture was stirred for 1 h. After warming to 0° C., aqueous saturated NH₄Cl solution (250 ml) was added, and the organic phase was separated off and extracted with ethyl acetate (2×200 ml). The combined organic phases were dried over Na₂SO₄. After filtration, the solvent was removed in vacuo and the residue was purified by flash chromatography (silica, gradient 10-40%, ethyl acetate/n-hexane). Yield: 7.5 g (52%)

3. Stage 3 (7.5 g) in ethanol (80 ml) was added to palladium hydroxide (20%, 1.5 g) in ethanol (70 ml). The reaction mixture was hydrogenated for 2 h at 80 psi. After filtration over Celite, the residue was washed with ethanol (2×50 ml). The solvent was removed in vacuo. Yield: 3.2 g (83%)

Preparation of amine unit A2

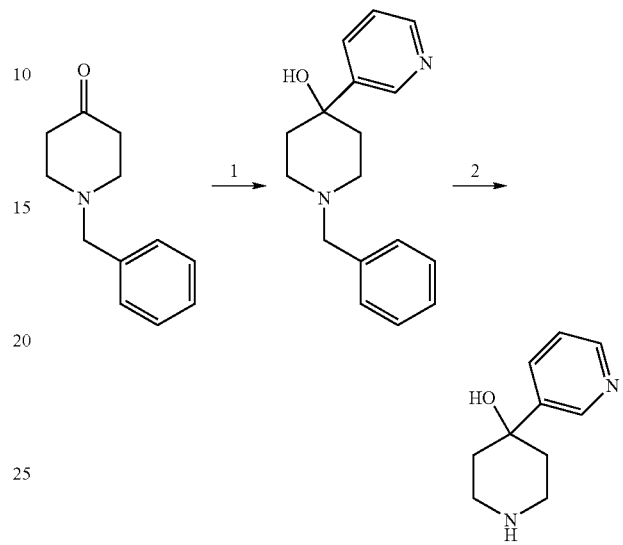

1. 1,1-Dibromoethane (0.5 g) and isopropyl chloride (17.3 ml) were added dropwise at RT over a period of 15 min to a suspension of magnesium (5.7 g) in ether (125 ml). 3-Bromopyridine (25 g) in THF (400 ml) was added dropwise at 40° C. over a period of 20 min, and the reaction mixture was stirred for 2 h at 40° C. A solution of 1-benzylpiperidin-4-one (30 g) in THF (100 ml) was added dropwise at 40° C. over a period of 20 min, and the reaction mixture was stirred overnight. Water (50 ml) was added at 0° C. to the reaction mixture, and filtration over Celite was carried out. After extraction with CH₂Cl₂ (2×100 ml) and water (50 ml), the combined organic phases were dried over Na₂SO₄. After filtration, the solvent was removed in vacuo and the residue was purified by column chromatography (neutral alumina, 5% MeOH/CHCl₃). Yield: 8 g (19%)

2. A catalytic amount of 10% Pd/C, ammonium formate solution (22.7 g in 50 ml of water) was added to a solution of stage 2 (32 g) in methanol (200 ml), and the mixture was heated overnight at 68° C. The reaction mixture was filtered off over Celite, the solvent was removed in vacuo, and the residue was washed with acetone (100 ml). Yield: 17 g (81%)

| Number | Structure | Name |
|---|---|---|
| A1 | ![structure] | 4-Benzylpiperidin-4-ol |
| A2 | ![structure] | 4-(Pyridin-3-yl)piperidin-4-ol |

-continued

| Number | Structure | Name |
|---|---|---|
| A3 | 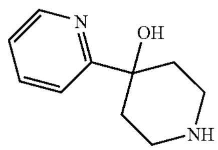 [SMILES: OC1(c2ccccn2)CCNCC1] | 4-(Pyridin-2-yl)piperidin-4-ol |
| A4 | 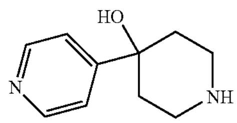 | 4-Pyridin-4-yl)piperidin-4-ol |
| A5 | 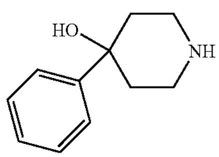 [SMILES: OC1(c2ccccc2)CCNCC1] | 4-Phenylpiperidin-4-ol |
| A6 | 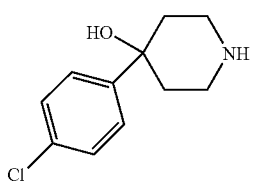 [SMILES: OC1(c2ccc(Cl)cc2)CCNCC1] | 4-(4-Chlorophenyl)piperidin-4-ol |
| A7 | 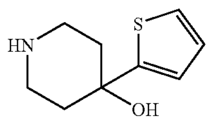 [SMILES: OC1(c2cccs2)CCNCC1] | 4-(Thiophen-2-yl)piperidin-4-ol |
| A8 | 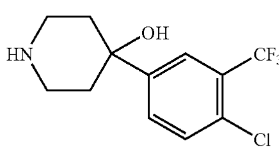 | 4-(4-Chloro-3-(trifluoromethyl)phenyl)-piperidin-4-ol |
| A9 | 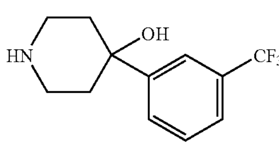 | 4-(3-(Trifluoromethyl)phenyl)piperidin-4-ol |
| A10 | 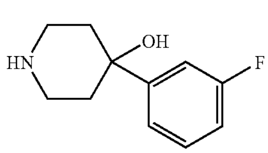 [SMILES: OC1(c2cccc(F)c2)CCNCC1] | 4-(3-Fluorophenyl)piperidin-4-ol |
| A11 | 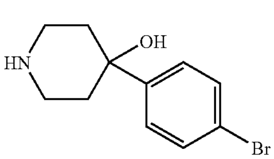 [SMILES: OC1(c2ccc(Br)cc2)CCNCC1] | 4-(4-Bromophenyl)piperidin-4-ol |

General Instructions for the Preparation of the Example Compounds Via Parallel Synthesis

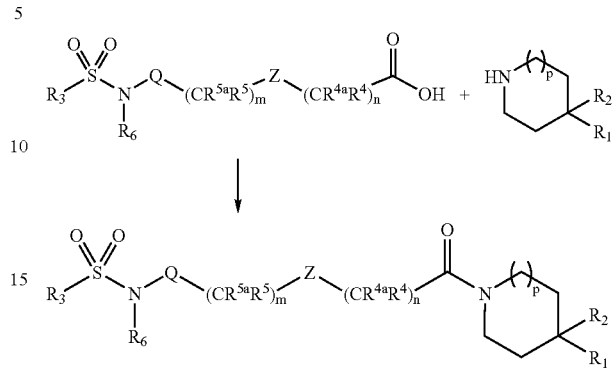

Parallel Synthesis Method 1

Acid solution (0.05 M in $CH_2Cl_2$, 2 ml) was added to 105 µmol of CDI solution (0.105 M in $CH_2Cl_2$, 1 ml) and the mixture was shaken for 1 h at RT. 100 µmol of the amine solution (0.1 M in $CH_2Cl_2$) were subsequently added at RT and the mixture was shaken for a further 12 h at RT. 3 ml of water were subsequently added to the reaction mixture, the mixture was shaken for 15 min and the organic phase was separated off. After removal of the solvent in vacuo, the crude products were analysed by means of LC-MS and purified via HPLC.

Parallel Synthesis Method 2

100 µmol of acid solution (0.05 M in $CH_2Cl_2$, 2 ml) were initially introduced into the reaction vessel at RT and 105 µmol of CDI solution (0.105 M in $CH_2Cl_2$, 1 ml) were added. After a stirring time of 1 h at RT, 100 µmol of the corresponding amine (0.1 M in $CH_2Cl_2$) were pipetted into the reaction solution. The reaction solution was stirred for 16 h at RT. 3 ml of water were then added and the mixture was vortexed and mixed thoroughly for 30 min. The stirring bead was filtered off and the vessel was rinsed out with 1.5 ml of $CH_2Cl_2$.

The aqueous phase was removed and discarded. 3 ml of dist. $H_2O$ and 0.5 ml of $CH_2Cl_2$ were added to the organic phase and the mixture was vortexed, and thoroughly mixed intensively for 30 min. After centrifugation, the aqueous phase was separated off and discarded. The organic phase was extracted analogously a second time with 3 ml of saturated NaCl solution. The organic phase was then removed, introduced into a test-tube and dried over an $MgSO_4$ cartridge. After removal of the solvent in vacuo, the crude products were analysed by means of LC-MS and purified via HPLC.

Parallel Synthesis Method 3

The acid (50 mg, 1 eq.) was reacted with the amine (50-70 mg, 1.2 eq.) in $CH_2Cl_2$ (3 ml/mmol) using the coupling reagents EDCI (1.5 eq.), HOBt (1 eq.) and DIPEA (2 eq.). After removal of the solvent, the products were purified by column chromatography.

| Example | Synthesis method | Mass |
|---|---|---|
| 1 | 1 | 532.26 |
| 2 | 1 | 535.05 |
| 4 | 1 | 491.21 |
| 6 | 1 | 535.05 |
| 7 | 1 | 530.25 |

| Example | Synthesis method | Mass |
|---|---|---|
| 8 | 1 | 544.26 |
| 9 | 1 | 548.07 |
| 10 | 1 | 501.09 |
| 11 | 1 | 544.26 |
| 12 | 1 | 541.12 |
| 13 | 1 | 594.28 |
| 14 | 1 | 572.29 |
| 15 | 1 | 476.18 |
| 16 | 1 | 506.21 |
| 17 | 1 | 513.09 |
| 18 | 1 | 573.29 |
| 19 | 1 | 527.10 |
| 20 | 1 | 517.15 |
| 21 | 1 | 503.21 |
| 22 | 1 | 458.19 |
| 23 | 1 | 564.23 |
| 24 | 1 | 472.20 |
| 25 | 1 | 541.12 |
| 26 | 1 | 489.19 |
| 27 | 1 | 472.20 |
| 28 | 1 | 476.20 |
| 29 | 1 | 530.25 |
| 30 | 1 | 487.21 |
| 31 | 1 | 492.15 |
| 32 | 1 | 501.23 |
| 33 | 1 | 562.11 |
| 34 | 1 | 445.17 |
| 35 | 1 | 516.23 |
| 36 | 1 | 527.10 |
| 37 | 1 | 472.20 |
| 38 | 1 | 514.17 |
| 39 | 1 | 446.19 |
| 40 | 1 | 489.19 |
| 41 | 1 | 493.19 |
| 42 | 1 | 463.18 |
| 43 | 1 | 568.16 |
| 44 | 1 | 517.22 |
| 45 | 1 | 559.27 |
| 46 | 1 | 459.18 |
| 47 | 1 | 560.27 |
| 48 | 1 | 560.27 |
| 49 | 1 | 488.21 |
| 50 | 1 | 551.21 |
| 51 | 1 | 459.18 |
| 52 | 1 | 505.19 |
| 53 | 1 | 520.18 |
| 54 | 1 | 459.18 |
| 55 | 1 | 531.24 |
| 56 | 1 | 451.16 |
| 57 | 1 | 502.21 |
| 58 | 1 | 463.16 |
| 59 | 1 | 513.15 |
| 60 | 1 | 546.24 |
| 61 | 2 | 498.14 |
| 62 | 2 | 478.19 |
| 63 | 2 | 556.18 |
| 64 | 2 | 536.23 |
| 65 | 2 | 554.21 |
| 66 | 2 | 548.21 |
| 67 | 2 | 528.27 |
| 68 | 2 | 515.25 |
| 69 | 2 | 658.11 |
| 70 | 2 | 469.15 |
| 71 | 2 | 469.15 |
| 72 | 2 | 539.19 |
| 73 | 2 | 521.20 |
| 74 | 2 | 565.22 |
| 75 | 2 | 552.21 |
| 76 | 2 | 520.20 |
| 77 | 2 | 534.22 |
| 78 | 2 | 588.13 |
| 79 | 2 | 622.09 |
| 80 | 2 | 588.13 |
| 81 | 2 | 602.14 |
| 82 | 2 | 578.25 |
| 83 | 2 | 664.13 |
| 84 | 2 | 644.19 |
| 90 | 2 | 521.20 |
| 91 | 2 | 589.12 |
| 92 | 2 | 589.12 |
| 93 | 2 | 502.11 |
| 94 | 2 | 515.25 |
| 95 | 2 | 631.17 |
| 96 | 2 | 541.19 |
| 97 | 2 | 465.17 |
| 98 | 2 | 547.05 |
| 99 | 2 | 588.13 |
| 100 | 2 | 575.10 |
| 101 | 2 | 562.25 |
| 102 | 2 | 473.08 |
| 103 | 2 | 473.08 |
| 104 | 2 | 548.07 |
| 105 | 2 | 514.11 |
| 106 | 2 | 528.13 |
| 107 | 2 | 580.02 |
| 108 | 2 | 546.05 |
| 109 | 2 | 560.07 |
| 119 | 3 | 519.2 |
| 120 | 3 | 536.2 |
| 122 | 3 | 519.2 |
| 123 | 2 | 601.1 |
| 124 | 2 | 648.1 |
| 125 | 2 | 546.1 |
| 138 | 3 | 531.2 |
| 141 | 3 | 508.2 |
| 142 | 3 | 548.2 |
| 143 | 3 | 491.2 |
| 144 | 3 | 531.2 |
| 145 | 3 | 606.1 |
| 146 | 3 | 589.1 |
| 147 | 3 | 589.1 |
| 149 | 2 | 494.2 |
| 150 | 2 | 527.1 |
| 151 | 2 | 571.1 |
| 152 | 2 | 493.2 |
| 153 | 2 | 507.2 |
| 154 | 2 | 561.1 |
| 155 | 2 | 540.2 |
| 156 | 2 | 573.1 |
| 157 | 2 | 534.2 |
| 158 | 2 | 533.2 |
| 159 | 2 | 547.2 |
| 160 | 2 | 635.1 |
| 161 | 2 | 520.2 |
| 162 | 2 | 607.1 |
| 163 | 2 | 621.1 |
| 164 | 2 | 675.1 |
| 165 | 2 | 709.1 |
| 166 | 2 | 627.1 |
| 167 | 2 | 671 |
| 168 | 2 | 593.1 |
| 169 | 2 | 607.1 |
| 170 | 2 | 661.1 |
| 171 | 2 | 695 |
| 172 | 2 | 540.1 |
| 173 | 2 | 573.1 |
| 174 | 2 | 617.1 |
| 175 | 2 | 539.2 |
| 176 | 2 | 553.2 |
| 177 | 2 | 607.2 |
| 178 | 2 | 641.1 |
| 179 | 2 | 558.3 |
| 180 | 2 | 646.2 |
| 181 | 2 | 578.2 |
| 182 | 2 | 622.2 |
| 183 | 2 | 544.3 |
| 184 | 2 | 564.2 |
| 185 | 2 | 608.2 |
| 186 | 2 | 550.2 |
| 187 | 2 | 594.1 |
| 188 | 2 | 516.2 |
| 189 | 2 | 530.2 |
| 190 | 2 | 584.2 |
| 191 | 1 | 593.3 |

| Example | Synthesis method | Mass |
|---|---|---|
| 192 | 1 | 543.3 |
| 193 | 2 | 517.2 |
| 194 | 2 | 517.2 |
| 195 | 2 | 593.3 |
| 196 | 2 | 541.1 |
| 197 | 2 | 527.1 |
| 198 | 2 | 515.1 |
| 199 | 2 | 515.1 |
| 200 | 2 | 596.2 |
| 201 | 2 | 576.3 |
| 202 | 2 | 550.2 |
| 203 | 2 | 533.1 |
| 204 | 2 | 561.1 |
| 205 | 2 | 622.2 |
| 206 | 2 | 544.3 |
| 207 | 2 | 558.3 |
| 208 | 2 | 612.3 |
| 209 | 2 | 580.2 |
| 210 | 2 | 624.2 |
| 211 | 2 | 560.3 |
| 212 | 2 | 614.3 |
| 213 | 2 | 517.2 |
| 214 | 2 | 593.1 |
| 215 | 2 | 515.2 |
| 216 | 2 | 529.2 |
| 217 | 2 | 583.2 |
| 218 | 2 | 627.1 |
| 219 | 2 | 603 |
| 220 | 2 | 526.5 |
| 221 | 2 | 539.1 |
| 222 | 2 | 593.1 |
| 223 | 2 | 633 |
| 224 | 2 | 609 |
| 225 | 2 | 531.1 |
| 226 | 2 | 545.1 |
| 227 | 2 | 599.1 |
| 228 | 2 | 617.2 |
| 229 | 2 | 547.1 |
| 230 | 2 | 594.1 |
| 231 | 2 | 584.2 |
| 232 | 2 | 606.3 |
| 233 | 2 | 660.3 |
| 234 | 2 | 618 |
| 235 | 2 | 608.1 |
| 236 | 2 | 642.1 |
| 237 | 2 | 646.2 |
| 238 | 2 | 648.2 |
| 239 | 2 | 521.2 |
| 240 | 2 | 544.3 |
| 241 | 2 | 546.3 |
| 242 | 2 | 564.2 |
| 243 | 2 | 608.2 |
| 244 | 2 | 530.2 |
| 245 | 2 | 544.3 |
| 246 | 2 | 632.2 |
| 247 | 2 | 648 |
| 248 | 2 | 573.1 |
| 249 | 2 | 573.1 |
| 250 | 2 | 661 |
| 251 | 2 | 563.2 |
| 252 | 2 | 543.3 |
| 253 | 2 | 631.2 |
| 254 | 2 | 608.1 |
| 255 | 2 | 574.1 |
| 256 | 2 | 500.1 |
| 257 | 2 | 544.1 |
| 258 | 2 | 534.2 |
| 259 | 2 | 568.1 |
| 260 | 2 | 540 |
| 261 | 2 | 584 |
| 262 | 2 | 574 |
| 263 | 2 | 608 |
| 264 | 2 | 580.1 |
| 265 | 2 | 516.2 |
| 266 | 2 | 538 |
| 267 | 2 | 522.2 |
| 268 | 2 | 550.2 |
| 269 | 2 | 552.2 |
| 270 | 2 | 546.1 |
| 271 | 2 | 546.1 |
| 272 | 2 | 594 |
| 273 | 2 | 528.2 |
| 274 | 2 | 541.2 |
| 275 | 2 | 537.2 |
| 276 | 2 | 503.2 |
| 277 | 2 | 517.2 |
| 278 | 2 | 605.2 |

In all cases the reaction was demonstrated by HPLC-MS (ESI). The particular molecular peak found is given in the table. The compounds had a purity of >80%, the main product in all cases being the compound according to the invention.

Synthesis of Individual Substances

Analysis was by mass spectroscopy and/or NMR. Unless indicated otherwise, the compounds are isomer mixtures in the ratio of approx. 1:1. In the case of analogous syntheses, there may be slight variations in respect of the solvents, the equivalents of the reagents/educts, the reaction times etc.

Example 85

1-(4-Hydroxy-4-(thiophen-2-yl)piperidin-1-yl)-2-((1-(4-methoxy-2,6-dimethylphenylsulfonyl)piperidin-2-yl)methoxy)ethanone

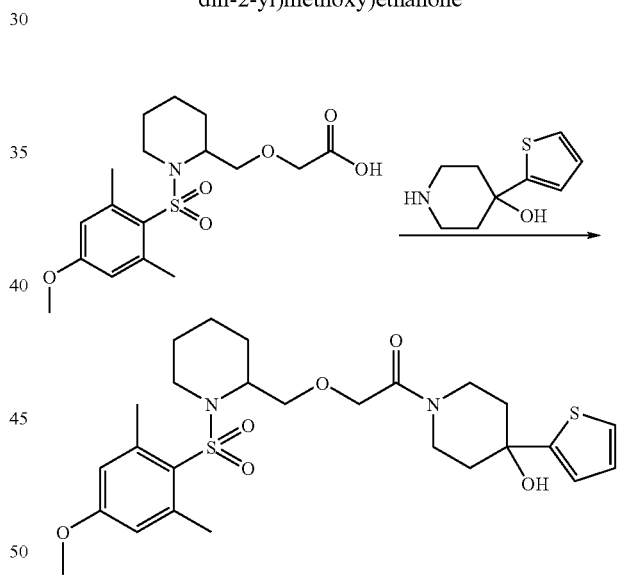

N,N'-Carbonyldiimidazole (68 mg, 0.424 mmol) was added to a solution of 2-((1-(4-methoxy-2,6-dimethylphenylsulfonyl)piperidin-2-yl)methoxy)acetic acid (acid unit S24) (150 mg, 0.404 mmol) in methylene chloride (5 ml) and the mixture was stirred for 1 h at room temperature. A solution of 4-(thiophen-2-yl)piperidin-4-ol (73 mg, 0.404 mmol) in methylene chloride (2 ml) was subsequently added and the reaction mixture was stirred for 15 h at room temperature. Thereafter, saturated sodium bicarbonate solution (10 ml) was added to the reaction mixture and the aqueous phase was subsequently extracted with methylene chloride (2×10 ml). The combined organic phases were extracted with saturated sodium chloride solution (10 ml), dried with sodium sulfate and concentrated in vacuo. The crude product was purified by flash chromatography with ethyl acetate/hexane (20:1).

Yield: 140 mg (65%), yellowish oil $^1$H-NMR (400 MHz, DMSO-d$_6$): 1.55 (5H); 1.79 (6H); 2.53 (6H); 2.96 (2H): 3.25 (1H); 3.52 (2H); 3.69 (1H); 3.79 (3H); 4.04 (3H); 4.15 (1H); 5.59 (1H); 6.79 (2H); 6.95 (2H); 7.36 (1H).

Example 87

1-(4-Hydroxy-4-(pyridin-3-yl)piperidin-1-yl)-2-((1-(4-methoxy-2,6-dimethylphenylsulfonyl)piperidin-2-yl)methoxy)ethanone hydrochloride

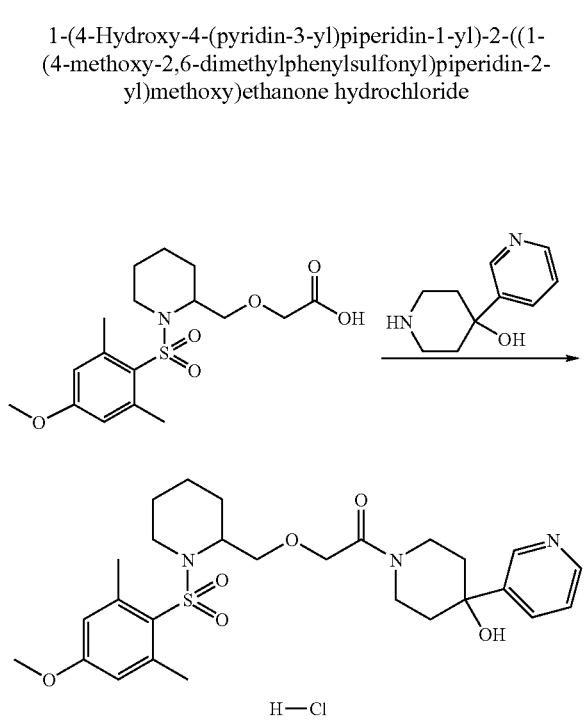

N,N'-Carbonyldiimidazole (68 mg, 0.424 mmol) was added to a solution of 2-((1-(4-methoxy-2,6-dimethylphenyl-sulfonyl)piperidin-2-yl)methoxy)acetic acid (150 mg, 0.404 mmol) in methylene chloride (5 ml) and the mixture was stirred for 1 h at room temperature. A solution of 4-(pyridin-3-yl)piperidin-4-ol (A2) (72 mg, 0.404 mmol) in methylene chloride (2 ml) was subsequently added and the reaction mixture was stirred for 15 h at room temperature. Thereafter, saturated sodium bicarbonate solution (10 ml) was added to the reaction mixture and the aqueous phase was subsequently extracted with methylene chloride (2×10 ml). The combined organic phases were extracted with saturated sodium chloride solution (10 ml), dried with sodium sulfate and concentrated in vacuo. The crude product was purified by flash chromatography with ethyl acetate/methanol (20:1). 1-(4-Hydroxy-4-(pyridin-3-yl)piperidin-1-yl)-2-((1-(4-methoxy-2,6-dimethylphenylsulfonyl)piperidin-2-yl)methoxy)ethanone (100 mg, 0.188 mmol) was dissolved in methyl ethyl ketone (3 ml), and chlorotrimethylsilane (28 µl, 0.226 mmol) was slowly added. Diethyl ether (10 ml) was subsequently added and the mixture was stirred for 1 h at 0° C. The precipitate formed was filtered off, dried with exclusion of air and washed with diethyl ether.

Yield: 90 mg (39%), white solid

HPLC-MS, m/z 532.1 (MH$^+$)

Example 89

1-(4-Hydroxy-4-(pyridin-3-yl)piperidin-1-yl)-2-((1-(4-methoxy-2,6-dimethylphenylsulfonyl)pyrrolidin-2-yl)methoxy)ethanone hydrochloride

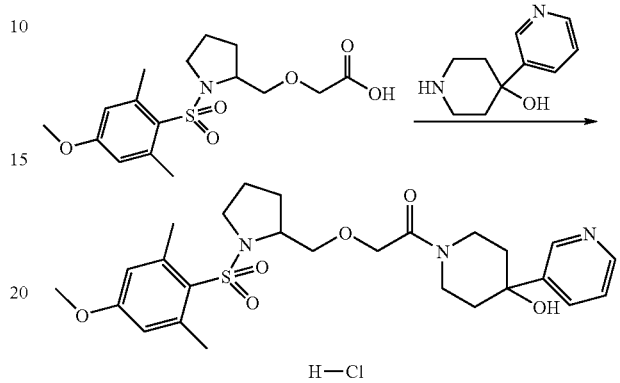

N,N'-Carbonyldiimidazole (71 mg, 0.441 mmol) was added to a solution of 2-((1-(4-methoxy-2,6-dimethylphenyl-sulfonyl)pyrrolidin-2-yl)methoxy)acetic acid (acid unit S27) (150 mg, 0.420 mmol) in methylene chloride (7 ml) and the mixture was stirred for 1 h at room temperature. A solution of 4-(pyridin-3-yl)piperidin-4-ol (A2) (74 mg, 0.420 mmol) in methylene chloride (3 ml) was subsequently added and the reaction mixture was stirred for 15 h at room temperature. Thereafter, saturated sodium bicarbonate solution (10 ml) was added to the reaction mixture and the aqueous phase was subsequently extracted with methylene chloride (2×10 ml). The combined organic phases were extracted with saturated sodium chloride solution (10 ml), dried with sodium sulfate and concentrated in vacuo. The crude product was purified by flash chromatography with ethyl acetate/methanol/hexane (10:1:1). 1-(4-Hydroxy-4-(pyridin-3-yl)piperidin-1-yl)-2-((1-(4-methoxy-2,6-dimethylphenylsulfonyl)pyrrolidin-2-yl)methoxy)ethanone (160 mg, 0.309 mmol) was dissolved in methyl ethyl ketone/diethyl ether (1:1; 5 ml), and chlorotrimethylsilane (59 µl, 0.464 mmol) was slowly added. Diethyl ether (10 ml) was subsequently added and the mixture was stirred for 1 h at 0° C. The precipitate formed was filtered off, dried with exclusion of air and washed with diethyl ether.

Yield: 120 mg (52%), white solid

HPLC-MS, m/z 518.1 (MH$^+$)

Example 3

N-(2-(2-(4-Hydroxy-4-(pyridin-3-yl)piperidin-1-yl)-2-oxoethoxy)ethyl)-4-methoxy-N,2,6-trimethylphenylsulfonamide hydrochloride

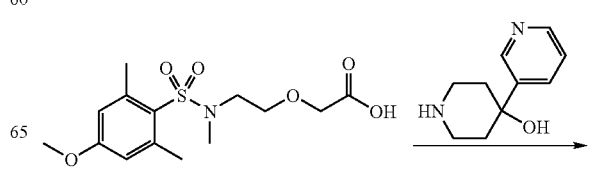

-continued

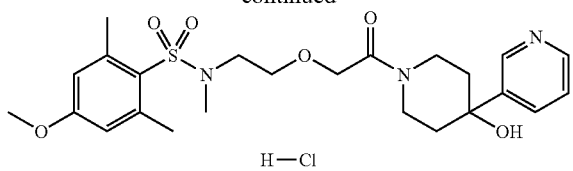

N,N'-Carbonyldiimidazole (77 mg, 0.475 mmol) was added to a solution of 2-(2-(4-methoxy-N,2,6-trimethylphenylsulfonamido)ethoxy)acetic acid (acid unit S2) (150 mg, 0.453 mmol) in methylene chloride (5 ml) and the mixture was stirred for 1 h at room temperature. A solution of 4-(pyridin-3-yl)piperidin-4-ol (A2) (80 mg, 0.453 mmol) in methylene chloride (2 ml) was subsequently added and the reaction mixture was stirred for 15 h at room temperature. Thereafter, saturated sodium bicarbonate solution (10 ml) was added to the reaction mixture and the aqueous phase was subsequently extracted with methylene chloride (20 ml). The combined organic phases were extracted with saturated sodium chloride solution (10 ml), dried with sodium sulfate and concentrated in vacuo. The crude product was purified by flash chromatography with diethyl ether/methylene chloride/methanol/ammonia solution (25% aq.) (50:50:5:1). N-(2-(2-(4-Hydroxy-4-(pyridin-3-yl)piperidin-1-yl)-2-oxoethoxy)ethyl)-4-methoxy-N,2,6-trimethylphenylsulfonamide (170 mg. 0.346 mmol) was dissolved in diethyl ether/methyl ethyl ketone (15:1, 32 ml), and chlorotrimethylsilane (81 μl, 0.692 mmol) was slowly added. The mixture was subsequently stirred for 30 min at 0° C. The precipitate formed was filtered off, washed with diethyl ether/hexane and dried.

Yield: 120 mg (50%), white solid
HPLC-MS, m/z 492.1 (MH+)

Example 5

2,4,6-Trichloro-N-(2-(2-(4-hydroxy-4-(pyridin-3-yl)piperidin-1-yl)-2-oxoethoxy)ethyl)-N-methylphenylsulfonamide hydrochloride

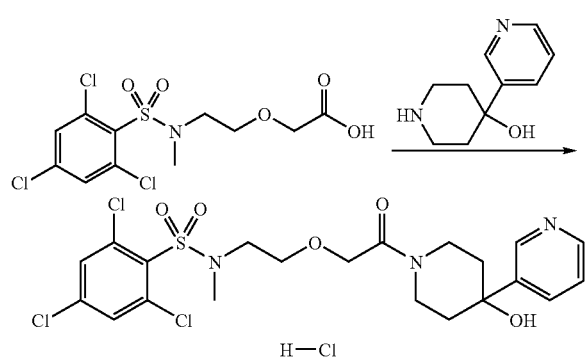

N,N'-Carbonyldiimidazole (68 mg, 0.420 mmol) was added to a solution of 2-(2-(2,4,6-trichloro-N-methylphenylsulfonamido)ethoxy)acetic acid (acid unit S9) (150 mg, 0.400 mmol) in methylene chloride (4.5 ml) and the mixture was stirred for 1 h at room temperature. A solution of 4-(pyridin-3-yl)piperidin-4-ol (A2) (71 mg, 0.400 mmol) in methylene chloride (2 ml) was subsequently added and the reaction mixture was stirred for 15 h at room temperature. Thereafter, saturated sodium bicarbonate solution (10 ml) was added to the reaction mixture and the aqueous phase was subsequently extracted with methylene chloride (20 ml). The combined organic phases were extracted with saturated sodium chloride solution (10 ml), dried with sodium sulfate and concentrated in vacuo. The crude product was purified by flash chromatography with diethyl ether/methylene chloride/methanol/ammonia solution (25% aq.) (50:50:5:1). 2,4,6-Trichloro-N-(2-(2-(4-hydroxy-4-(pyridin-3-yl)piperidin-1-yl)-2-oxoethoxy)ethyl)-N-methylphenylsulfonamide (200 mg. 0.374 mmol) was dissolved in diethyl ether/methyl ethyl ketone (25:2, 27 ml), and chlorotrimethylsilane (88 μl, 0.692 mmol) was slowly added. The mixture was subsequently stirred for 30 min at 0° C. The precipitate formed was filtered off, washed with diethyl ether/hexane and dried.

Yield: 130 mg (57%), white solid $^1$H-NMR (600 MHz, DMSO-$d_6$): 1.68 (2H); 1.89 (1H); 2.02 (1H); 2.95 (3H); 3.30-3.70 (7H); 4.18 (2H); 4.32 (1H); 5.80 (1H); 7.88 (2H); 7.96 (1H); 8.58 (1H); 8.78 (1H); 8.92 (1H).

Example 86

N-(2-(2-(4-Hydroxy-4-(thiophen-2-yl)piperidin-1-yl)-2-oxoethoxy)ethyl)-4-methoxy-N,2,6-trimethylphenylsulfonamide

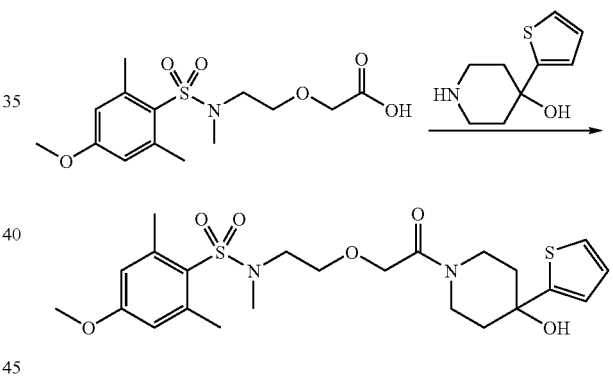

N,N'-Carbonyldiimidazole (77 mg, 0.475 mmol) was added to a solution of 2-(2-(4-methoxy-N,2,6-trimethylphenylsulfonamido)-ethoxy)acetic acid (acid unit S2) (150 mg, 0.453 mmol) in methylene chloride (7 ml) and the mixture was stirred for 1 h at room temperature. A solution of 4-(thiophen-2-yl)piperidin-4-ol (A7) (82 mg, 0.453 mmol) in methylene chloride (3 ml) was subsequently added and the reaction mixture was stirred for 15 h at room temperature. Thereafter, saturated sodium bicarbonate solution (10 ml) was added to the reaction mixture and the aqueous phase was subsequently extracted with methylene chloride (20 ml). The combined organic phases were extracted with saturated sodium chloride solution (10 ml), dried with sodium sulfate and concentrated in vacuo. The crude product was purified by flash chromatography with ethyl acetate/methanol/ammonia solution (25% aq.) (100:10:1).

Yield: 170 mg (76%), yellow oil
HPLC-MS, m/z 496.9 (MH+)

Example 88

N-(2-(2-(4-Hydroxy-4-(pyridin-4-yl)piperidin-1-yl)-2-oxoethoxy)ethyl)-4-methoxy-N,2,6-trimethylphenylsulfonamide

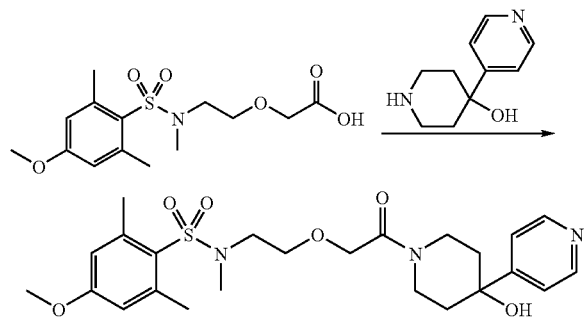

N,N'-Carbonyldiimidazole (77 mg, 0.475 mmol) was added to a solution of 2-(2-(4-methoxy-N,2,6-trimethylphenylsulfonamido)ethoxy)acetic acid (acid unit S2) (150 mg, 0.453 mmol) in methylene chloride (7 ml) and the mixture was stirred for 1 h at room temperature. A solution of 4-(pyridin-4-yl)piperidin-4-ol (A4) (80 mg, 0.453 mmol) in methylene chloride (3 ml) was subsequently added and the reaction mixture was stirred for 15 h at room temperature. Thereafter, saturated sodium bicarbonate solution (10 ml) was added to the reaction mixture and the aqueous phase was subsequently extracted with methylene chloride (20 ml). The combined organic phases were extracted with saturated sodium chloride solution (10 ml), dried with sodium sulfate and concentrated in vacuo. The crude product was purified by flash chromatography with ethyl acetate/methanol/hexane/ammonia solution (25% aq.) (100:10:10:1).

Yield: 50 mg (22%), yellow oil

Example 137

Preparation of N-(2-(2-(4-hydroxy-4-phenylpiperidin-1-yl)-2-oxoethoxy)ethyl)-4-methoxy-N,2,6-trimethylphenylsulfonamide

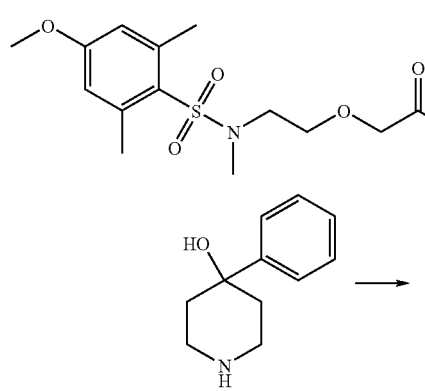

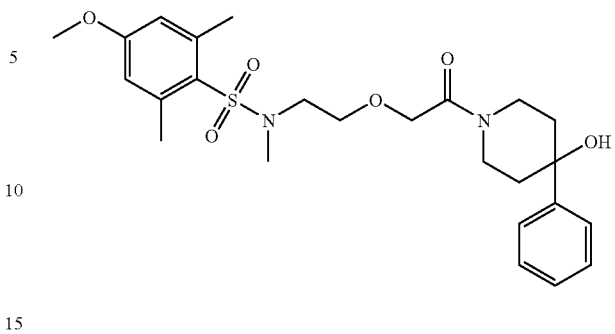

EDCI (2.76 g, 14.48 mmol) was added at 0° C. to a suspension of the acid (4.00 g, 12.1 mmol), amine (2.14 g, 12.1 mmol), DIPEA (4.0 ml, 24 mmol) and HOAt (165 mg, 1.21 mmol) in $CH_2Cl_2$ (250 ml) and the reaction mixture was stirred for 30 min at 0° C. and overnight at RT. The organic phase was extracted with 1 M HCl (3×100 ml) and saturated NaCl solution (100 ml) and dried over $Na_2SO_4$. After filtration and removal of the solvent, the product was purified by column chromatography (silica, $CH_2Cl_2$/7 M $NH_3$ in MeOH 98:2). Yield: 5.14 g (87%)

Reaction of 2-(2-(4-methoxy-N,2,6-trimethylphenylsulfonamide)ethoxy)acetic acid (acid unit S2) with amines

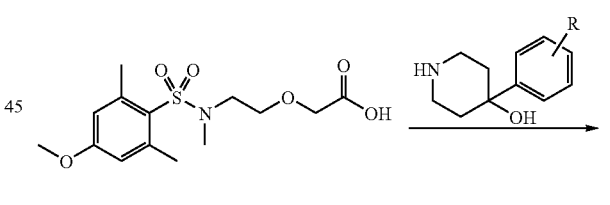

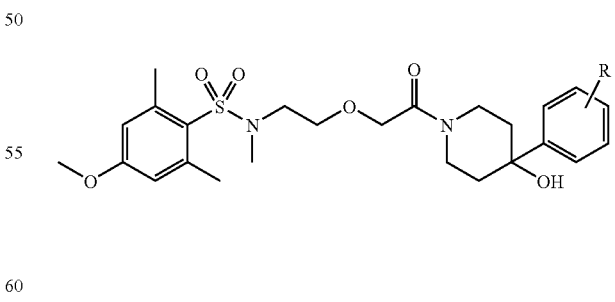

The compounds of the examples listed in the following table were prepared from acid unit S2 by reaction with the corresponding amines closely following the process described for Example 88. The amines used are commercially available.

| Example No. | Amine | Yield (%) | MS, m/z (MH+) |
|---|---|---|---|
| 132 | 4-(3-(Trifluoromethyl)phenyl)piperidin-4-ol | 71 | 559.2 |
| 136* | 4-(4-Chlorophenyl)piperidin-4-ol | 84 | 525.2 |
| 279*,# | 4-(Pyridin-3-ylmethyl)piperidin-4-ol dihydrochloride§ | 49 | 506.2 |
| 280* | 4-(Pyridin-4-ylmethyl)piperidin-4-ol dihydrochloride§ | 57 | 506.2 |

*A mixture of methylene chloride and N,N-dimethylformamide was used instead of methylene chloride
Preparation of the corresponding hydrochloride (HCl): The free base was dissolved in a small amount of methyl ethyl ketone; 2 M hydrogen chloride solution in diethyl ether was added, and the resulting hydrochloride (HCl) was filtered out.
§3 eq. of triethylamine were added to the reaction.

Reaction of 4-(pyridin-3-yl)piperidin-4-ol (amine A2) with carboxylic acids

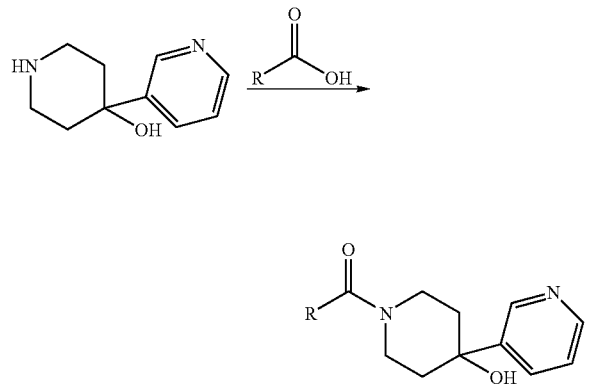

The compounds of the examples listed in the following table were prepared from the corresponding acid units by reaction with 4-(pyridin-3-yl)piperidin-4-ol closely following the process described for Example 88. The amine used is commercially available, the syntheses of the carboxylic acids were carried out as described. The solvent N,N-dimethylformamide or a methylene chloride/N,N-dimethylformamide mixture was used instead of the solvent methylene chloride in some reactions. The reaction time was mostly from 15 h to 3 d; the progress of the reaction was monitored by thin-layer chromatography. The compounds of Examples 128, 129 and 131 are exceptions; these were converted into the corresponding amides by reaction of the corresponding carboxylic acids with an alternative coupling reagent: 1-methylpiperazine (1 eq., 19.84 mmol) and 4-methylmorpholine (2 eq.) were added to a solution of the carboxylic acid (1.1 eq.) in N,N-dimethylformamide. Benzotriazol-1-yloxytris(dimethylamino)phosphonium hexafluorophosphate (1.3 eq.) was then added to the mixture, and stirring was carried out for 15 h at room temperature. Concentration in vacuo was then carried out, the residue was taken up in ethyl acetate and saturated sodium bicarbonate solution, and the aqueous phase was extracted with ethyl acetate. The combined organic phases were washed with saturated sodium chloride solution, dried (Na$_2$SO$_4$) and concentrated in vacuo. The crude product was purified by column chromatography (silica gel).

| Example No. | Carboxylic acid (RCO$_2$H) | Yield (%) | MS, m/z (MH+) |
|---|---|---|---|
| 111[1a] | 3-(1-(4-Chloro-2,5-dimethylphenylsulfonyl)piperidin-2-yl)-propionic acid (Example 91) | 57 | 520.1 |
| 112 | 3-(1-(4-Methoxy-2,6-dimethylphenylsulfonyl)piperidin-2-yl)-propionic acid[2] | 87 | 516.2 |
| 113[1b] | 4-(4-Chloro-N,2,5-trimethylphenylsulfonamide)-butyric acid | 56 | 480.1 |
| 114 | 4-(4-Methoxy-N,2,6-trimethylphenylsulfonamide)-butyric acid | 71 | 476.1 |
| 115 | 4-(N-Methylnaphthalene-2-sulfonamide)-butyric acid | 77 | 468.1 |
| 116 | 4-(2,4-Dichloro-N-methylphenylsulfonamide)-butyric acid | 83 | 486.0 |
| 117 | 3-(1-(Naphthalen-2-ylsulfonyl)piperidin-2-yl)-propionic acid[2] | 69 | 508.1 |
| 118 | 3-(1-(2,4-Dichlorophenylsulfonyl)-piperidin-2-yl)-propionic acid[2] | 21 | 526.0 |
| 127[1b] | 2-((1-(4-Methoxy-2,6-dimethylphenylsulfonyl)piperidin-2-yl)methoxy)-acetic acid (acid unit S24) | 32 | 532.2 |
| 128 | (S)-2-((2-(4-Methoxy-2,6-dimethylphenylsulfonyl)-1,2,3,4-tetrahydroisoquinolin-3-yl)methoxy)-acetic acid | 48 | 580.2 |
| 129 | (S)-2-((2-(2,4-Dichlorophenylsulfonyl)-1,2,3,4-tetrahydroisoquinolin-3-yl)methoxy)-acetic acid | >99 | 590.1 |
| 130 | 2-(2-(N-benzyl-4-methoxy-2,6-dimethylphenylsulfonamide)ethoxy)-acetic acid[3] | 96 | 568.3 |
| 131[1b] | 2-((2-(2,4-Dichlorophenylsulfonyl)-1,2,3,4-tetrahydroisoquinolin-3-yl)methoxy)-acetic acid (acid unit S43) | 21 | 590.1 |
| 133 | 3-(2-(4-Methoxy-N,2,6-trimethylphenylsulfonamide)ethoxy)-propionic acid | 24 | 506.2 |
| 134 | (S)-2-((2-(4-Methoxyphenylsulfonyl)-1,2,3,4-tetrahydroisoquinolin-3-yl)methoxy)-acetic acid | 60 | 552.1 |
| 135 | 2-((1-(2,4-Dichlorophenylsulfonyl)indolin-2-yl)methoxy)-acetic acid | 90 | 576.0 |

[1a] Preparation of the corresponding hydrochloride (HCl): The free base was dissolved in a mixture of diethyl ether/methylene chloride/ethanol, and chlorotrimethylsilane (1.2 eq.) was added. The resulting hydrochloride (HCl) was obtained from the cooled solution by filtration.
[1b] Preparation of the corresponding hydrochloride (HCl): The free bases were in each case dissolved in a small amount of methyl ethyl ketone, and 2 M hydrogen chloride solution in diethyl ether (3-4 eq.) was added. The mixture was optionally cooled to 0° C. and/or diethyl ether was added thereto before the hydrochloride (HCl) was filtered off after 2-3 h.
[2] The synthesis of the acid unit was carried out analogously to acid unit S92.
[3] The synthesis was carried out analogously to Example 16, alternative solvents being used in some synthesis stages. The ester cleavage was carried out according to Method C.
[4] The synthesis of the carboxylic acid was carried out analogously to unit 58, with the exception that triethylamine was replaced by pyridine for the sulfonamide formation.

Preparation of the Carboxylic Acids (S)-2-((2-(4-Methoxy-2,6-dimethylphenylsulfonyl)-1,2,3,4-tetrahydroisoquinolin-3-yl)methoxy)acetic acid (used in the synthesis of the compound of Example 128)

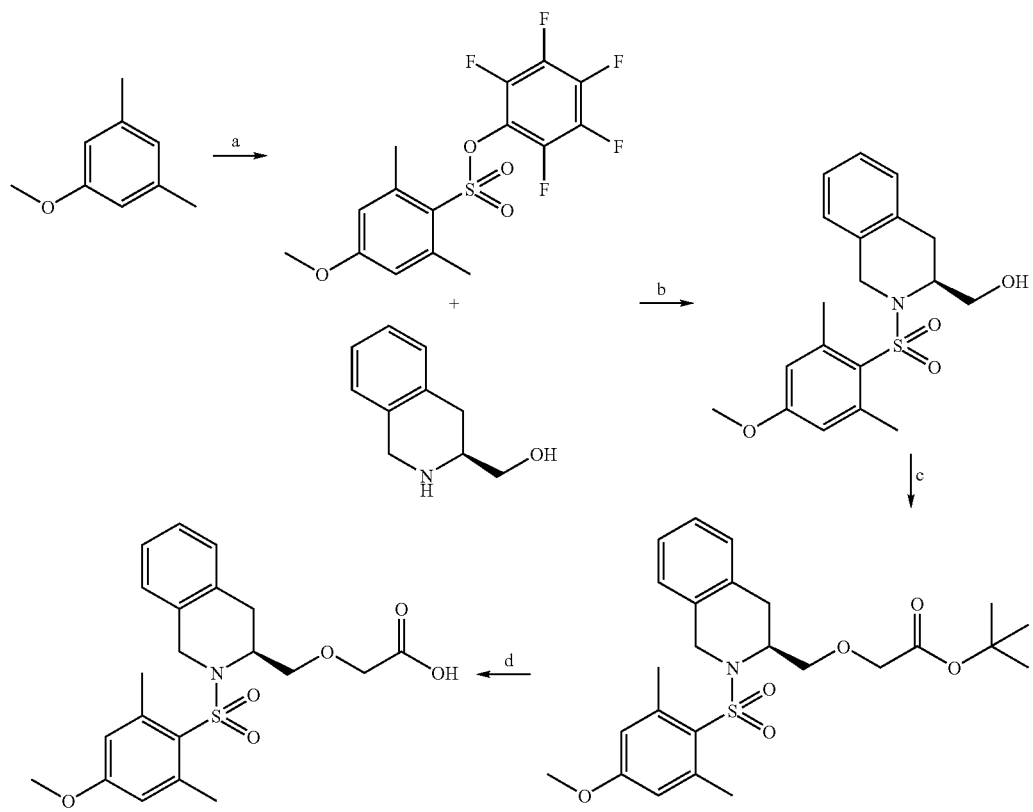

Stage (a): Chlorosulfonic acid (7.3 ml, 110.13 mmol) in methylene chloride (60 ml) was slowly added dropwise over a period of 20 min to a solution, cooled to 0° C., of 3,5-dimethylanisole (3.1 g, 22.03 mmol) in methylene chloride (50 ml). The reaction mixture was stirred for a further 10 min and then slowly added dropwise to ice-water (300 ml) and stirred until the ice had melted. The phases were separated and the aqueous phase was extracted with methylene chloride (50 ml). The combined organic phases were washed with saturated sodium chloride solution (50 ml), dried ($Na_2SO_4$) and concentrated in vacuo. A solution of pentafluorophenol (4.1 g, 22.03 mmol) and triethylamine (6.1 ml, 44.05 mmol) in methylene chloride (50 ml) was stirred for 30 min at room temperature. A solution of the prepared sulfonyl chloride in methylene chloride (50 ml) was slowly added dropwise. The reaction mixture was stirred for 1 h at room temperature. Saturated sodium bicarbonate solution (50 ml) was added to the mixture, and the organic phase was washed with saturated sodium chloride solution (50 ml), dried ($Na_2SO_4$) and concentrated in vacuo. The crude product was purified by column chromatography (silica gel) with hexane/diethyl ether/methylene chloride (20:1:2).

Yield: 6.1 g (72%)

[The undesired regioisomer was isolated in a yield of 14%.]

Stage (b): Perfluorophenyl 4-methoxy-2,6-dimethylbenzenesulfonate (1.5 g, 3.92 mmol) and tetra-n-butylammonium chloride (2.18 g, 7.85 mmol) were added to a solution of the amino alcohol (S)-(1,2,3,4-tetrahydroisoquinolin-3-yl) methanol (960 mg, 5.89 mmol) in N,N-dimethylformamide (15 ml). The reaction mixture was heated for 1 h at 120° C. Concentration in vacuo was then carried out, and the residue was taken up in ethyl acetate (50 ml) and washed with 10% ammonium chloride solution (20 ml). The organic phase was dried ($Na_2SO_4$) and concentrated in vacuo. The crude product was purified by column chromatography (silica gel) with hexane/diethyl ether/methylene chloride (3:2:2).

Yield: 1.2 g (85%)

Stage (c): tert-Butyl 2-bromoacetate (1.02 ml, 6.07 mmol) was added at room temperature to a mixture of tetra-n-butylammonium hydrogen sulfate (113 mg, 0.332 mmol), aqueous sodium hydroxide solution (6.64 g, 165.98 mmol in water (7 ml)) and toluene (5 ml), and the mixture was then cooled to 0° C. A solution of (S)-(2-(4-methoxy-2,6-dimethylphenylsulfonyl)-1,2,3,4-tetrahydroisoquinolin-3-yl)methanol (1.2 g, 3.32 mmol) in toluene (5 ml) was then added slowly. The reaction mixture was heated to room temperature and then stirred for 1 h at that temperature. The phases were separated and the aqueous phase was extracted with diethyl ether (2×20 ml). The combined organic phases were washed with saturated sodium chloride solution (20 ml), dried ($Na_2SO_4$) and concentrated in vacuo. The crude product was used in the next stage without further purification.

Yield: 1.79 g (>99%)

Stage (d): (S)-tert-butyl 2-((2-(4-methoxy-2,6-dimethylphenylsulfonyl)-1,2,3,4-tetrahydroisoquinolin-3-yl)methoxyacetate (1.58 g, 3.32 mmol) was dissolved in tetrahydrofuran (10 ml), and sodium hydroxide solution (531 mg, 13.28 mmol in water (0.5 ml)) was added. The reaction mixture was refluxed for 2 h, then cooled to room temperature again, and water (20 ml) was added. The pH value of the aqueous phase was adjusted to pH 2 with 2 M hydrochloric acid, and extraction with ethyl acetate (3×20 ml) was carried out. The crude product was used in the next stage without further purification.

Yield: 580 mg (42%)

(S)-2-((2-(2,4-Dichlorophenylsulfonyl)-1,2,3,4-tetrahydroisoquinolin-3-yl)methoxy)acetic acid (used in the synthesis of the compound of Example 129)

The synthesis of this compound was largely carried out analogously to the synthesis described for the carboxylic acid of the compound of Example 128. However, synthesis stage (a) was omitted and synthesis stage (b) was carried out as follows:

Stage (b): Triethylamine (1.27 ml, 9.19 mmol) was added to a solution of (S)-1,2,3,4-tetrahydroisoquinolin-3-yl) methanol (1.0 g, 6.13 mmol) in methylene chloride (20 ml), and the mixture was stirred for 5 min at room temperature. A solution of 2,4-dichlorobenzene-1-sulfonyl chloride (1.35 g, 5.51 mmol) in methylene chloride (10 ml) was then added dropwise at 0° C. The reaction mixture was heated to room temperature and stirred for 1 h at that temperature. Saturated sodium bicarbonate solution (20 ml) was then added to the mixture, and the aqueous phase was extracted with methylene chloride (30 ml). The combined organic phases were dried (Na$_2$SO$_4$) and concentrated in vacuo, and the crude product was then purified by column chromatography (silica gel) with hexane/diethyl ether/methylene chloride (1:1:1).

Yield: 1.59 g (70%)

Synthesis stages (c) to (d) were carried out analogously to those for the carboxylic acid of the compound of Example 128, in order to obtain the carboxylic acid.

(S)-2-((2-(4-Methoxyphenylsulfonyl)-1,2,3,4-tetrahydroisoquinolin-3-yl)methoxy)acetic acid (used in the synthesis of the compound of Example 134)

The carboxylic acid was prepared by an analogous process to (S)-2-((2-(2,4-dichlorophenylsulfonyl)-1,2,3,4-tetrahydroisoquinolin-3-yl)methoxy)acetic acid.

4-(2,4-Dichloro-N-methylphenylsulfonamide)butyric acid (used in the synthesis of the compound of Example 116)

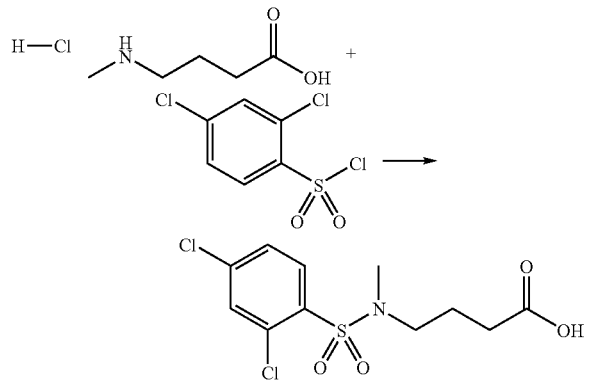

4-(Methylamino)butyric acid hydrochloride (15.36 g, 100 mmol) was added to an aqueous 4 M KOH solution (75 ml, 300 mmol), the reaction mixture being cooled with an ice bath. A solution of 2,4-dichlorophenylsulfonyl chloride (12.28 g, 50 mmol) in tetrahydrofuran (75 ml) was then added dropwise. After stirring overnight at room temperature, aqueous 6 M HCl (75 ml) was added, while cooling with an ice bath. During extraction with methylene chloride (400 ml), a precipitate formed and was filtered off. The organic phase was separated off, washed with saturated NaCl solution (200 ml), dried (Na$_2$SO$_4$), concentrated in vacuo and co-distilled with diethyl ether. Crystallization from ethyl acetate/heptane and drying overnight under a high vacuum yielded 10.48 g (64%) of the carboxylic acid.

The following carboxylic acids were prepared by analogous processes:

4-(4-chloro-N,2,5-trimethylphenylsulfonamide)butyric acid (used in the synthesis of the compound of Example 113)

4-(4-methoxy-N,2,6-trimethylphenylsulfonamide)butyric acid (used in the synthesis of the compound of Example 114)

4-(N-methylnaphthalene-2-sulfonamide)butyric acid (used in the synthesis of the compound of Example 115)

3-(2-(4-Methoxy-N,2,6-trimethylphenylsulfonamide) ethoxy)propionic acid (used in the synthesis of the compound of Example 133)

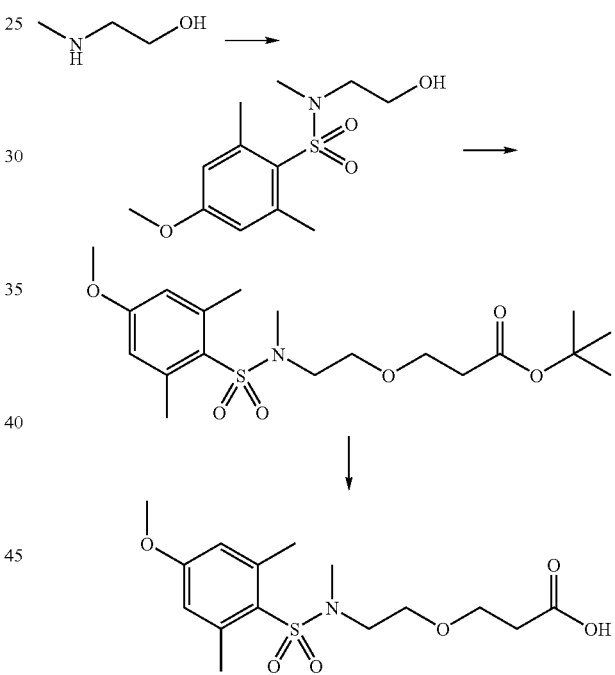

Stage (i): Triethylamine (22.5 ml, 159.78 mmol) was added to a solution of 2-(methylamino)ethanol (5.6 ml, 70.30 mmol) in methylene chloride (300 ml), and the solution was cooled to 0° C. 4-Methoxy-2,6-dimethylphenyl-1-sulfonyl chloride (15 g, 63.91 mmol) dissolved in methylene chloride (100 ml) was then added dropwise, and the mixture was stirred for 2 h at room temperature. After addition of aqueous 0.5 M HCl (100 ml), phase separation took place. The organic phase was washed with H$_2$O (2×300 ml), dried (Na$_2$SO$_4$) and concentrated. Purification by column filtration (silica gel, heptane/ ethyl acetate 1:1) yielded N-(2-hydroxyethyl)-4-methoxy-N, 2,6-trimethylphenylsulfonamide (15.7 g, 90%) in the form of a colorless oil.

Stage (ii): n-Bu$_4$NCl (5.2 g, 18.59 mmol) was added to a solution of N-(2-hydroxyethyl)-4-methoxy-N,2,6-trimethylphenylsulfonamide (15.4 g, 56.33 mmol) in toluene (250 ml), and the mixture was cooled to 0° C. 35% strength aqueous NaOH solution (300 ml) was then added, followed by the dropwise addition of tert-butyl 3-bromopropionate (11.3 ml, 67.60 mmol) in toluene (50 ml). The reaction mixture was stirred for 5 hours at room temperature before the phases were separated. The organic phase was washed neutral with water, dried (Na$_2$SO$_4$) and concentrated. Purification by column chromatography (silica gel, heptane/ethyl acetate 4:1) yielded tert-butyl 3-(2-(4-methoxy-N,2,6-trimethylphenyl-sulfonamide)-ethoxy)propionate (15.3 g, 68%) in the form of a colorless oil.

Stage (iii): Aqueous 6 M NaOH (175 ml) was added to a solution of tert-butyl 3-(2-(4-methoxy-N,2,6-trimethylphenylsulfonamide)-ethoxy)propionate (15.2 g, 37.85 mmol) in tetrahydrofuran (140 ml) and methanol (210 ml), and the mixture was stirred at room temperature. After 3 hours, the organic solvents were evaporated off, and aqueous 6 M HCl (250 ml) was added at 0° C. The aqueous phase was extracted with methylene chloride (3×250 ml). The combined organic phases were washed with saturated NaCl solution, dried (Na$_2$SO$_4$) and concentrated to dryness. The crude product was purified by column chromatography (silica gel, heptane/ethyl acetate 2:1+2% HOAc). Co-distillation with toluene (2×) and methylene chloride (3×) yielded 3-(2-(4-methoxy-N,2,6-trimethylphenylsulfonamide)ethoxy)propionic acid (10.6 g, 81%) in the form of a yellow oil.

Example 121

N-(5-(4-Hydroxy-4-(pyridin-3-yl)piperidin-1-yl)-5-oxopentyl)-4-methoxy-N,2,6-trimethylphenylsulfonamide Stage (i): Sodium hydride (2.3 g, 48 mmol) was added in portions at 0° C. to a solution of pentane-1,5-diol (5 g, 48 mmol) in tetrahydrofuran (96 ml). The resulting suspension was stirred for 30 min at 25° C. The reaction mixture was then cooled to 0° C. and benzyl bromide (2.85 ml, 24 mmol), dissolved in tetrahydrofuran, was slowly added dropwise. The mixture was then refluxed for 26 h and the progress of the reaction was monitored by thin-layer chromatography. The mixture was cooled to 0° C., water was added, and extraction with ethyl acetate (5×200 ml) was carried out. The organic phase was washed with saturated sodium chloride solution, dried (Na$_2$SO$_4$), filtered and concentrated in vacuo. The crude product was purified by column chromatography (5% methanol in methylene chloride).

Yield: 64%

Stage (ii): Triethylamine (5.26 ml, 38 mmol) was added dropwise at 0° C. to a solution of 5-benzyloxy-pentan-1-ol (5 g, 25 mmol) in methylene chloride (75 ml), followed by methanesulfonyl chloride (1.93 ml, 25 mmol). The reaction mixture was stirred for 1 h at 25° C., and the progress of the reaction was followed by thin-layer chromatography. The mixture was diluted with methylene chloride (250 ml) and washed with water and saturated sodium chloride solution. The organic phase was dried (Na$_2$SO$_4$), filtered and concentrated in vacuo. The crude product was used in the next synthesis stage without further purification.

Yield: 88%

Stage (iii): Methylamine (2 M in tetrahydrofuran, 15 ml) was added to 5-(benzyloxy)pentyl methanesulfonate (6.2 g, 22.7 mmol), and the mixture was heated for 16 h at 100° C. in

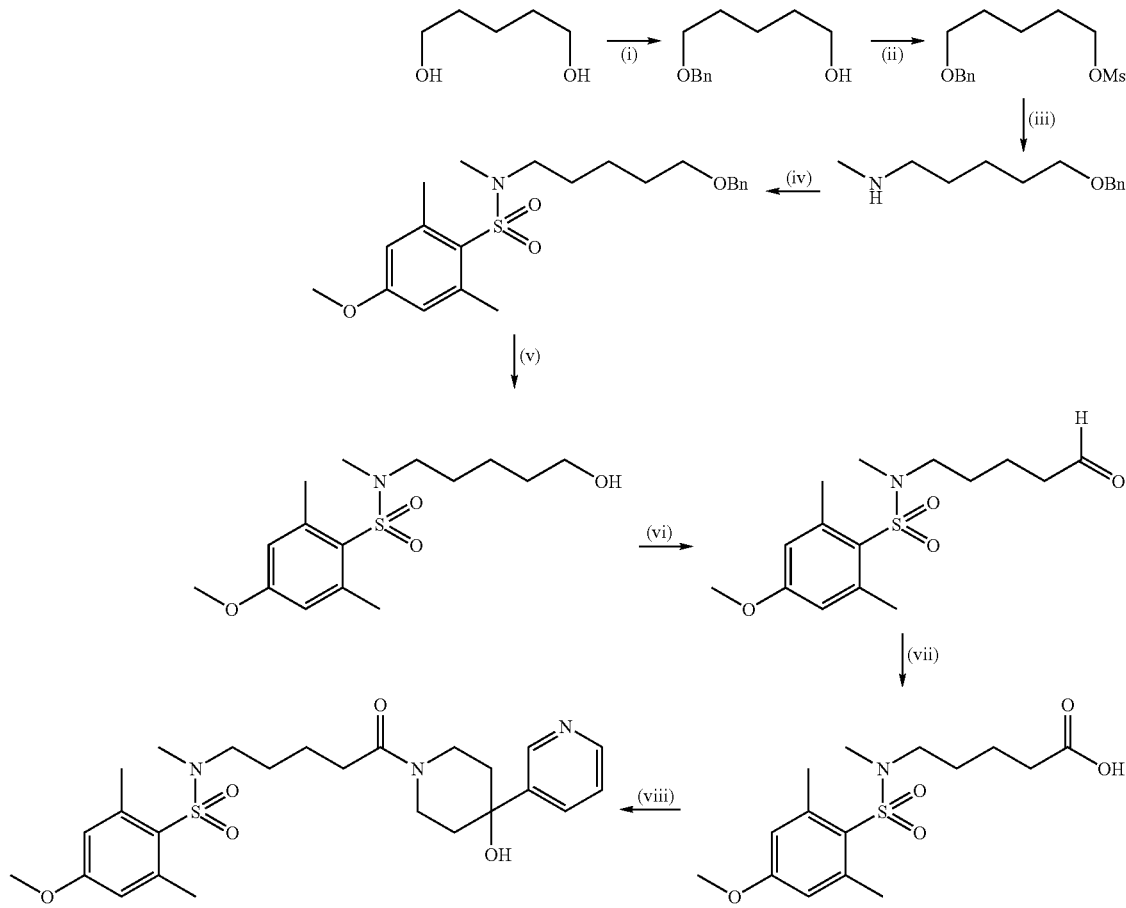

a closed vessel. The reaction mixture was cooled to 25° C. and concentrated in vacuo. The crude product was used in the next synthesis stage without further purification.

Yield: quant.

Stage (iv): Triethylamine (1.67 ml, 12.07 mmol) was added at 0° C. to 5-(benzyloxy)-N-methylpentan-1-amine (1 g, 4.83 mmol) in methylene chloride (20 ml), followed by 4-methoxy-2,6-dimethylphenyl-1-sulfonyl chloride (1.13 g, 4.83 mmol) in methylene chloride (10 ml). The reaction mixture was heated slowly to 25° C. and then stirred for 1 h. The progress of the reaction was monitored by thin-layer chromatography until the educt had reacted completely. The reaction mixture was diluted with methylene chloride and washed with water and saturated sodium chloride solution. The organic phase was dried (Na$_2$SO$_4$), filtered and concentrated in vacuo. The crude product was purified by column chromatography (15% ethyl acetate in hexane).

Yield: 28%

Stage (v): Pd(OH)$_2$ (0.60 g) was added, under an argon atmosphere, to a solution of N-(5-(benzyloxy)pentyl)-4-methoxy-N,2,6-trimethylphenylsulfonamide (0.200 g) in ethanol (5 ml), followed by a catalytic amount of acetic acid. The mixture was stirred for 16 h at 23° C. under a hydrogen atmosphere, and the progress of the reaction was monitored by thin-layer chromatography. The reaction mixture was filtered over Celite and the filter cake was washed with ethanol. Concentration in vacuo was carried out, and the crude product so obtained was used in the next synthesis stage without further purification.

Yield: quant.

Stage (vi): Dimethyl sulfoxide (0.092 ml, 1.32 mmol) in methylene chloride (2 ml) was added dropwise at −78° C., under an argon atmosphere, to a solution of oxalyl chloride (0.056 ml, 0.66 mmol) in methylene chloride (2 ml). The resulting mixture was stirred for 10 min, and then N-(5-hydroxypentyl)-4-methoxy-N,2,6-trimethylphenylsulfonamide (0.09 g, 0.6 mmol) in methylene chloride (2 ml) was added dropwise at −78° C. The reaction mixture was stirred for 1 h at −78° C. After 1 h, triethylamine (0.4 ml, 3 mmol) was added at −78° C., and the mixture was heated slowly to 25° C. and stirred for 1 h. The progress of the reaction was monitored by thin-layer chromatography until the educt had reacted completely. The reaction mixture was diluted with methylene chloride and washed with saturated ammonium chloride solution and saturated sodium chloride solution. The organic phase was dried (Na$_2$SO$_4$), filtered and concentrated in vacuo. The crude product so obtained was used in the next synthesis stage without further purification.

Yield: quant.

Stage (vii): tert-Butanol (3 ml), water (1.2 ml), a 2 M solution of 2-methyl-2-butene in tetrahydrofuran (1.08 ml) and sodium dihydrogen phosphate (1 M solution in water, 24 ml) were added to a solution of 4-methoxy-N,2,6-trimethyl-N-(5-oxopentyl)phenylsulfonamide (0.185 g, 0.59 mmol) in tetrahydrofuran (3 ml). The reaction mixture was cooled to 0° C., and sodium chlorite (0.212 g) was added. The mixture was then heated to 25° C. and stirred for 40 min (the progress of the reaction was monitored by thin-layer chromatography). The reaction mixture was diluted with water and extracted with ethyl acetate (2×50 ml). The organic phase was washed with water and saturated sodium chloride solution, dried (Na$_2$SO$_4$) and concentrated in vacuo. The crude product so obtained was used in the next synthesis stage without further purification. Yield: quant.

Stage (viii): Diisopropylethylamine (0.2 ml, 1.2 mmol) was added at 0° C. to a solution of 5-(4-methoxy-N,2,6-trimethylphenylsulfonamide)pentanoic acid (160 mg, 0.48 mmol) in methylene chloride (2 ml/mmol), followed by EDCI (0.139 g, 0.73 mmol) and HOBt (0.065 g, 0.48 mmol). The resulting solution was stirred for 15 min at 25° C. The mixture was cooled to 0° C. and 4-(pyridin-3-yl)piperidin-4-ol (0.086 mg, 0.48 mmol), dissolved in methylene chloride/N,N-dimethylformamide (1:0.25, 1.25 ml), was added dropwise. The reaction mixture was stirred for 16 h at 25° C. until the conversion was complete. The mixture was diluted with methylene chloride and washed with saturated ammonium chloride solution, saturated sodium chloride solution, saturated sodium carbonate solution and additionally with saturated sodium chloride solution. The organic phase was dried (Na$_2$SO$_4$), filtered and concentrated in vacuo. The crude product was purified by column chromatography (20% acetone in methylene chloride).

Yield: 40%

MS, m/z 490.2 (MH$^+$)

Example 139

N-(2-(2-(4-Hydroxy-4-(2-(pyridin-3-yl)ethyl)piperidin-1-yl)-2-oxoethoxy)ethyl)-4-methoxy-N,2,6-trimethylphenylsulfonamide

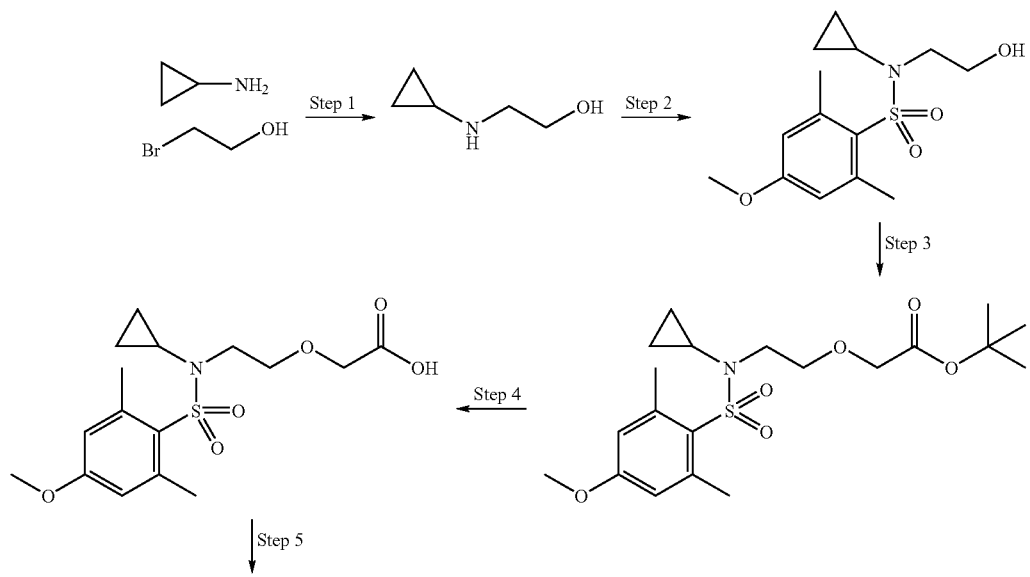

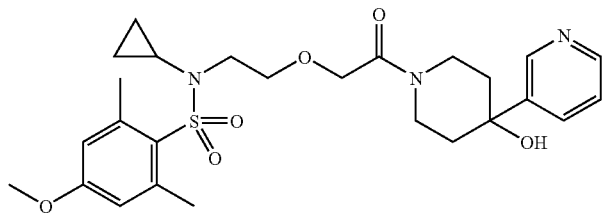

Step 1: A solution of commercially available cyclopropylamine (20 mmol) and bromoethanol (8 mmol) in ethanol (20 ml) was heated for 16 h at 50° C. The solvent was removed and the residue was co-evaporated with toluene (2×10 ml). After drying under a high vacuum, the crude product was used directly in the next step without further purification.

Yield: 65%

Step 2: A solution of 4-methoxy-2,6-dimethylbenzenesulfonyl chloride (7 mmol) in methylene chloride (12 ml) is slowly added dropwise to a solution, cooled to 0° C., of 2-cyclopropylamino-ethanol (8 mmol) in methylene chloride (24 ml) and triethylamine (2.5 eq.). When the addition is complete, the mixture is stirred for 90 min at 25° C. until the conversion is complete (TLC). The mixture was diluted with methylene chloride (200 ml) and washed with water and sat. NaCl solution. The organic phase was dried over MgSO$_4$, filtered and concentrated completely in order to obtain the desired product.

Yield: 20%

Step 3: Tetrabutylammonium chloride (0.33 eq.) and 35% strength sodium hydroxide solution (18 ml) were added to a solution, cooled to 0° C., of N-cyclopropyl-N-(2-hydroxyethyl)-4-methoxy-2,6-dimethylphenylsulfonamide (3.3 mmol) in toluene (18 ml). Tert-butyl bromoacetate (1.5 eq.) was added slowly to the mixture at 0° C. When the addition was complete, the mixture was stirred for 90 min at 25° C. until the conversion was complete (TLC). The organic phase was separated off, washed with water until a neutral pH was measured, dried over MgSO$_4$, filtered and concentrated completely in order to obtain the desired product.

Yield: 90%

Step 4: Trifluoroacetic acid (13 eq.) was added dropwise at 0° C. to a solution of tert-butyl 2-(2-(N-cyclopropyl-4-methoxy-2,6-dimethylphenylsulfonamide)ethoxy)acetate in methylene chloride (10 ml/mmol), and the resulting solution was stirred for 2 h at 25° C. The mixture was concentrated completely and traces of trifluoroacetic acid were removed under a high vacuum.

The crude product was used directly in the next synthesis step without further purification.

Step 5: Diisopropylamine (2.5 eq.) was added at 0° C. to a solution of 2-(2-(N-cyclopropyl-4-methoxy-2,6-dimethylphenylsulfonamide)ethoxy)acetic acid in methylene chloride (5 ml/mmol), followed by HOBt (1 eq.) and EDCI (1.5 eq.). The resulting solution was stirred for 15 min at 25° C. The mixture was cooled to 0° C. and 4-(pyridin-3-yl)piperidin-4-ol (1.2 eq.) was added. The mixture was stirred for 16 h at 25° C. until the conversion was complete. The mixture was diluted with methylene chloride (30 ml) and washed with sat. NH$_4$Cl solution, sat. NaCl solution, sat. NaHCO$_3$ solution and additionally with sat. NaCl solution. The organic phase was dried over MgSO$_4$ and then concentrated completely, and the residue was purified by column chromatography on silica gel (methylene chloride/methanol).

Yield: 50%

MS, m/z 518.2 (MH$^+$)

Example 140

N-(2-(2-(4-Hydroxy-4-(2-(pyridin-3-yl)ethyl)piperidin-1-yl)-2-oxoethoxy)ethyl)-4-methoxy-N,2,6-trimethylphenylsulfonamide

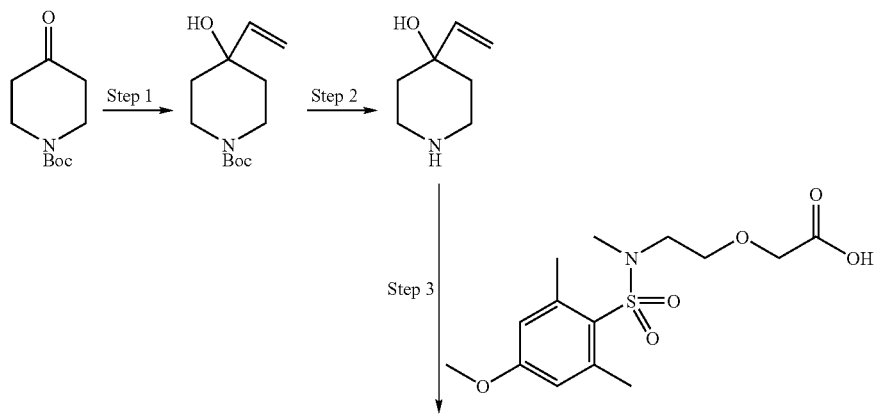

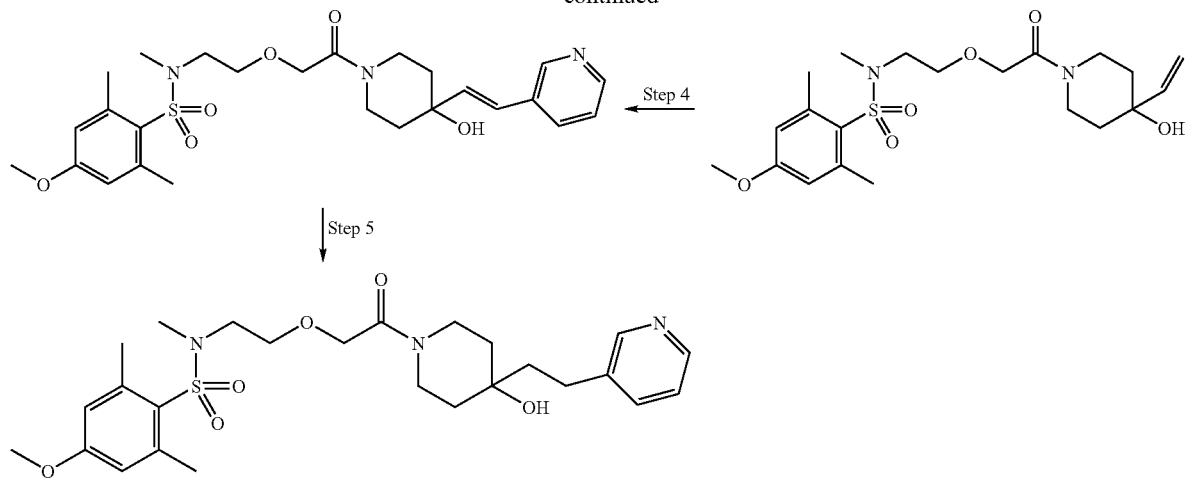

Step 1: Vinylmagnesium bromide (39.5 mmol) was added dropwise at 0° C. to a stirred solution of Boc-protected 4-oxo-piperidine (41.9 mmol) in dry tetrahydrofuran (40 ml), and the resulting solution was stirred for 16 h at 25° C. until the conversion was complete (TLC). The mixture was cooled to 0° C., sat. $NH_4Cl$ solution was added, and extraction with ethyl acetate (300 ml×2) was carried out. The combined organic phases were washed with sat. NaCl solution, dried over $MgSO_4$, filtered and concentrated completely in order to obtain the desired product.

Yield: 80%

Step 2: Trifluoroacetic acid (13 eq.) was added dropwise at 0° C. to a solution of tert-butyl 4-hydroxy-4-vinylpiperidine-1-carboxylate (1 eq.) in methylene chloride (10 ml/mmol), and the resulting solution was stirred for 2 h at 25° C. The mixture was concentrated completely and traces of trifluoroacetic acid were removed under a high vacuum. The crude amine was used directly in the next step without further purification.

Step 3: Diisopropylethylamine (2.5 eq.) was added at 0° C. to a solution of 4-vinylpiperidin-4-ol in methylene chloride (5 ml/mmol), followed by HOBt (1 eq.) and EDCI (1.5 eq.). The resulting solution was stirred for 15 min at 25° C. The mixture was cooled to 0° C. and the crude amine from step 2 (1.2 eq.) was added. The mixture was stirred for 16 h at 25° C. until the conversion was complete. The mixture was diluted with methylene chloride and washed with sat. $NH_4Cl$ solution, sat. NaCl solution, sat. $NaHCO_3$ solution and additionally with sat. NaCl solution. The organic phase was dried over $MgSO_4$ and then concentrated completely, and the residue was purified by column chromatography on silica gel (methylene chloride/methanol).

Yield: 30%

Step 4: Diisopropylethylamine (2.5 eq.) was added to a solution of 3-bromopyridine (4.7 mmol) and N-(2-(2-(4-hydroxy-4-vinylpiperidin-1-yl)-2-oxoethoxy)ethyl)-4-methoxy-N,2,6-trimethylphenylsulfonamide (5.6 mmol) in acetonitrile (20 ml), and the resulting solution was degassed for 60 min with argon. Tri-o-tolylphosphine (0.946 mmol) and $Pd(OAc)_2$ (0.47 mmol) were added to that solution under an argon atmosphere, and the resulting mixture was heated at reflux for 16 h (conversion monitored by TLC). The solvent was removed, the residue was extracted with ethyl acetate (300 ml) and the organic phase was washed with water and sat. NaCl solution. The organic phase was dried over $MgSO_4$ and then concentrated completely, and the residue was purified by column chromatography on silica gel (ethyl acetate/methanol).

Yield: 50%

Step 5: A solution of (E)-N-(2-(2-(4-hydroxy-4-(2-(pyridin-3-yl)vinyl)piperidin-1-yl)-2-oxoethoxy)ethyl)-4-methoxy-N,2,6-trimethylphenylsulfonamide (0.9 mmol) in methanol (10 ml) was degassed for 15 min with argon, and 10% Pd/C (200 mg) was added. The resulting mixture was stirred for 16 h at 25° C. under a hydrogen atmosphere (conversion monitored by TLC). The reaction mixture was filtered through Celite, the filter cake was washed thoroughly with methanol, and the filtrate was concentrated completely. The residue was purified by column chromatography on silica gel (methylene chloride/methanol).

Yield: 60%

MS, m/z 520.2 ($MH^+$)

Example 148

N-(2-(2-(4-Hydroxy-4-(pyridin-3-yl)piperidin-1-yl)-2-oxoethoxy)ethyl)-N,2-dimethylnaphthalene-1-sulfonamide

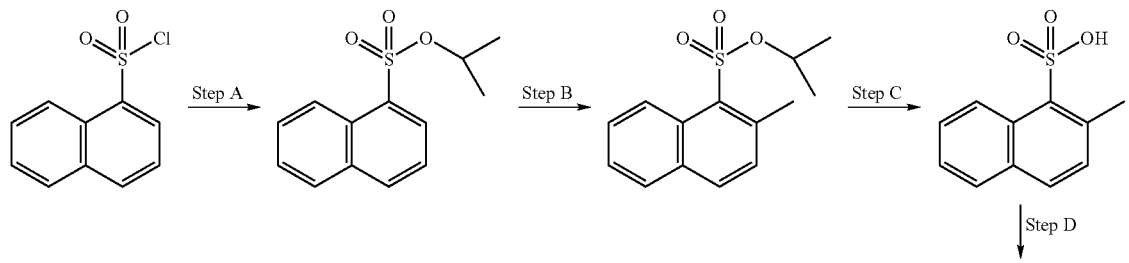

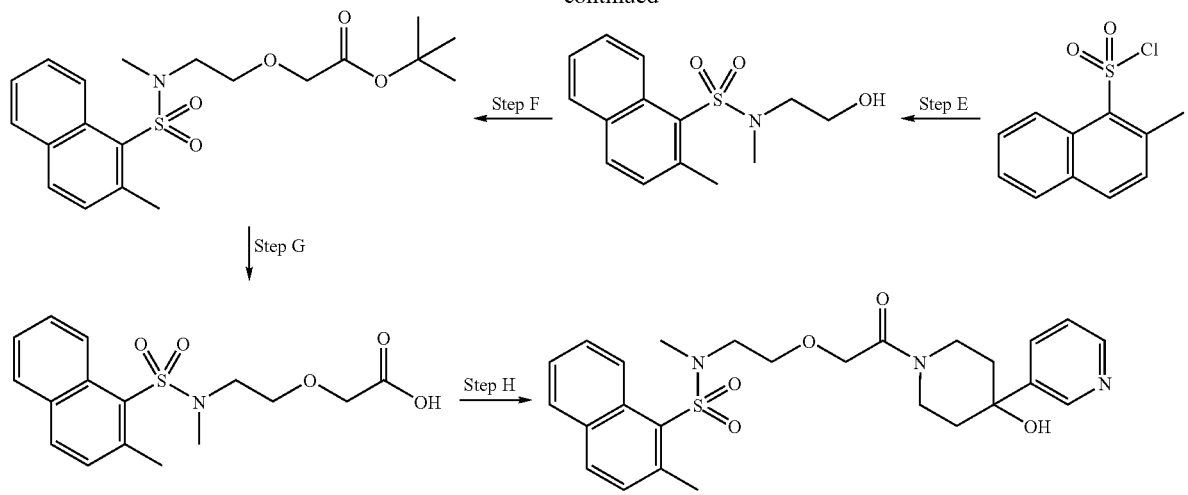

Step A: Commercially available 1-naphthylsulfonyl chloride (9.0 g) was added in portions at −5° C. to a mixture of 2-propanol (3.4 ml) and pyridine (11.5 ml). The reaction mixture was stirred for 15 h at 0° C. For working up, methylene chloride (100 ml) and 1 M HCl were added at that temperature and the organic phase was separated off. The aqueous phase was extracted with methylene chloride (3×75 ml), and the combined organic phases were washed with 1 M HCl (2×25 ml) and sat. NaCl solution (50 ml). After drying over MgSO$_4$, complete concentration was carried out and the desired product was obtained in the required purity.

Yield: 80%

Step B: The title compound from step A (8.6 g) was dissolved in tetrahydrofuran (190 ml) and the mixture was cooled to −78° C. under a protecting gas atmosphere. 1.6 M n-BuLi in n-hexane (30 ml) was added sufficiently slowly that the temperature did not rise above −70° C. The reaction mixture was stirred for 2 h at −70° C., and then methyl iodide (5.0 ml) was added. The reaction mixture was allowed to warm to 0° C. and was stirred for 3 h at that temperature. For working up, sat. NH$_4$Cl was added at that temperature, and then the mixture was diluted with ethyl acetate. The organic phase was separated off and the aqueous phase was extracted with ethyl acetate, and the combined organic phases were washed with water and sat. NaCl solution. After drying over MgSO$_4$, complete concentration was carried out and the residue was purified by column chromatography on silica gel (hexane/ethyl acetate).

Yield: 55%

Step C: The title compound from step B (1.5 g) was suspended in 4 M HCl (60 ml) and the mixture was heated for 1-2 h at 110° C. Cooling to room temperature was then carried out over a period of 15 h, the mixture was concentrated completely, and the residue obtained after co-evaporation twice with methylene chloride (2×60 ml) was dried under a high vacuum. The product so obtained was used in the next step without further purification.

Yield: quant.

Step D: The title compound from step C (1.1 g) was suspended in toluene (5 ml), and thionyl chloride (2.0 ml) and dimethylformamide (cat.) were added to the resulting mixture. Heating was then carried out for 1 h at 90° C. until a solution was present. The solution was concentrated completely and the residue was dried under a high vacuum. The product so obtained was used in the next step without further purification.

Yield: quant.

Step E: The title compound from step D (1.2 g) was dissolved at room temperature in DCM (15 ml), and 2.5 equivalents of triethylamine were added in portions. 1.2 equivalents of ethanolamine were then added dropwise, and the mixture was stirred for 2 h at room temperature. The conversion was monitored by TLC. When the conversion was complete, the reaction mixture was diluted with methylene chloride (75 ml) and water and the organic phase was separated off. The aqueous phase was extracted with methylene chloride (2×50 ml) and the combined organic phases were washed with water and sat. NaCl solution. After drying over MgSO$_4$, complete concentration was carried out and the desired product was obtained in the required purity.

Yield: 70%

Step F: The title compound from step E was dissolved in toluene (23.5 ml), and 0.33 equivalent of tetrabutylammonium chloride and 35% strength sodium hydroxide solution (23.5 ml) were added. 1.5 equivalents of tert-butyl bromoacetate were then added dropwise at the same temperature, and the mixture was stirred for 90 min at RT. When the conversion was complete, extraction with ethyl acetate was carried out and the combined organic phases were washed with water until a neutral pH was established. After drying over MgSO$_4$, complete concentration was carried out and the residue was purified by column chromatography on silica gel (hexane/ethyl acetate).

Yield: 70%

Step G: The title compound from step F was dissolved in methylene chloride (10 ml/mmol), and 13 equivalents of trifluoroacetic acid were added at 0° C. The mixture was then stirred for 2 h at room temperature. The solution was concentrated completely, and the residue was dried under a high vacuum in order to remove traces of trifluoroacetic acid. The product so obtained was used in the next step without further purification.

Step H: The title compound from step G was dissolved in methylene chloride (5 ml/mmol), and 2.5 equivalents of diisopropylethylamine, 1.0 equivalent of HOBt and 1.5 equivalents of EDCI were added at 0° C. The mixture was then stirred for 15 min at room temperature. The mixture was cooled to 0° C. again, and 1.2 equivalents of the amine dissolved in methylene chloride (30 ml) were added. The mixture was then stirred for 16 h at room temperature. When the conversion was complete, the reaction mixture was washed with methylene chloride (30 ml) and with sat. NH$_4$Cl solution, sat. NaCl solution, sat. NaHCO$_3$ solution and sat. NaCl solution. After drying over MgSO₄, complete concentration was carried out and the residue was purified by column chromatography on silica gel (methanol/methylene chloride).

Yield: 20%

MS, m/z 598 (MH⁺)

Example 280

N-(2-(2-(4-Hydroxy-4-(pyridin-4-ylmethyl)piperidin-1-yl)-2-oxoethoxy)ethyl)-4-methoxy-N,2,6-trimethylphenylsulfonamide

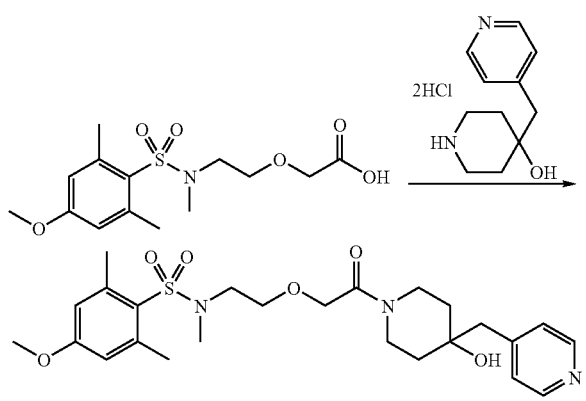

N,N'-Carbonyldiimidazole (77 mg, 0.475 mmol) was added to a solution of 2-(2-(4-methoxy-N,2,6-trimethylphenylsulfonamido)-ethoxy)acetic acid (acid unit S2) (150 mg, 0.453 mmol) in methylene chloride (7 ml), and the mixture was stirred for 1 h at room temperature. A solution of 4-(pyridin-4-ylmethyl)piperidin-4-ol dihydrochloride (120 mg, 0.453 mmol) dissolved in methylene chloride (3 ml) and triethylamine (0.18 ml) was then added, and the reaction mixture was stirred overnight at room temperature. Saturated sodium bicarbonate solution (10 ml) was then added to the reaction mixture, and the aqueous phase was then extracted with methylene chloride (20 ml). The combined organic phases were extracted with saturated sodium chloride solution (10 ml), dried with sodium sulfate and concentrated in vacuo. The crude product was purified by flash chromatography with ethyl acetate/methanol (10:1). Yield: 130 mg (57%).

Example 279

N-(2-(2-(4-Hydroxy-4-(pyridin-3-ylmethyl)piperidin-1-yl)-2-oxoethoxy)ethyl)-4-methoxy-N,2,6-trimethylphenylsulfonamide hydrochloride

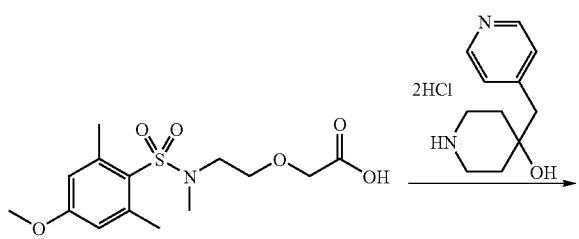

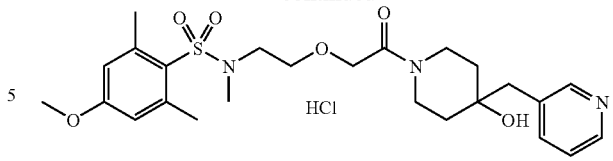

N,N'-Carbonyldiimidazole (77 mg, 0.475 mmol) was added to a solution of 2-(2-(4-methoxy-N,2,6-trimethylphenylsulfonamido)-ethoxy)acetic acid (acid unit S2) (150 mg, 0.453 mmol) in methylene chloride (7 ml), and the mixture was stirred for 1 h at room temperature. A solution of 4-(pyridin-3-ylmethyl)piperidin-4-ol dihydrochloride (120 mg, 0.453 mmol) dissolved in methylene chloride (3 ml) and triethylamine (0.18 ml) was then added, and the reaction mixture was stirred overnight at room temperature. Saturated sodium bicarbonate solution (10 ml) was then added to the reaction mixture, and the aqueous phase was then extracted with methylene chloride (20 ml). The combined organic phases were extracted with saturated sodium chloride solution (10 ml), dried with sodium sulfate and concentrated in vacuo. The crude product was purified by flash chromatography with ether/methylene chloride/methanol (10:10:1) and 25% strength ammonia solution. N-(2-(2-(4-Hydroxy-4-(pyridin-3-ylmethyl)piperidin-1-yl)-2-oxoethoxy)ethyl)-4-methoxy-N,2,6-trimethylphenylsulfonamide (140 mg) was dissolved in methyl ethyl ketone (1 ml), and HCl in ether (3 eq.) was added slowly, whereupon a white solid precipitated. After addition of diethyl ether, stirring was carried out for 1 h, while cooling with ice. The solid was filtered off, washed with diethyl ether and dried. Yield: 120 mg (48%). The amine units used in Examples 279 and 280 can be prepared analogously to the synthesis processes described above for amine units A2, A3, A4 and A7 with addition of a corresponding Li organyl or Grignard radical to the corresponding piperidone derivative.

Pharmacological Studies

Functional Investigation on the Bradykinin 1 Receptor (B1R)

The agonistic or antagonistic action of substances can be determined on the bradykinin 1 receptor (B1R) of the human and rat species with the following assay. According to this assay, the $Ca^{2+}$ inflow through the channel is quantified with the aid of a $Ca^{2+}$-sensitive dyes (Fluo-4 type, Molecular Probes Europe BV, Leiden, The Netherlands) in a fluorescent imaging plate reader (FLIPR, Molecular Devices, Sunnyvale, USA).

Method:

Chinese Hamster Ovary cells (CHO K1 cells) which are stably transfected with the human B1R gene (hB1R cells, Euroscreen s.a., Gosselies, Belgium) or the B1R gene of the rat (rB1R cells, Axxam, Milan, Italy) are used. For functional investigations, these cells are plated-out on black 96-well plates with a clear base (BD Biosciences, Heidelberg, Germany) in a density of 20,000-25,000 cells/well. Overnight, the cells are incubated at 37° C. and 5% $CO_2$ in culture medium (hB1R cells: Nutrient Mixture Ham's F12, Gibco Invitrogen GmbH, Karlsruhe, Germany; rB1R cells: D-MEM/F12, Gibco Invitrogen, Karlsruhe, Germany) with 10 vol. % FBS (foetal bovine serum, Gibco Invitrogen GmbH, Karlsruhe, Germany). On the following day, the cells are loaded with 2.13 μM Fluo-4 (Molecular Probes Europe BV, Leiden, The Netherlands) in HBSS buffer (Hank's buffered saline solution, Gibco Invitrogen GmbH, Karlsruhe, Germany) with 2.5 M probenecid (Sigma-Aldrich, Taufkirchen, Germany) and 10 mM HEPES (Sigma-Aldrich, Taufkirchen, Germany) for 60 min at 37° C. The plates are subsequently washed 2× with HBSS buffer, and HBSS buffer which additionally contains 0.1% BSA (bovine serum albumin; Sigma-Aldrich, Taufkirchen, Germany), 5.6 mM glucose and 0.05% gelatine (Merck KGaA, Darmstadt, Germany) is added. After a further incubation of 20 minutes at room temperature, the plates are inserted into the FLIPR for $Ca^{2+}$ measurement. The $Ca^{2+}$-dependent fluorescence is measured here before and after addition of substances ($\lambda_{ex}$=488 nm, $\lambda_{em}$=540 nm). The quantification is effected by measurement of the highest fluorescence intensity (FC, fluorescence counts) over time.

FLIPR Assay:

The FLIPR protocol comprises 2 additions of substance. Test substances (10 µM) are first pipetted on to the cells and the $Ca^{2+}$ inflow is compared with the control (hB1R: Lys-Des-Arg$^9$-bradykinin 0.5 nM; rB1R: Des-Arg$^9$-bradykinin 100 nM). The value in % activation based on the $Ca^{2+}$ signal after addition of Lys-Des-Arg$^9$-bradykinin (0.5 nM) or Des-Arg$^9$-bradykinin (100 nM) is obtained therefrom. After incubation for 10 minutes, 0.5 nM Lys-Des-Arg$^9$-bradykinin (hB1R) or 100 nM Des-Arg$^9$-bradykinin (rB1R) are applied and the inflow of $Ca^{2+}$ is likewise determined. Antagonists lead to a suppression of the $Ca^{2+}$ inflow. % inhibition compared with the maximum inhibition which can be achieved is calculated. The compounds show a good activity on the human and on the rat receptor. The following data were determined by way of example:

| Example | B1R antagonism, human [10 µM] % inhibition | B1R antagonism, rat [10 µM] % inhibition |
|---|---|---|
| 1 | 103.74 | 101.64 |
| 2 | 103.52 | 102.96 |
| 3 | 102.19 | 103.06 |
| 4 | 101.69 | 105.56 |
| 5 | 101.04 | 95.11 |
| 6 | 100.19 | 93.89 |
| 7 | 99.76 | 35.22 |
| 8 | 97.44 | 33.27 |
| 9 | 95.7 | 91.12 |
| 10 | 90.3 | 73.63 |
| 11 | 70.94 | . |
| 12 | 55.15 | . |
| 13 | 50.69 | . |
| 14 | 43.18 | . |
| 15 | 40.23 | . |
| 16 | 31.24 | . |
| 17 | 27.97 | 1.79 |
| 18 | 23.46 | . |
| 19 | 23.22 | . |
| 20 | 22.17 | 17.05 |
| 21 | 20.5 | 71.09 |
| 22 | 20.16 | . |
| 23 | 15.66 | 56.92 |
| 24 | 12.11 | 6.88 |
| 25 | 10.04 | . |
| 26 | 9.64 | 5.09 |
| 27 | 9.32 | . |
| 28 | 8.5 | . |
| 29 | 7.66 | . |
| 30 | 6.86 | 17.39 |
| 31 | 6.81 | . |
| 32 | 6.63 | . |
| 33 | 6.18 | 19.44 |
| 34 | 5.93 | 40.31 |
| 35 | 5.08 | . |
| 36 | 3.64 | . |
| 37 | 3.4 | . |
| 38 | 3.28 | . |
| 39 | 2.99 | . |
| 40 | 1.84 | 61.34 |
| 41 | 1.29 | −6.31 |
| 42 | 0.67 | −38.08 |
| 43 | −1.29 | 33.93 |
| 44 | −2.3 | 76.61 |
| 45 | −2.48 | . |
| 46 | −3.51 | . |
| 47 | −3.95 | . |
| 48 | −4.32 | . |
| 49 | −5.73 | 7.14 |
| 50 | −9.09 | 47.46 |
| 51 | −9.71 | 10.75 |
| 52 | −10.01 | 11.87 |
| 53 | −11.4 | . |
| 54 | −13.13 | . |
| 55 | −13.2 | . |
| 56 | −13.46 | −1.13 |
| 57 | −16.2 | . |
| 58 | −23.83 | −7.05 |
| 59 | −24.03 | 16.61 |
| 60 | −43.98 | . |
| 61 | 56.25 | 86.38 |
| 62 | 7.47 | 22.85 |
| 63 | 84.83 | 91.75 |
| 64 | 69.18 | 64.19 |
| 65 | 20.98 | 25.84 |
| 66 | 84.47 | 99.25 |
| 67 | 55.37 | 86.53 |
| 68 | 74.94 | 79.03 |
| 69 | 9.45 | 28.44 |
| 70 | 7.12 | −12.23 |
| 71 | −0.46 | 4.46 |
| 72 | 3.33 | 18.68 |
| 73 | −7.27 | 14.45 |
| 74 | −7.3 | −3.17 |
| 75 | 10.99 | 19.16 |
| 76 | 9.96 | 43.59 |
| 77 | 13.32 | −0.12 |
| 78 | 13.71 | 12.65 |
| 79 | 47.34 | 70.66 |
| 80 | 62.26 | 82.54 |
| 81 | 32.89 | 62.81 |
| 82 | 9.32 | 17.88 |
| 83 | 11.32 | −12.63 |
| 84 | −0.61 | −9.47 |
| 85 | 105.75 | 101 |
| 86 | 105.86 | 102.21 |
| 87 | 101.8 | 101.93 |
| 88 | 101.75 | 103.39 |
| 89 | 104.46 | 100.44 |
| 90 | 13.75 | 31.06 |
| 91 | 93.65 | 93.7 |
| 92 | 101.02 | 97.98 |
| 93 | −12.12 | 6.49 |
| 94 | 103.65 | 103.08 |
| 95 | 8.92 | −0.33 |
| 96 | 50.45 | 46.16 |
| 97 | 35.42 | 43.25 |
| 98 | 29.11 | 31.94 |
| 99 | −22.89 | −12.43 |
| 100 | −6.26 | −0.67 |
| 101 | 102.16 | 85.44 |
| 102 | 14.18 | 16.09 |
| 103 | −9.25 | 19.29 |
| 104 | 99.67 | 95.77 |
| 105 | 98.62 | 96.06 |
| 106 | 97.75 | 96.09 |
| 107 | 75.53 | 71.91 |
| 108 | 54.76 | 54.45 |
| 109 | 102.54 | 82.49 |
| 111 | 97.77 | 85.89 |
| 112 | 106.07 | 101.22 |
| 113 | 94.78 | 51.09 |

| Example | B1R antagonism, human [10 μM] % inhibition | B1R antagonism, rat [10 μM] % inhibition |
|---|---|---|
| 114 | 101.8 | — |
| 115 | 55.16 | 44.28 |
| 116 | 91.25 | — |
| 117 | 84.79 | 24.21 |
| 118 | 100.94 | 97.94 |
| 119 | 82.56 | 22.42 |
| 120 | 58.35 | 45.92 |
| 121 | 99.97 | 57.15 |
| 122 | 98.39 | 97.87 |
| 123 | 47.88 | 54.7 |
| 124 | 40.99 | 61.63 |
| 125 | 93.17 | 91.44 |
| 127 | 104.35 | 100.6 |
| 128 | 100.79 | 98.78 |
| 129 | 102.68 | 97.29 |
| 130 | 102.96 | 98.64 |
| 131 | 102.16 | 100.05 |
| 132 | 100.64 | 99.11 |
| 133 | 84.09 | 96.08 |
| 134 | 66.03 | 29.05 |
| 135 | 99.81 | 100.01 |
| 136 | 93.56 | 95.31 |
| 137 | 100.75 | 99.28 |
| 138 | 101.96 | 99.62 |
| 139 | 103.76 | 100.56 |
| 140 | 103.76 | 101.04 |
| 141 | 103.99 | 100.4 |
| 142 | 102.83 | 100.26 |
| 143 | 104.6 | 100.48 |
| 144 | 104.04 | 101.29 |
| 145 | — | 77.31 |
| 146 | 70.67 | 92.81 |
| 147 | 53.91 | 93.34 |
| 148 | 100.06 | 99.05 |
| 149 | 99.08 | 100.47 |
| 150 | 95.34 | 93.72 |
| 151 | 97.77 | 86.87 |
| 152 | 81.56 | 77.21 |
| 153 | 71.82 | 69.1 |
| 154 | 98.75 | 96.42 |
| 155 | 30.34 | 60.33 |
| 156 | 20.88 | 70.26 |
| 157 | 77.11 | 101.42 |
| 158 | 44.88 | 104.82 |
| 159 | 38.46 | 97.03 |
| 160 | — | 104.91 |
| 161 | 78.55 | 80.84 |
| 162 | 24.57 | 104.92 |
| 163 | 46.13 | 100.92 |
| 164 | 36.43 | 103.35 |
| 165 | 2.63 | 103.58 |
| 166 | 58.47 | 104.34 |
| 167 | 41.52 | 104.32 |
| 168 | 33.12 | 104.1 |
| 169 | 14.59 | 79.39 |
| 170 | 25.71 | 103.43 |
| 171 | 0.56 | 103.59 |
| 172 | 103.22 | 104.8 |
| 173 | 102.57 | 103.75 |
| 174 | 102.44 | 104.6 |
| 175 | 86 | 103.71 |
| 176 | 91.05 | 101.97 |
| 177 | 101.44 | 103.85 |
| 178 | 89.4 | 103.52 |
| 179 | 61.46 | — |
| 180 | 39.89 | — |
| 181 | 75.38 | — |
| 182 | 80.02 | — |
| 183 | 68.16 | — |
| 184 | 56.13 | — |
| 185 | 54.59 | — |
| 186 | 99.78 | — |
| 187 | 99.9 | — |
| 188 | 52.67 | — |
| 189 | 54.16 | — |
| 190 | 102.72 | — |
| 191 | 50.69 | — |
| 192 | 70.94 | — |
| 193 | 103.81 | 96.64 |
| 194 | 104.21 | 82.81 |
| 195 | 97.79 | 93.47 |
| 196 | 103.25 | 96.47 |
| 197 | 103.19 | 96.36 |
| 198 | 106.2 | 99.15 |
| 199 | 104.58 | 98.17 |
| 200 | 29.82 | 98.09 |
| 201 | 14.86 | 80.02 |
| 202 | 99.15 | 98.45 |
| 203 | 84.2 | 85.13 |
| 204 | 103.86 | 97.98 |
| 205 | 106.23 | 100.27 |
| 206 | 105.47 | 100.49 |
| 207 | 94.19 | 99.24 |
| 208 | 105.89 | 100.03 |
| 209 | 105.27 | 100.33 |
| 210 | 105.42 | 100.53 |
| 211 | 99.59 | 100.34 |
| 212 | 104.77 | 100.41 |
| 213 | 103.55 | 101.25 |
| 214 | 97.91 | 100.72 |
| 215 | 104.23 | 102.02 |
| 216 | 102.07 | 100.18 |
| 217 | 105.07 | 99.91 |
| 218 | 103.3 | 102.46 |
| 219 | 102.4 | 100.63 |
| 220 | 99.03 | 102.27 |
| 221 | 23.51 | 89.45 |
| 222 | 102.13 | 103.01 |
| 223 | 15.12 | 99.55 |
| 224 | 49.14 | 102.21 |
| 225 | 43.14 | 88.51 |
| 226 | 13 | 72.38 |
| 227 | 7.61 | 80.87 |
| 228 | 94.96 | 101.07 |
| 229 | 65.46 | 100.3 |
| 230 | 100.32 | 100.13 |
| 231 | 101.86 | 98.66 |
| 232 | 54.52 | 63.11 |
| 233 | 38.88 | 70.18 |
| 234 | 101.71 | 99.3 |
| 235 | 102.66 | 99.91 |
| 236 | 102.1 | 99.93 |
| 237 | 102.59 | 100.16 |
| 238 | 57.3 | 97.4 |
| 239 | 105.27 | 98.88 |
| 240 | 102.67 | 99.42 |
| 241 | 102.6 | 100.82 |
| 242 | 100.85 | 98.41 |
| 243 | 104.03 | 96.83 |
| 244 | 104.79 | 99.31 |
| 245 | 99.84 | 97.71 |
| 246 | 102.77 | 98.98 |
| 247 | — | 99.22 |
| 248 | 39.95 | 85.1 |
| 249 | 70.76 | 87.26 |
| 250 | 18.02 | 76.29 |
| 251 | 47.81 | 92.89 |
| 252 | 32.7 | 100.03 |
| 253 | — | 79.93 |
| 254 | 62.49 | 36.81 |
| 255 | 82.47 | 73.71 |
| 256 | 56.34 | 90.72 |
| 257 | 49.41 | 101.38 |
| 258 | 71.53 | 96.06 |
| 259 | 94 | 93.28 |
| 260 | 73.06 | 91.08 |
| 261 | 87.83 | 98.5 |
| 262 | 73.58 | 94.17 |
| 263 | 42.91 | 70.53 |
| 264 | 64.45 | 4.5 |

-continued

| Example | B1R antagonism, human [10 μM] % inhibition | B1R antagonism, rat [10 μM] % inhibition |
|---------|---------|---------|
| 265 | 54.06 | 29.49 |
| 266 | 21.89 | 78.62 |
| 267 | 90.59 | 97.75 |
| 268 | 99.13 | 98.8 |
| 269 | 98.36 | 99.09 |
| 270 | 93.92 | 99.66 |
| 271 | 41.89 | 78.32 |
| 272 | 54.11 | 24.09 |
| 273 | 103.15 | 100.6 |
| 274 | 96.44 | 75.96 |
| 275 | 100.46 | 92.39 |
| 276 | 70.72 | 88.29 |
| 277 | 86.84 | 88.19 |
| 278 | 96.42 | 99.87 |
| 279 | 102.97 | 104.79 |
| 280 | 100.43 | 100.01 |

Formalin Test Mouse:

The formalin test (Dubuisson, D. and Dennis, S. G., 1977, Pain, 4, 161-174) represents a model for both acute and chronic pain. By means of a single formalin injection into the dorsal side of a rear paw, a biphasic nociceptive reaction is induced in freely mobile test animals; the reaction is detected by observing three behavior patterns which are clearly distinguishable from one another. The reaction is two-phase: phase 1=immediate reaction (duration up to 10 min., shaking of the paw, licking), phase 2=late reaction (after a rest phase; likewise shaking of the paw, licking; duration up to 60 min.). The 1st phase reflects a direct stimulation of the peripheral nocisensors with high spinal nociceptive input (acute pain phase); the 2nd phase reflects a spinal and peripheral hypersensitization (chronic pain phase). In the studies described here, the chronic pain component (phase 2) has been evaluated.

Formalin Test Mouse:

Formalin in a volume of 20 μl and a concentration of 1% is administered subcutaneously into the dorsal side of the right rear paw of each animal. The specific changes in behavior, such as lifting, shaking or licking of the paw (score 3, Dubuisson & Dennis, 1977), are observed and recorded in the observation period of 21 to 24 min following the formalin injection.

The behavior of the animals after administration of the substance (n=10 per dose of substance) was compared with a control group which received vehicle (n=10). Based on the quantification of the pain behavior, the activity of the test substance in the formalin test was determined as the change, in percent, compared with the control. The time of administration before the formalin injection was chosen in dependence on the mode of administration of the compounds according to the invention (intravenous: 5 min.).

The antionociceptive activity of some examples is shown in the following table:

| Example | Type of administration | Substance action |
|---------|-----------------------|------------------|
| 110 | i.v. | 45% antinociception at 10 mg/kg |
| 87 | i.v. | 23% antinociception at 10 mg/kg |

Parenteral Solution of a Substituted Sulfonamide Derivative According to the Invention 38 g of one of the substituted sulfonamide compounds according to the invention, in this case Example 1, are dissolved at room temperature in 1 liter of water for injection purposes, and the solution is subsequently adjusted to isotonic conditions by addition of anhydrous glucose for injection purposes.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A substituted sulfonamide derivative of the general formula I

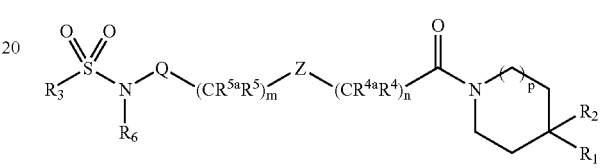

I wherein m represents 1, 2 or 3 n represents 1 or 2 p represents 1, $R^1$ represents thienyl, phenyl, benzyl, phenethyl, pyridyl, or pyridyl linked via a —CH$_2$— or —CH$_2$—CH$_2$— chain, in each case unsubstituted or mono- or poly-substituted, $R^2$ represents OH, OC$_{1-6}$-alkyl or F, $R^3$ represents aryl or heteroaryl, in each case unsubstituted or mono- or poly-substituted;

$R^4$ and $R^{4a}$ independently of one another represent H, C$_{1-6}$-alkyl, in each case saturated or unsaturated, branched or unbranched, unsubstituted or mono- or poly-substituted; F; Cl; aryl, in each case unsubstituted or mono- or poly-substituted; or aryl linked via a C$_{1-3}$-alkyl chain and in each case unsubstituted or mono- or poly-substituted;

Z represents O;

$R^5$ and $R^{5a}$ independently of one another represent H; or C$_{1-6}$-alkyl, in each case saturated or unsaturated, branched or unbranched, unsubstituted or mono- or poly-substituted; OH, OC$_{1-6}$-alkyl, F, Cl, phenoxy or benzyloxy;

$R^6$ represents H; C$_{1-6}$-alkyl, in each case saturated or unsaturated, branched or unbranched, unsubstituted or mono- or poly-substituted; C$_{3-8}$-cycloalkyl, saturated or unsaturated, unsubstituted or mono- or poly-substituted; aryl or heteroaryl, unsubstituted or mono- or poly-substituted; aryl or C$_{3-8}$-cycloalkyl linked via a C$_{1-3}$-alkyl chain;

Q denotes —CH$_2$—, —CH$_2$—CH$_2$—, or

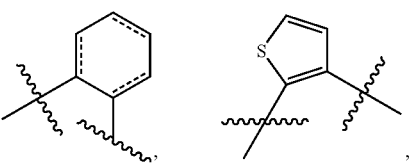

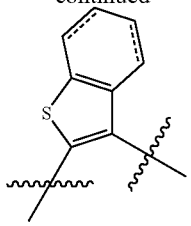

wherein ---- represents a single bond or a double bond;
  in the form of a pure stereoisomer or a mixture of stereoisomers in any mixing ratio; or
  a pharmaceutically acceptable salt thereof.

2. A compound according to claim 1, wherein said compound is in the form of a pure enantiomer or diastereomer.

3. A compound according to claim 1, wherein said compound is in the form of a racemic mixture.

4. A compound according to claim 1, wherein
  m represents 1, 2 or 3
  n represents 1 or 2
  p represents 1,
  $R^1$ represents thienyl, phenyl, benzyl, phenethyl, pyridyl, or pyridyl linked via a —$CH_2$— or —$CH_2$—$CH_2$- chain, in each case unsubstituted or mono- or poly-substituted,
  $R^2$ represents OH, $OC_{1-6}$-alkyl or F,
  $R^3$ represents aryl or heteroaryl, in each case unsubstituted or mono- or poly-substituted;
  $R^4$ and $R^{4a}$ independently of one another represent H, $C_{1-6}$-alkyl, in each case saturated or unsaturated, branched or unbranched, unsubstituted or mono- or poly-substituted; F; Cl; aryl, in each case unsubstituted or mono- or poly-substituted; or aryl linked via a $C_{1-3}$-alkyl chain and in each case unsubstituted or mono- or poly-substituted;
  Z represents O;
  $R^5$ and $R^{5a}$ independently of one another represent H; or $C_{1-6}$-alkyl, in each case saturated or unsaturated, branched or unbranched, unsubstituted or mono- or poly-substituted; OH, $OC_{1-6}$-alkyl, F, Cl, phenoxy or benzyloxy;
  $R^6$ represents H; $C_{1-6}$-alkyl, in each case saturated or unsaturated, branched or unbranched, unsubstituted or mono- or poly-substituted; $C_{3-8}$-cycloalkyl, saturated or unsaturated, unsubstituted or mono- or poly-substituted; aryl or heteroaryl, unsubstituted or mono- or poly-substituted; aryl or $C_{3-8}$-cycloalkyl linked via a $C_{1-3}$-alkyl chain; or $Cl_{1-6}$-alkyl;
  Q denotes —$CH_2$—, —$CH_2$—$CH_2$—, or

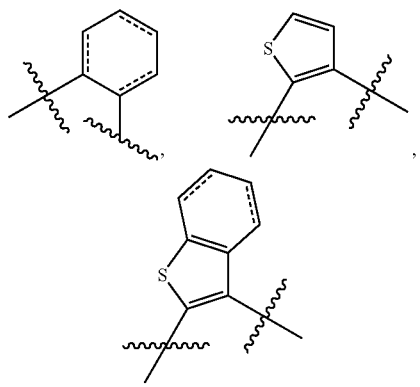

wherein ---- represents a single bond or a double bond;
wherein
  "alkyl substituted" and "cycloalkyl substituted" denotes replacement of one or more hydrogen radicals by F, Cl, Br, I, —CN, $NH_2$, NH—$C_{1-6}$-alkyl, NH—$C_{1-6}$-alkyl-OH, $C_{1-6}$-alkyl, $N(C_{1-6}$-alkyl$)_2$, $N(C_{1-6}$-alkyl-OH$)_2$, $NO_2$, SH, S—$C_{1-6}$-alkyl, S-benzyl, O—$C_{1-6}$-alkyl, OH, O—$C_{1-6}$-alkyl-OH, =O, O-benzyl, $C(=O)C_{1-6}$-alkyl, $CO_2H$, $CO_2$—$C_{1-6}$-alkyl, phenyl or benzyl;
  "aryl substituted" and "heteroaryl substituted" denotes replacement one or more times, e.g. two, three or four times, of one or more hydrogen atoms of the ring system by F, Cl, Br, I, CN, $NH_2$, NH—$C_{1-6}$-alkyl, NH—$C_{1-6}$-alkyl-OH, $N(C_{1-6}$-alkyl$)_2$, $N(C_{1-6}$-alkyl-OH$)_2$, $NO_2$, SH, S—$C_{1-6}$-alkyl, OH, O—$C_{1-6}$-alkyl, O—$C_{1-6}$alkyl-OH, $C(=O)C_{1-6}$-alkyl, $CO_2H$, $CH_2SO_2$-phenyl, $CO_2$—$C_{1-6}$-alkyl, $OCF_3$, $CF_3$,

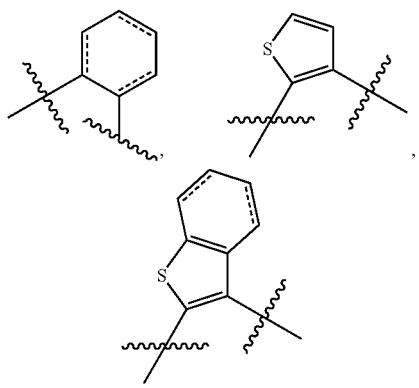

$C_{1-6}$-alkyl, phenyl, pyridyl, thienyl or furyl.

5. A compound according to claim 1, wherein $R^3$ denotes phenyl, naphthyl, thienyl or benzothiophene, in each case unsubstituted or mono- or poly-substituted.

6. A compound according to claim 1, wherein
  $R^6$ denotes H, methyl, ethyl, n-propyl, isobutyl, cyclopropyl, cyclopropyl linked via a $C_{1-3}$-alkyl chain, or benzyl.

7. A compound according to claim 1, wherein $R^4$ and $R^{4a}$ each represent H.

8. A compound according to claim 1, wherein $R^5$ and $R^{5a}$ each represent H.

9. A compound according to claim 1, wherein
  m represents 1,
  n represents 1 or 2
  $R^4$, $R^{4a}$, $R^5$ and $R^{5a}$ each represent H, and
  Z represents O;
  or
  m represents 2,
  Z represents O,
  n represents 1, and
  $R^4$ and $R^{4a}$, $R^5$ and $R^{5a}$ each represent H.

10. A compound according to claim 1, wherein $R^2$ denotes OH.

11. A compound according to claim 1, wherein $R^3$ denotes 2,6-dimethyl-4-methoxyphenyl.

12. A compound according to claim 1, selected from the group consisting of:
  1   N-{2-[2-(4-benzyl-4-hydroxy-piperidin-1-yl)-2-oxo-ethoxy]-ethyl}-N-ethyl-4-methoxy-2,3,6-trimethyl-phenylsulfonamide 2  2,4,6-trichloro-N-{2-[2-(4'-hydroxy-3',4',5',6'-tetrahydro-2'H-[3,4']bipyridinyl-1'-yl)-2-oxo-ethoxy]-ethyl}-N-methyl-phenylsulfonamide
3  N-(2-(2-(4-hydroxy-4-(pyridin-3-yl)piperidin-1-yl)-2-oxoethoxy)ethyl)-4-methoxy-N,2,6-trimethylphenylsulfonamide hydrochloride
4  N-{2-[2-(4'-hydroxy-3',4',5',6-tetrahydro-2'H-[2,4']bipyridinyl-1'-yl)-2-oxo-ethoxy]-ethyl}-4-methoxy-2,6,N-trimethyl-phenylsulfonamide
5  2,4,6-trichloro-N-(2-(2-(4-hydroxy-4-(pyridin-3-yl)piperidin-1-yl)-2-oxoethoxy)ethyl)-N-methylphenylsulfonamide hydrochloride
6  2,4,6-trichloro-N-{2-[2-(4'-hydroxy-3',4',5',6'-tetrahydro-2'H-[2,4']bipyridinyl-1'-yl)-2-oxo-ethoxy]-ethyl}-N-methyl-phenylsulfonamide
7  1-(4-benzyl-4-hydroxy-piperidin-1-yl)-2-[1-(4-methoxy-2,3,6-trimethyl-phenylsulfonyl)-pyrrolidin-3-yloxy]-ethanone
8  1-(4-benzyl-4-hydroxy-piperidin-1-yl)-2-[1-(4-methoxy-2,3,6-trimethyl-phenylsulfonyl)-piperidin-4-yloxy]-ethanone
9  N-{2-[2-(4-benzyl-4-hydroxy-piperidin-1-yl)-2-oxoethoxy]-ethyl}-2,4,6-trichloro-N-methyl-phenylsulfonamide
10  2,6-dichloro-N-{2-[2-(4'-hydroxy-3',4',5',6'-tetrahydro-2'H-[2,4']bipyridinyl-1'-yl)-2-oxo-ethoxy]-ethyl}-N-methyl-phenylsulfonamide
11  1-(4-benzyl-4-hydroxy-piperidin-1-yl)-2-[1-(4-methoxy-2,3,6-trimethyl-phenylsulfonyl)-piperidin-3-yloxy]-ethanone
12  2-[1-(3,4-dichloro-phenylsulfonyl)-piperidin-2-ylmethoxy]-1-(4'-hydroxy-3',4',5',6'-tetrahydro-2'H-[3,4']bipyridinyl-1'-yl)-ethanone
13  N-benzyl-N-{2-[2-(4-benzyl-4-hydroxy-piperidin-1-yl)-2-oxo-ethoxy]-ethyl}-4-methoxy-2,3,6-trimethyl-phenylsulfonamide
16  N-{2-[2-(4-benzyl-4-hydroxy-piperidin-1-yl)-2-oxoethoxy]-ethyl}-3,4-dimethoxy-N-methyl-phenylsulfonamide
20  N-{2-[2-(4'-hydroxy-3',4',5',6'-tetrahydro-2'H-[2,4']bipyridinyl-1'-yl)-2-oxo-ethoxy]-ethyl}-N-methyl-4-trifluoromethoxy-phenylsulfonamide
28  N-{2-[2-(4-benzyl-4-hydroxy-piperidin-1-yl)-2-oxoethoxy]-ethyl}-4-methoxy-N-methyl-phenylsulfonamide
38  N-{2-[2-(4-benzyl-4-hydroxy-piperidin-1-yl)-2-oxoethoxy]-ethyl}-N-methyl-3-trifluoromethyl-phenylsulfonamide
39  N-{2-[2-(4-benzyl-4-hydroxy-piperidin-1-yl)-2-oxoethoxy]-ethyl}-N-methyl-phenylsulfonamide
41  N-{2-[2-(4'-hydroxy-3',4',5',6'-tetrahydro-2'H-[2,4']bipyridinyl-1'-yl)-2-oxo-ethoxy]-ethyl}-3,4-dimethoxy-N-methyl-phenylsulfonamide
42  N-{2-[2-(4'-hydroxy-3',4',5',6'-tetrahydro-2'H-[2,4']bipyridinyl-1'-yl)-2-oxo-ethoxy]-ethyl}-4-methoxy-N-methyl-phenylsulfonamide
43  N-{2-[2-(4-benzyl-4-hydroxy-piperidin-1-yl)-2-oxoethoxy]-cyclohexyl}-3,4-dichloro-N-methyl-phenylsulfonamide
61  N-(2-(2-(4-(4-chlorophenyl)-4-hydroxypiperidin-1-yl)-2-oxoethoxy)ethyl)-5-fluoro-N,2-dimethylphenylsulfonamide
62  N-{2-[2-(4-benzyl-4-hydroxy-piperidin-1-yl)-2-oxoethoxy]-ethyl}-5-fluoro-2,N-dimethyl-phenylsulfonamide
69  N-benzyl-N-{2-[2-(4-benzyl-4-hydroxy-piperidin-1-yl)-2-oxo-ethoxymethyl]-thiophen-3-yl}-3,4-dichlorophenylsulfonamide
70  3,5-difluoro-N-{2-[2-(4'-hydroxy-3',4',5',6'-tetrahydro-2'H-[2,4']bipyridinyl-1'-yl)-2-oxo-ethoxy]-ethyl}-N-methyl-phenylsulfonamide
71  2,5-difluoro-N-{2-[2-(4'-hydroxy-3',4',5',6'-tetrahydro-2'H-[2,4']bipyridinyl-1'-yl)-2-oxo-ethoxy]-ethyl}-N-methyl-phenylsulfonamide
86  N-{2-[2-(4-hydroxy-4-thiophen-2-yl-piperidin-1-yl)-2-oxo-ethoxy]-ethyl}-4-methoxy-2,6,N-trimethyl-phenylsulfonamide
88  N-{2-[2-(4-hydroxy-3,4,5,6-tetrahydro-2H-[4,4']bipyridinyl-1-yl)-2-oxo-ethoxy]-ethyl}-4-methoxy-2,6,N-trimethyl-phenylsulfonamide
93  N-(2-(2-(4-(4-chlorophenyl)-4-hydroxypiperidin-1-yl)-2-oxoethoxy)ethyl)-3,5-difluoro-N-methylphenylsulfonamide
97  5-fluoro-N-{2-[2-(4'-hydroxy-3',4',5',6'-tetrahydro-2'H-[2,4']bipyridinyl-1'-yl)-2-oxo-ethoxy]-ethyl}-2,N-dimethyl-phenylsulfonamide
102  5-chloro-thiophene-2-sulfonic acid {2-[2-(4'-hydroxy-3',4',5',6'-tetrahydro-2'H-[3,4']bipyridinyl-1'-yl)-2-oxo-ethoxy]-ethyl}-methyl-amide
103  5-chloro-thiophene-2-sulfonic acid {2-[2-(4'-hydroxy-3',4',5',6'-tetrahydro-2'H-[2,4']bipyridinyl-1'-yl)-2-oxo-ethoxy]-ethyl}-methyl-amide
104  2,4-dichloro-N-(2-(2-(4-(4-chlorophenyl)-4-hydroxypiperidin-1-yl)-2-oxoethoxy)ethyl)-N,6-dimethylphenylsulfonamide
105  2,4-dichloro-N-(2-(2-(4-hydroxy-4-phenylpiperidin-1-yl)-2-oxoethoxy)ethyl)-N,6-dimethylphenylsulfonamide
106  N-{2-[2-(4-benzyl-4-hydroxy-piperidin-1-yl)-2-oxoethoxy]-ethyl}-2,4-dichloro-6,N-dimethyl-phenylsulfonamide
130  N-benzyl-N-(2-(2-(4-hydroxy-4-(pyridin-3-yl)piperidin-1-yl)-2-oxoethoxy)ethyl)-4-methoxy-2,6-dimethylphenylsulfonamide
132  N-(2-(2-(4-hydroxy-4-(3-(trifluoromethyl)phenyl)piperidin-1-yl)-2-oxoethoxy)ethyl)-4-methoxy-N,2,6-trimethylphenylsulfonamide
133  N-(2-(3-(4-hydroxy-4-(pyridin-3-yl)piperidin-1-yl)-3-oxopropoxy)ethyl)-4-methoxy-N,2,6-trimethylphenylsulfonamide
136  N-(2-(2-(4-(4-chlorophenyl)-4-hydroxypiperidin-1-yl)-2-oxoethoxy)ethyl)-4-methoxy-N,2,6-trimethylphenylsulfonamide
137  N-(2-(2-(4-hydroxy-4-phenylpiperidin-1-yl)-2-oxoethoxy)ethyl)-4-methoxy-N,2,6-trimethylphenylsulfonamide
139  N-cyclopropyl-N-(2-(2-(4-hydroxy-4-(pyridin-3-yl)piperidin-1-yl)-2-oxoethoxy)ethyl)-4-methoxy-2,6-dimethylphenylsulfonamide
140  N-(2-(2-(4-hydroxy-4-(2-(pyridin-3-yl)ethyl)piperidin-1-yl)-2-oxoethoxy)ethyl)-4-methoxy-N,2,6-trimethylphenylsulfonamide
141  N-(2-(2-(4-(3-fluorophenyl)-4-hydroxypiperidin-1-yl)-2-oxoethoxy)ethyl)-4-methoxy-N,2,6-trimethylphenylsulfonamide
143  N-(2-(2-(4-hydroxy-4-(pyridin-3-yl)piperidin-1-yl)-2-oxoethoxy)ethyl)-4-methoxy-N,2,6-trimethylphenylsulfonamide
148  N-(2-(2-(4-hydroxy-4-(pyridin-3-yl)piperidin-1-yl)-2-oxoethoxy)ethyl)-N,2-dimethylnaphthalene-1-sulfonamide 149 4-chloro-N-(2-(2-(4-hydroxy-4-(pyridin-3-yl)piperidin-1-yl)-2-oxoethoxy)ethyl)-N,2,5-trimethylphenylsulfonamide 150 4-chloro-N-(2-(2-(4-(4-chlorophenyl)-4-hydroxypiperidin-1-yl)-2-oxoethoxy)ethyl)-N,2,5-trimethylphenylsulfonamide 151 N-(2-(2-(4-(4-bromophenyl)-4-hydroxypiperidin-1-yl)-2-oxoethoxy)ethyl)-4-chloro-N,2,5-trimethylphenylsulfonamide 152 4-chloro-N-(2-(2-(4-hydroxy-4-phenylpiperidin-1-yl)-2-oxoethoxy)ethyl)-N,2,5-trimethylphenylsulfonamide 153 N-(2-(2-(4-benzyl-4-hydroxypiperidin-1-yl)-2-oxoethoxy)ethyl)-4-chloro-N,2,5-trimethylphenylsulfonamide 154 4-chloro-N-(2-(2-(4-hydroxy-4-(3-(trifluoromethyl)phenyl)piperidin-1-yl)-2-oxoethoxy)ethyl)-N,2,5-trimethylphenylsulfonamide 191 N-benzyl-N-(2-(2-(4-benzyl-4-hydroxypiperidin-1-yl)-2-oxoethoxy)ethyl)-4-methoxy-2,3,6-trimethylphenylsulfonamide 198 2,4-dichloro-N-(2-(2-(4-hydroxy-4-(pyridin-2-yl)piperidin-1-yl)-2-oxoethoxy)ethyl)-N,6-dimethylphenylsulfonamide 199 2,4-dichloro-N-(2-(2-(4-hydroxy-4-(pyridin-3-yl)piperidin-1-yl)-2-oxoethoxy)ethyl)-N,5-dimethylphenylsulfonamide 205 N-(2-(2-(4-(4-bromophenyl)-4-hydroxypiperidin-1-yl)-2-oxoethoxy)ethyl)-N-(cyclopropylmethyl)-4-methoxy-2,3,6-trimethylphenylsulfonamide 206 N-(cyclopropylmethyl)-N-(2-(2-(4-hydroxy-4-phenylpiperidin-1-yl)-2-oxoethoxy)ethyl)-4-methoxy-2,3,6-trimethylphenylsulfonamide 207 N-(2-(2-(4-benzyl-4-hydroxypiperidin-1-yl)-2-oxoethoxy)ethyl)-N-(cyclopropylmethyl)-4-methoxy-2,3,6-trimethylphenylsulfonamide 208 N-(cyclopropylmethyl)-N-(2-(2-(4-hydroxy-4-(3-(trifluoromethyl)phenyl)-piperidin-1-yl)-2-oxoethoxy)ethyl)-4-methoxy-2,3,6-trimethylphenyl-sulfonamide 209 N-(2-(2-(4-(4-chlorophenyl)-4-hydroxypiperidin-1-yl)-2-oxoethoxy)ethyl)-N-isobutyl-4-methoxy-2,3,6-trimethylphenylsulfonamide 210 N-(2-(2-(4-(4-bromophenyl)-4-hydroxypiperidin-1-yl)-2-oxoethoxy)ethyl)-N-isobutyl-4-methoxy-2,3,6-trimethylphenylsulfonamide 211 N-(2-(2-(4-benzyl-4-hydroxypiperidin-1-yl)-2-oxoethoxy)ethyl)-N-isobutyl-4-methoxy-2,3,6-trimethylphenylsulfonamide 212 N-(2-(2-(4-hydroxy-4-(3-(trifluoromethyl)phenyl)piperidin-1-yl)-2-oxoethoxy)ethyl)-N-isobutyl-4-methoxy-2,3,6-trimethylphenylsulfonamide 237 N-(2-(2-(4-(4-chloro-3-(trifluoromethyl)phenyl)-4-hydroxypiperidin-1-yl)-2-oxoethoxy)ethyl)-N-(cyclopropylmethyl)-4-methoxy-2,3,6-trimethylphenyl-sulfonamide 238 N-(2-(2-(4-(4-chloro-3-(trifluoromethyl)phenyl)-4-hydroxypiperidin-1-yl)-2-oxoethoxy)ethyl)-N-isobutyl-4-methoxy-2,3,6-trimethylphenylsulfonamide 240 N-(cyclopropylmethyl)-N-(2-(2-(4-hydroxy-4-(pyridin-3-yl)piperidin-1-yl)-2-oxoethoxy)ethyl)-4-methoxy-2,3,6-trimethylphenylsulfonamide 241 N-(2-(2-(4-hydroxy-4-(pyridin-3-yl)piperidin-1-yl)-2-oxoethoxy)ethyl)-N-isobutyl-4-methoxy-2,3,6-trimethylphenylsulfonamide 256 N-(2-(2-(4-(4-chlorophenyl)-4-hydroxypiperidin-1-yl)-2-oxoethoxy)ethyl)-N,2,5-trimethylthiophene-3-sulfonamide 257 N-(2-(2-(4-(4-bromophenyl)-4-hydroxypiperidin-1-yl)-2-oxoethoxy)ethyl)-N,2,5-trimethylthiophene-3-sulfonamide 258 N-(2-(2-(4-hydroxy-4-(3-(trifluoromethyl)phenyl)piperidin-1-yl)-2-oxoethoxy)ethyl)-N,2,5-trimethylthiophene-3-sulfonamide 259 N-(2-(2-(4-(4-chloro-3-(trifluoromethyl)phenyl)-4-hydroxypiperidin-1-yl)-2-oxoethoxy)ethyl)-N,2,5-trimethylthiophene-3-sulfonamide 260 2,5-dichloro-N-(2-(2-(4-(4-chlorophenyl)-4-hydroxypiperidin-1-yl)-2-oxoethoxy)ethyl)-N-methylthiophene-3-sulfonamide 261 N-(2-(2-(4-(4-bromophenyl)-4-hydroxypiperidin-1-yl)-2-oxoethoxy)ethyl)-2,5-dichloro-N-methylthiophene-3-sulfonamide 262 2,5-dichloro-N-(2-(2-(4-hydroxy-4-(3-(trifluoromethyl)phenyl)piperidin-1-yl)-2-oxoethoxy)ethyl)-N-methylthiophene-3-sulfonamide 263 2,5-dichloro-N-(2-(2-(4-(4-chloro-3-(trifluoromethyl)phenyl)-4-hydroxypiperidin-1-yl)-2-oxoethoxy)ethyl)-N-methylthiophene-3-sulfonamide 268 N-(cyclopropylmethyl)-N-(2-(2-(4-hydroxy-4-(thiophen-2-yl)piperidin-1-yl)-2-oxoethoxy)ethyl)-4-methoxy-2,3,6-trimethylphenylsulfonamide 269 N-(2-(2-(4-hydroxy-4-(thiophen-2-yl)piperidin-1-yl)-2-oxoethoxy)ethyl)-N-isobutyl-4-methoxy-2,3,6-trimethylphenylsulfonamide 275 N-(2-(3-(4-(4-chlorophenyl)-4-hydroxypiperidin-1-yl)-3-oxopropoxy)ethyl)-4-methoxy-N,2,6-trimethylphenylsulfonamide 276 N-(2-(3-(4-hydroxy-4-phenylpiperidin-1-yl)-3-oxopropoxy)ethyl)-4-methoxy-N,2,6-trimethylphenylsulfonamide 277 N-(2-(3-(4-benzyl-4-hydroxypiperidin-1-yl)-3-oxopropoxy)ethyl)-4-methoxy-N,2,6-trimethylphenylsulfonamide 278 N-(2-(3-(4-(4-chloro-3-(trifluoromethyl)phenyl)-4-hydroxypiperidin-1-yl)-3-oxopropoxy)ethyl)-4-methoxy-N,2,6-trimethylphenylsulfonamide.

13. A process for preparing a substituted sulfonamide compound according to claim 1, said process comprising:
reacting a carboxylic acid corresponding to formula G with a primary or secondary amine corresponding to formula S:

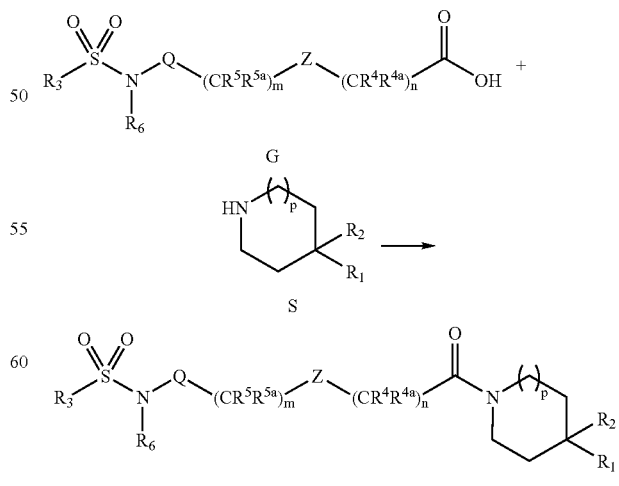

in the presence of a dehydrating agent, or in the presence of a coupling reagent, and an organic base in organic solvent.

14. A method according to claim 13, wherein the dehydrating agent is selected from the group consisting of sodium sulfate, magnesium sulfate and phosphorus oxide; the coupling agent is CDI or polymer-bonded DCC, TBTU, EDCI, PyBOP or PFPTFA; HOAt or HOBt is added; the organic base is selected from the group consisting of DIPEA and pyridine, and the organic solvent is selected from the group consisting of THF, methylene chloride, diethyl ether, dioxane, DMF and acetonitrile.

15. A pharmaceutical composition comprising a compound according to claim 1 and at least one pharmaceutically acceptable carrier, additive or auxiliary substance.

* * * * *